(12) United States Patent
Xu

(10) Patent No.: US 6,664,377 B1
(45) Date of Patent: Dec. 16, 2003

(54) COMPOUNDS FOR IMMUNOTHERAPY OF PROSTATE CANCER AND METHODS FOR THEIR USE

(75) Inventor: Jiangchun Xu, Bellevue, WA (US)

(73) Assignee: Corixa Corporation, Seattle, WA (US)

(*) Notice: Subject to any disclaimer, the term of this patent is extended or adjusted under 35 U.S.C. 154(b) by 70 days.

(21) Appl. No.: 09/688,489

(22) Filed: Oct. 13, 2000

Related U.S. Application Data

(60) Division of application No. 09/232,149, filed on Jan. 15, 1999, now Pat. No. 6,465,611, which is a continuation-in-part of application No. 09/159,812, filed on Sep. 23, 1998, which is a continuation-in-part of application No. 09/115,453, filed on Jul. 14, 1998, which is a continuation-in-part of application No. 09/030,607, filed on Feb. 25, 1998, now Pat. No. 6,262,245, which is a continuation-in-part of application No. 09/020,956, filed on Feb. 9, 1998, now Pat. No. 6,261,562, which is a continuation-in-part of application No. 08/904,804, filed on Aug. 1, 1997, now abandoned, which is a continuation-in-part of application No. 08/806,099, filed on Feb. 25, 1997, now abandoned.

(51) Int. Cl.$^7$ .................. C07K 16/00; C07K 5/00; C07K 21/04; C12Q 1/68; C12P 19/34; A61K 39/395

(52) U.S. Cl. ................ 530/387.1; 435/6; 435/91.1; 435/91.2; 424/130.1; 530/300; 530/350; 536/23.1; 536/24.3

(58) Field of Search ............... 435/6, 91.1, 91.2; 530/300, 350, 387.1; 536/23.1, 24.3; 424/130.1

(56) References Cited

FOREIGN PATENT DOCUMENTS

| DE | 19649207 | 11/1996 |
|---|---|---|
| EP | 317 141 A2 | 5/1989 |
| EP | 652 014 A1 | 5/1995 |
| EP | 936 270 A2 | 8/1999 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/14772 | 6/1995 |
| WO | WO 95/30758 | 11/1995 |
| WO | WO 96/21671 | 7/1996 |
| WO | WO 97/33909 | 9/1997 |
| WO | WO 98/12302 | 3/1998 |
| WO | WO 98/17687 | 4/1998 |
| WO | WO 98/20117 | 5/1998 |
| WO | WO 98/31799 | 7/1998 |
| WO | WO 98/37039 | 8/1998 |
| WO | WO 98/37093 | 8/1998 |
| WO | WO 98/37418 | 8/1998 |
| WO | WO 98/38310 | 9/1998 |
| WO | WO 98/39446 | 9/1998 |
| WO | WO 98/45435 | 10/1998 |
| WO | WO 98/50567 | 11/1998 |
| WO | WO 99/06548 | 2/1999 |
| WO | WO 99/06550 | 2/1999 |
| WO | WO 99/06552 | 2/1999 |
| WO | WO 99/25825 | 5/1999 |
| WO | WO 99/31236 | 6/1999 |
| WO | WO 00/04149 | 1/2000 |
| WO | WO 01/25272 | 4/2001 |
| WO | WO 01/34802 | 5/2001 |
| WO | WO 01/51633 | 7/2001 |

OTHER PUBLICATIONS

Sequence Homology Search.*
Schmitz et al., "Purification of characterization of an alpha–methylacyl–CoA racemase from human liver," European Journal of Biochemistry, 1995, vol. 231, pp. 815–822.*
King et al., "A Dictionary of Genetics," Oxford University Press, 5$^{th}$ edition, 1997, p. 25.*
Ahn and Kunkel, "The structural and functional diversity of dystrophin," Nature Genetics 3: 283–291, Apr., 1993.
Alexeyev et al., "Improved antibiotic–resistance gene cassettes and omega elements for Escherichia coli vector construction and in vitro deletion/insertion mutagenesis," Gene 160:63–67, 1995.
Berthon et al., "Predisposing gene for early–onset prostate cancer, localized on chromosome 1q42.2–43," Am. J. Hum. Genet. 62(6):1416–1424, Jun. 1998.
Blok et al., "Isolation of cDNA that are differentially expressed between androgen–dependent and androgen–independent prostate carcinoma cells using differential display PCR," The Prostate 26:213–224, 1995.
Busselmakers et al., Genbank Accession No. AF103907, Aug. 14, 2000.
Busselmakers et al., Genbank Accession No. AF103908, Aug. 14, 2000.
Cawthon et al., "cDNA sequence and genomic structure of EVI2B, a gene lying within an intron of the neurofibromatosis type 1 gene," Genomics 9:446–460, 1991.
Chu et al., "CpG oligodeoxynucleotides act as adjuvants that switch on T helper 1 (Th1) immunity," J. Exp. Med. 186(10): 1623–1631, Nov. 17, 1997.
Coleman et al., Fundamental Immunology, Wm. C. Brown Publishers, Dubuque, Iowa, 1989, pp. 465–466.
Database EMBL Accesion No. AA453562, Jun. 11, 1997, Hillier et al., "Homo sapiens cDNA clone 788180."
Derwent Geneseq Database, Accession No. V58522, Dec. 8, 1998.
Derwent Geneseq Database, Accession No. V61287, Jan. 6, 1999.

(List continued on next page.)

Primary Examiner—Jeffrey Siew
Assistant Examiner—Young Kim
(74) Attorney, Agent, or Firm—Seed Intellectual Property Law Group PLLC

(57) ABSTRACT

Compounds and methods for treating prostate cancer are provided. The inventive compounds include polypeptides containing at least a portion of a prostate tumor protein. Vaccines and pharmaceutical compositions for immunotherapy of prostate cancer comprising such polypeptides, or DNA molecules encoding such polypeptides, are also provided, together with DNA molecules for preparing the inventive polypeptides.

4 Claims, 6 Drawing Sheets

OTHER PUBLICATIONS

Duerst and Nees, "Nucleic acid characteristic of late or early passage cells immortalized by papilloma virus–and related polypeptide(s) and antibodies, used for diagnosis and treatment of cervical cancer and assessing potential for progression of cervical lesions," Derwent World Patent Index, Accession No. 1998–121623, 1998. See also German Patent DE 19649207 C1.

El–Shirbiny, Prostatic Specific Antigen, *Advances In Clinical Chemistry* 31:99–133, 1994.

Ezzell, C., "Cancer vaccines: an idea whose time has come?" *The Journal of NIH Research* 7:46–49, Jan., 1995.

Hara et al., "Characterization of cell phenotype by a novel cDNA library subtraction system: expression of CD8α in a mast cell–derived interleukin–4–dependent cell line," *Blood* 84(1):189–199, Jul. 1, 1994.

Harris et al., "Polycystic Kidney Disease 1: identification and analysis of the primary defect," *J. Am. Soc. of Nephrol.* 6:1125–1133, 1995.

Hillier et al., Genbank Accession No. AA100799, Dec. 23, 1997.

Hillier et al., Genbank Accession No. R20590, Apr. 18, 1995.

Hudson, T., Genbank Accession No. G22461, May 31, 1996.

Kroger, B. "New serine protease form human prostate, useful for identifying specific inhibitors, antibodies and probes," Derwent World Patent Index, Accession No. 99–432218, 1999. See also European Patent EP 936 270 A2.

Lalvani et al., "Rapid effector function in CD8$^+$ memory cells," *J. Exp. Med.* 186(6):859–865, Sep. 15, 1997.

National Cancer Institute, Cancer Genome Anatomy Project (NCI–CGAP), Genbank Accession No. AA551449, Sep. 5, 1997.

National Cancer Institute, Cancer Genome Anatomy Project (NCI–CGAP), Genbank Accession No. AA551759, Aug. 11, 1997.

National Cancer Institute, Cancer Genome Anatomy Project (NCI–CGAP), Genbank Accession No. AA631143, Oct. 31, 1997.

National Cancer Institute, Cancer Genome Anatomy Project (NCI–CGAP), Genbank Accession No. AA653016, Nov. 25, 1997.

Nelson et al., Genbank Accession No. NP_004908, Mar. 18, 2000.

Robson et al., "Indentification of prostatic adrogen regulated genes using the differential display technique," *Proceeding of the American Association for Cancer Research Meeting 86, 36*: p. 266, Abstract No. 1589, 1995.

Schena et al., "Parallel human genome analysis: Microarray–based expression monitoring of 1000 genes," *Proc. Natl. Acad. Sci. USA* 93(19):10614–10619, Sep. 17, 1996.

Sherman et al., "Selecting T cell receptors with high affinity for self–MHC by decreasing the contribution of CD8," *Science* 258(5083):815–818, Oct. 30, 1992.

Short et al., "λ ZAP: a bacteriophage λ expression vector with in vivo excision properties," *Nucleic Acids Research* 16(15):7583–7600, 1988.

Sjögren, H., "Therapeutic Immunization Against Cancer Antigens Using Genetically Engineered Cells," *Immunotechnology* 3: 161–172, 1997.

Smith et al., "Major susceptibility locus for prostate cancer on chromosome 1 suggested by a genome–wide search," *Science* 274(5291), 1371–1374, Nov. 22, 1996.

Theobald, et al., "Targeting p53 as a general tumor antigen," *Proc. Natl. Sci. USA* 92(25):11993–11997, Dec. 5, 1995.

Tusnady and Simon, "Principles governing amino acid compositions of integral membrane proteins: application to topology prediction," *J. Mol. Biol.* 283(2):489–506, Oct. 23, 1998.

Van Tsai et al., "In vitro immunization and expansion of antigen–specific cytotoxic T lymphocytes for adoptive immunotherapy using peptide–pulsed dendritic cells," *Critical Reviews in Immunology* 18:65–75, 1998.

Vasmatzis et al., "Discovery of three genes specifically expressed in human prostate by expressed sequence tag database analysis," *Proc. Natl. Acad. Sci. USA* 95:300–304, Jan. 6, 1998.

Yee et al., "Isolation of tyrosinase–specific CD8$^+$ and CD4$^+$ T cell clones from the peripheral blood of melanoma patients following in vitro stimulation with recombinant vaccinia virus," *The Journal of Immunology* 157(9):4079–4086, Nov. 1, 1996.

Zitvogel et al., "Eradication of Established Murine Tumors Using a Novel Cell–Free Vaccine: Dendritic Cell–Derived Exosomes," *Nature Medicine* 4(5): 594–600, May, 1998.

GenBank Accession Number AF047020, Feb. 1, 1999.

Schmidt–Wolf et al., "Activated T cells and cytokine–induced CD3$^+$ CD56$^+$ killer cells," *Annals of Hematology* 74:51–56, 1997.

\* cited by examiner

SEQUENCE LISTING

<160> NUMBER OF SEQ ID NOS: 338

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
ttttttttttt tttttcacag tataacagct ctttatttct gtgagttcta ctaggaaatc      60
atcaaatctg agggttgtct ggaggacttc aatacacctc cccccatagt gaatcagctt     120 ccaggggggtc cagtccctct ccttacttca tccccatccc atgccaaagg aagaccctcc     180
ctccttggct cacagccttc tctaggcttc ccagtgcctc caggacagag tgggttatgt     240
tttcagctcc atccttgctg tgagtgtctg gtgcgttgtg cctccagctt ctgctcagtg     300
cttcatggac agtgtccagc acatgtcact ctccactctc tcagtgtgga tccactagtt     360
ctagagcggc cgccaccgcg gtggagctcc agcttttgtt ccctttagtg agggttaatt     420
gcgcgcttgg cgtaatcatg gtcataactg tttcctgtgt gaaattgtta tccgctcaca     480
attccacaca acatacgagc cggaagcata agtgtaaag cctggggtgc ctaatgagtg     540
anctaactca cattaattgc gttgcgctca ctgnccgctt tccagtcngg aaaactgtcg     600
tgccagctgc attaatgaat cggccaacgc ncggggaaaa gcggtttgcg ttttggggggc     660 tcttccgctt ctcgctcact nantcctgcg ctcggtcntt cggctgcggg gaacggtatc     720
actcctcaaa ggnggtatta cggttatccn naaatcnggg gataccncgg aaaaantttt     780
aacaaagggg cancaaaggg cngaaacgta aaaa                                  814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

```
acagaaatgt tggatggtgg agcacctttc tatacgactt acaggacagc agatggggaa      60
ttcatggctg ttggagcaat agaaccccag ttctacgagc tgctgatcaa aggacttgga     120
ctaaagtctg atgaacttcc caatcagatg agcatggat attggccaga aatgaagaag     180
aagtttgcag atgtatttgc aaagaagacg aaggcagagt ggtgtcaaat ctttgacggc     240
acagatgcct gtgtgactcc ggttctgact tttgaggagg ttgttcatca tgatcacaac     300
aaggaacggg gctcgtttat caccagtgag gagcaggacg tgagcccccg ccctgcacct     360
ctgctgttaa acaccccagc catcccttct ttcaaaaggg atccactagt tctagaagcg     420
gccgccaccg cggtggagct ccagcttttg ttccctttag tgagggttaa ttgcgcgctt     480
ggcgtaatca tggtcatagc tgtttcctgt gtgaaattgt tatccgctca caattccccc     540
```

```
aacatacgag ccggaacata aagtgttaag cctggggtgc ctaatgantg agctaactcn    600
cattaattgc gttgcgctca ctgcccgctt tccagtcggg aaaactgtcg tgccactgcn    660
ttantgaatc ngccaccccc cgggaaaagg cggttgcntt ttgggcctct tccgctttcc    720
tcgctcattg atcctngcnc ccggtcttcg gctgcggnga acggttcact cctcaaaggc    780
ggtntnccgg ttatccccaa acngggata  cccnga                              816

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3
cttttgaaag aagggatggc tggggtgttt aacagcagag gtgcagggcg ggggctcacg     60
tcctgctcct cactggtgat aaacgagccc cgttccttgt tgtgatcatg atgaacaacc    120
tcctcaaaag tcagaaccgg agtcacacag gcatctgtgc cgtcaaagat ttgacaccac    180
tctgccttcg tcttctttgc aaatacatct gcaaacttct tcttcatttc tggccaatca    240
tccatgctca tctgattggg aagttcatca gactttagtc canntccttt gatcagcagc    300
tcgtagaact ggggttctat tgctccaaca gccatgaatt ccccatctgc tgtcctgtaa    360
gtcgtataga aggtgctcc  accatccaac atgttctgtc ctcgagggg  ggcccggtac    420 ccaattcgcc ctatantgag tcgtattacg cgcgctcact ggccgtcgtt ttacaacgtc    480
gtgactggga aaccctgggc cgttaccaac ttaatcgcct tgcagcacat ccccctttcg    540
ccagctgggc gtaatancga aaaggcccgc accgatcgcc cttccaacag ttgcgcacct    600
gaatgggnaa atgggacccc cctgttaccg cgcattaaac cccgcnggg  tttngttgtt    660 accccacnt  nnaccgctta cactttgcca gcgccttanc gcccgctccc tttcnccttt    720
cttcccttcc tttcncnccn ctttccccg  ggtttcccc  cntcaaaccc cna            773

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4
cctcctgagt cctactgacc tgtgctttct ggtgtggagt ccaggctgc  taggaaaagg     60 aatgggcaga cacaggtgta tgccaatgtt tctgaaatgg gtataatttc gtcctctcct    120
tcggaacact ggctgtctct gaagacttct cgctcagttt cagtgaggac acacacaaag    180
acgtgggtga ccatgttgtt tgtggggtgc agagatggga gggtgggggc ccaccctgga    240
agagtggaca gtgacacaag gtggacactc tctacagatc actgaggata agctggagcc    300
acaatgcatg aggcacacac acagcaagga tgacnctgta aacatagccc acgctgtcct    360
gngggcactg ggaagcctan atnaggccgt gagcanaaag aaggggagga tccactagtt    420
ctanagcggc cgccaccgcg gtggnactcc ancttttgtt ccctttagtg agggttaatt    480
gcgcgcttgg cntaatcatg gtcatanctn tttcctgtgt gaaattgtta tccgctcaca    540
attccacaca acatacgganc cggaaacata aantgtaaac ctggggtgcc taatgantga    600
```

| | | |
|---|---|---|
| ctaactcaca ttaattgcgt tgcgctcact gcccgctttc caatcnggaa acctgtcttg | 660 | |
| ccncttgcat tnatgaatcn gccaacccc ggggaaaagc gtttgcgttt tgggcgctct | 720 | |
| tccgcttcct cnctcantta ntccctncnc tcggtcattc cggctgcngc aaaccggttc | 780 | |
| accncctcca aaggggtat tccggtttcc ccnaatccgg gganancc | 828 | |

<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

| | | |
|---|---|---|
| tttttttttt tttttactga tagatggaat ttattaagct tttcacatgt gatagcacat | 60 | |
| agttttaatt gcatccaaag tactaacaaa aactctagca atcaagaatg cagcatgtt | 120 | |
| attttataac aatcaacacc tgtggctttt aaaatttggt tttcataaga taatttatac | 180 | |
| tgaagtaaat ctagccatgc ttttaaaaaa tgctttaggt cactccaagc ttggcagtta | 240 | |
| acatttggca taaacaataa taaaacaatc acaatttaat aaataacaaa tacaacattg | 300 | |
| taggccataa tcatatacag tataaggaaa aggtggtagt gttgagtaag cagttattag | 360 | |
| aatagaatac cttggcctct atgcaaatat gtctagacac tttgattcac tcagccctga | 420 | |
| cattcagttt tcaaagtagg agacaggttc tacagtatca ttttacagtt tccaacacat | 480 | |
| tgaaaacaag tagaaaatga tgagttgatt tttattaatg cattacatcc tcaagagtta | 540 | |
| tcaccaaccc ctcagttata aaaattttc aagttatatt agtcatataa cttggtgtgc | 600 | |
| ttattttaaa ttagtgctaa atggattaag tgaagacaac aatggtcccc taatgtgatt | 660 | |
| gatattggtc attttacca gcttctaaat ctnaacttc aggcttttga actggaacat | 720 | |
| tgnatnacag tgttccanag ttncaaccta ctggaacatt acagtgtgct tgattcaaaa | 780 | |
| tgttattttg ttaaaaatta aattttaacc tggtggaaaa ataatttgaa atna | 834 | |

<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

| | | |
|---|---|---|
| tttttttttt tttttttttt aagaccctca tcaatagatg gagacataca gaaatagtca | 60 | |
| aaccacatct acaaaatgcc agtatcaggc ggcggcttcg aagccaaagt gatgtttgga | 120 | |
| tgtaaagtga atattagtt ggcggatgaa gcagatagtg aggaaagttg agccaataat | 180 | |
| gacgtgaagt ccgtggaagc ctgtggctac aaaaaatgtt gagccgtaga tgccgtcgga | 240 | |
| aatggtgaag ggagactcga agtactctga ggcttgtagg agggtaaaat agagacccag | 300 | |
| taaaattgta ataagcagtg cttgaattat tggtttcgg ttgttttcta ttagactatg | 360 | |
| gtgagctcag gtgattgata ctcctgatgc gagtaatacg gatgtgttta ggagtgggac | 420 | |
| ttctagggga tttagcgggg tgatgcctgt tgggggccag tgccctccta gttgggggt | 480 | |
| aggggctagg ctggagtggt aaaaggctca gaaaaatcct gcgaagaaaa aaacttctga | 540 | |

```
ggtaataaat aggattatcc cgtatcgaag gccttttgg acaggtggtg tgtggtggcc      600
ttggtatgtg ctttctcgtg ttacatcgcg ccatcattgg tatatggtta gtgtgttggg      660
ttantanggc ctantatgaa gaactttgg antggaatta aatcaatngc ttggccggaa      720
gtcattanga nggctnaaaa ggccctgtta ngggtctggg ctnggtttta cccnacccat      780
ggaatncncc ccccggacna ntgnatccct attcttaa                              818

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7
tttttttttt tttttttttt tggctctaga gggggtagag gggtgctat agggtaaata       60 cgggccctat ttcaaagatt tttagggaa ttaattctag gacgatgggt atgaaactgt      120
ggtttgctcc acagatttca gagcattgac cgtagtatac ccccggtcgt gtagcggtga     180
aagtggtttg gtttagacgt ccggaattg catctgtttt taagcctaat gtggggacag      240
ctcatgagtg caagacgtct tgtgatgtaa ttattatacn aatgggggct tcaatcggga     300
gtactactcg attgtcaacg tcaaggagtc gcaggtcgcc tggttctagg aataatgggg     360
gaagtatgta ggaattgaag attaatccgc cgtagtcggt gttctcctag gttcaatacc     420
attggtggcc aattgatttg atggtaaggg gagggatcgt tgaactcgtc tgttatgtaa     480 aggatnccctt ngggatggga aggcnataa ggactangga tnaatggcgg gcangatatt    540
tcaaacngtc tctanttcct gaaacgtctg aaatgttaat aanaattaan tttngttatt    600
gaatnttnng gaaaagggct tacaggacta gaaaccaaat angaaaanta atnntaaggg    660
cnttatcntn aaaggtnata accnctccta tnatcccacc caatngnatt ccccacncnn    720
acnattggat ncccanttc canaaanggc cnccccccgg tgnanncnc cttttgttcc     780 cttnantgan ggttattcnc ccctngcntt atcancc                             817

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8
catttccggg tttactttct aaggaaagcc gagcggaagc tgctaacgtg ggaatcggtg       60
cataaggaga actttctgct ggcacgcgct agggacaagc gggagagcga ctccgagcgt      120
ctgaagcgca cgtcccagaa ggtggacttg cactgaaaac agctgggaca catccgcgag      180
tacgaacagc gcctgaaagt gctggagcgg gaggtccagc agtgtagccg cgtcctgggg      240
tgggtggccg angcctganc cgctctgcct tgctgccccc angtgggccg ccaccccctg      300
acctgcctgg gtccaaacac tgagccctgc tggcggactt caagganaac ccccacangg      360
ggattttgct cctanantaa ggctcatctg ggcctcggcc cccccacctg gttggccttg      420
tctttgangt gagcccatg tccatctggg ccactgtcng gaccacctttt ngggagtgtt      480 ctccttacaa ccacannatg cccggctcct cccggaaacc antcccancc tgngaaggat     540
```

```
caagncctgn atccactnnt nctanaaccg gccnccnccg cngtggaacc cnccttntgt    600
tccttttcnt tnagggttaa tnncgccttg gccttnccan ngtcctncnc nttttccnnt    660
gttnaaattg ttangcnccc nccnntcccn cnncnncnan cccgacccnn annttnnann    720 ncctggggt  nccnncngat tgacccnncc nccctntant tgcnttnggg nncnntgccc    780
ctttccctct nggganncg                                                 799

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9
acgccttgat cctcccaggc tgggactggt tctgggagga gccgggcatg ctgtggtttg     60
taangatgac actcccaaag gtggtcctga cagtggccca gatggacatg gggctcacct    120
caaggacaag gccaccaggt gcgggggccg aagcccacat gatccttact ctatgagcaa    180
aatcccctgt gggggcttct ccttgaagtc cgccancagg gctcagtctt tggacccang    240
caggtcatgg ggttgtngnc caactggggg ccncaacgca aaanggcnca gggcctcngn    300
cacccatccc angacgcggc tacactnctg gacctcccnc tccaccactt tcatgcgctg    360
ttcntacccg cgnatntgtc ccanctgttt cngtgccnac tccancttct nggacgtgcg    420
ctacatacgc ccggantcnc nctcccgctt tgtccctatc cacgtnccan caacaaattt    480
cnccntantg caccnattcc cacntttnnc agntttccnc nncgngcttc cttntaaaag    540
ggttganccc cggaaaatnc cccaagggg  ggggccngg  tacccaactn ccccctnata    600
gctgaantcc ccatnaccnn gnctcnatgg ancnntccnt tttaannacn ttctnaactt    660
gggaanancc ctcgnccntn cccccnttaa tcccncccttg cnangnncnt ccccnntcc    720 ncccnnntng gcntntnann cnaaaaaggc ccnnnancaa tctcctnncn cctcanttcg    780
ccanccctcg aaatcggccn c                                              801

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10
cagtctatnt ggccagtgtg gcagctttcc ctgtggctgc cggtgccaca tgcctgtccc     60
acagtgtggc cgtggtgaca gcttcagccg ccctcaccgg gttcaccttc tcagccctgc    120
agatcctgcc ctacacactg gcctccctct accaccggga gaagcaggtg ttcctgccca    180
aataccgagg ggacactgga ggtgctagca gtgaggacag cctgatgacc agcttcctgc    240
caggccctaa gcctggagct cccttcccta atggacacgt gggtgctgga ggcagtggcc    300
tgctcccacc tccacccgcg ctctgcgggg cctctgcctg tgatgtctcc gtacgtgtgg    360
tggtgggtga gccaccgan  gccagggtgg ttccggggcc gggcatctgc ctggacctcg    420
ccatcctgga tagtgcttcc tgctgtccca ngtggcccca tccctgttta tgggctccat    480
```

| | |
|---|---:|
| tgtccagctc agccagtctg tcactgccta tatggtgtct gccgcaggcc tgggtctggt | 540 |
| cccatttact ttgctacaca ggtantattt gacaagaacg anttggccaa atactcagcg | 600 |
| ttaaaaaatt ccagcaacat tgggggtgga aggcctgcct cactgggtcc aactccccgc | 660 |
| tcctgttaac cccatggggc tgccggcttg gccgccaatt tctgttgctg ccaaantnat | 720 |
| gtggctctct gctgccacct gttgctggct gaagtgcnta cngcncanct nggggggtng | 780 |
| ggngttccc | 789 |

```
<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11
```

| | |
|---|---:|
| cccaccctac ccaaatatta gacaccaaca cagaaaagct agcaatggat tcccttctac | 60 |
| tttgttaaat aaataagtta aatatttaaa tgcctgtgtc tctgtgatgg caacagaagg | 120 |
| accaacaggc cacatcctga taaaaggtaa gagggggtg gatcagcaaa aagacagtgc | 180 |
| tgtgggctga ggggacctgg ttcttgtgtg ttgcccctca ggactcttcc cctacaaata | 240 |
| actttcatat gttcaaatcc catggaggag tgtttcatcc tagaaactcc catgcaagag | 300 |
| ctacattaaa cgaagctgca ggttaagggg cttanagatg ggaaaccagg tgactgagtt | 360 |
| tattcagctc ccaaaaaccc ttctctaggt gtgtctcaac taggaggcta gctgttaacc | 420 |
| ctgagcctgg gtaatccacc tgcagagtcc ccgcattcca gtgcatggaa cccttctggc | 480 |
| ctccctgtat aagtccagac tgaaaccccc ttggaaggnc tccagtcagg cagccctana | 540 |
| aactggggaa aaagaaaag gacgccccan ccccagctg tgcanctacg cacctcaaca | 600 |
| gcacagggtg gcagcaaaaa aaccacttta ctttggcaca acaaaaact nggggggca | 660 |
| accccggcac cccnangggg gttaacagga ancgggnaa cntggaaccc aattnaggca | 720 |
| ggcccnccac cccnaatntt gctgggaaat ttttcctccc ctaaattntt tc | 772 |

```
<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12
```

| | |
|---|---:|
| gccccaattc cagctgccac accacccacg gtgactgcat tagttcggat gtcatacaaa | 60 |
| agctgattga agcaaccctc tacttttgg tcgtgagcct tttgcttggt gcaggtttca | 120 |
| ttggctgtgt tggtgacgtt gtcattgcaa cagaatgggg gaaaggcact gttctctttg | 180 |
| aagtanggtg agtcctcaaa atccgtatag ttggtgaagc cacagcactt gagcccttc | 240 |
| atggtggtgt tccacacttg agtgaagtct tcctgggaac cataatcttt cttgatggca | 300 |
| ggcactacca gcaacgtcag ggaagtgctc agccattgtg gtgtacacca aggcgaccac | 360 |
| agcagctgcn acctcagcaa tgaagatgan gaggangatg aagaagaacg tcncgagggc | 420 |
| acacttgctc tcagtcttan caccatanca gcccntgaaa accaananca aagaccacna | 480 |
| cnccggctgc gatgaagaaa tnaccccncg ttgacaaact tgcatggcac tgggancca | 540 |

```
agtggcccna aaaatcttca aaaaggatgc cccatcnatt gacccccaa atgcccactg      600 ccaacagggg ctgccccacn cncnnaacga tganccnatt gnacaagatc tncntggtct     660
tnatnaacnt gaaccctgcn tngtggctcc tgttcaggnc cnnggctga cttctnaann     720 aangaactcn gaagncccca cnggananc g                                     751
```

```
<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13
gagccaggcg tccctctgcc tgcccactca gtggcaacac ccgggagctg ttttgtcctt      60
tgtggancct cagcagtncc ctctttcaga actcantgcc aagancccctg aacaggagcc    120 accatgcagt gcttcagctt cattaagacc atgatgatcc tcttcaattt gctcatcttt     180
ctgtgtggtg cagccctgtt ggcagtgggc atctgggtgt caatcgatgg ggcatccttt     240
ctgaagatct tcgggccact gtcgtccagt gccatgcagt ttgtcaacgt gggctacttc     300
ctcatcgcag ccggcgttgt ggtcttagct ctaggtttcc tgggctgcta tggtgctaag     360
actgagagca gtgtgccct cgtgacgttc ttcttcatcc cctcctcat cttcattgct      420 gaggttgcaa tgctgtggtc gccttggtgt acaccacaat ggctgagcac ttcctgacgt     480
tgctggtaat gcctgccatc aanaaaagat tatgggttcc caggaanact tcactcaagt     540
gttggaacac caccatgaaa gggctcaagt gctgtggctt cnnccaacta tacggatttt    600
gaagantcac ctacttcaaa gaaaanagtg cctttcccc atttctgttg caattgacaa     660
acgtccccaa cacagccaat tgaaaacctg cacccaaccc aaagggtcc ccaaccanaa     720 attnaaggg                                                             729
```

```
<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14
tgctcttcct caaagttgtt cttgttgcca taacaaccac cataggtaaa gcgggcgcag      60
tgttcgctga aggggttgta gtaccagcgc gggatgctct ccttgcagag tcctgtgtct    120
ggcaggtcca cgcagtgccc tttgtcactg gggaaatgga tgcgctggag ctcgtcaaag    180
ccactcgtgt atttttcaca ggcagcctcg tccgacgcgt cggggcagtt ggggggtgtct    240 tcacactcca ggaaactgtc natgcagcag ccattgctgc agcggaactg ggtgggctga    300
cangtgccag agcacactgg atggcgcctt tccatgnnan gggccctgng ggaaagtccc    360 tgancccan anctgcctct caaangcccc accttgcaca ccccgacagg ctagaatgga    420
atcttcttcc cgaaaggtag ttnttcttgt tgcccaancc anccccntaa acaaactctt   480
gcanatctgc tccgnggggg tcntantacc ancgtgggaa aagaaccca ggcngcgaac    540 caancttgtt tggatncgaa gcnataatct nctnttctgc ttggtggaca gcaccantna   600
```

| | |
|---|---|
| ctgtnnanct ttagnccntg gtcctcntgg gttgnncttg aacctaatcn ccnntcaact | 660 |
| gggacaaggt aantngccnt cctttnaatt cccnancntn ccccctggtt tggggttttn | 720 |
| cncnctccta ccccagaaan nccgtgttcc cccccaacta ggggccnaaa ccnnttnttc | 780 |
| cacaaccctn ccccacccac gggttcngnt ggttng | 816 |

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15

| | |
|---|---|
| ccaaggcctg ggcaggcata nacttgaagg tacaacccca ggaacccctg gtgctgaagg | 60 |
| atgtggaaaa cacagattgg cgcctactgc ggggtgacac ggatgtcagg gtagagagga | 120 |
| aagacccaaa ccaggtggaa ctgtggggac tcaaggaang cacctacctg ttccagctga | 180 |
| cagtgactag ctcagaccac ccagaggaca cggccaacgt cacagtcact gtgctgtcca | 240 |
| ccaagcagac agaagactac tgcctcgcat ccaacaangt gggtcgctgc cggggctctt | 300 |
| tcccacgctg gtactatgac cccacggagc agatctgcaa gagtttcgtt tatggaggct | 360 |
| gcttgggcaa caagaacaac taccttcggg aagaagagtg cattctancc tgtcngggtg | 420 |
| tgcaaggtgg gcctttgana ngcanctctg ggctcangc gactttcccc cagggcccct | 480 |
| ccatggaaag gcgccatcca ntgttctctg gcacctgtca gcccacccag ttccgctgca | 540 |
| ncaatggctg ctgcatcnac antttcctng aattgtgaca acaccccca ntgcccccaa | 600 |
| ccctcccaac aaagcttccc tgttnaaaaa tacnccantt ggcttttnac aaacncccgg | 660 |
| cncctccntt ttccccnntn aacaaagggc nctngcnttt gaactgcccn aacccnggaa | 720 |
| tctnccnngg aaaaantncc ccccctggtt cctnnaancc cctccncnaa anctnccccc | 780 |
| ccc | 783 |

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16

| | |
|---|---|
| gccccaattc cagctgccac accacccacg gtgactgcat tagttcggat gtcatacaaa | 60 |
| agctgattga agcaaccctc tactttttgg tcgtgagcct tttgcttggt gcaggtttca | 120 |
| ttggctgtgt tggtgacgtt gtcattgcaa cagaatgggg gaaaggcact gttctctttg | 180 |
| aagtagggtg agtcctcaaa atccgtatag ttggtgaagc cacagcactt gagcccttte | 240 |
| atggtggtgt tccacacttg agtgaagtct tcctgggaac cataatcttt cttgatggca | 300 |
| ggcactacca gcaacgtcag gaagtgctca gccattgtgg tgtacaccaa ggcgaccaca | 360 |
| gcagctgcaa cctcagcaat gaagatgagg aggaggatga agaagaacgt cncgagggca | 420 |
| cacttgctct ccgtcttagc accatagcag cccangaaac caagagcaaa gaccacaacg | 480 |
| ccngctgcga atgaaagaaa ntacccacgt tgacaaactg catggccact ggacgacagt | 540 |
| tggcccgaan atcttcagaa aagggatgcc ccatcgattg aacacccana tgcccactgc | 600 |

| | |
|---|---|
| cnacagggct gcnccncncn gaaagaatga gccattgaag aaggatcntc ntggtcttaa | 660 |
| tgaactgaaa ccntgcatgg tggcccctgt tcagggctct tggcagtgaa ttctganaaa | 720 |
| aaggaacngc ntnagcccc ccaaangana aacacccc gggtgttgcc ctgaattggc | 780 |
| ggccaaggan ccctgccccn g | 801 |

<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17

| | |
|---|---|
| gtgagagcca ggcgtccctc tgcctgccca ctcagtggca cacccggga gctgttttgt | 60 |
| cctttgtgga gcctcagcag ttccctcttt cagaactcac tgccaagagc cctgaacagg | 120 |
| agccaccatg cagtgcttca gcttcattaa gaccatgatg atcctcttca atttgctcat | 180 |
| ctttctgtgt ggtgcagccc tgttggcagt gggcatctgg gtgtcaatcg atgggcatc | 240 |
| ctttctgaag atcttcgggc cactgtcgtc cagtgccatg cagtttgtca cgtgggcta | 300 |
| cttcctcatc gcagccggcg ttgtggtctt tgctcttggt ttcctgggct gctatggtgc | 360 |
| taagacggag agcaagtgtg ccctcgtgac gttcttcttc atcctcctcc tcatcttcat | 420 |
| tgctgaagtt gcagctgctg tggtcgcctt ggtgtacacc acaatggctg aaccattcct | 480 |
| gacgttgctg gtantgcctg ccatcaanaa agattatggg ttcccaggaa aaattcactc | 540 |
| aantntggaa caccnccatg aaaagggctc caatttctgn tggcttcccc aactataccg | 600 |
| gaattttgaa agantcnccc tacttccaaa aaaaaanant tgcctttncc cccnttctgt | 660 |
| tgcaatgaaa acntcccaan acngccaatn aaaacctgcc cnnncaaaaa ggntcncaaa | 720 |
| caaaaaaant nnaagggttn | 740 |

<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

| | |
|---|---|
| ccgctggttg cgctggtcca gngnagccac gaagcacgtc agcatacaca gcctcaatca | 60 |
| caaggtcttc cagctgccgc acattacgca gggcaagagc ctccagcaac actgcatatg | 120 |
| ggatacactt tactttagca gccagggtga caactgagag gtgtcgaagc ttattcttct | 180 |
| gagcctctgt tagtggagga agattccggg cttcagctaa gtagtcagcg tatgtcccat | 240 |
| aagcaaacac tgtgagcagc cggaaggtag aggcaaagtc actctcagcc agctctctaa | 300 |
| cattgggcat gtccagcagt tctccaaaca cgtagacacc agnggcctcc agcacctgat | 360 |
| ggatgagtgt ggccagcgct gcccccttgg ccgacttggc taggagcaga aattgctcct | 420 |
| ggttctgccc tgtcaccttc acttccgcac tcatcactgc actgagtgtg ggggacttgg | 480 |
| gctcaggatg tccagagacg tggttccgcc ccctcnctta atgacaccgn ccanncaacc | 540 |
| gtcggctccc gccgantgng ttcgtcgtnc ctgggtcagg gtctgctggc cnctacttgc | 600 |

| | |
|---|---|
| aancttcgtc nggcccatgg aattcaccnc accggaactn gtangatcca ctnnttctat | 660 |
| aaccggncgc caccgcnnnt ggaactccac tcttnttncc tttacttgag ggttaaggtc | 720 |
| acccttnncg ttaccttggt ccaaaccntn cntgtgtcg anatngtnaa tcnggnccna | 780 |
| tnccanccnc atangaagcc ng | 802 |

```
<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19
```

| | |
|---|---|
| cnaagcttcc aggtnacggg ccgcnaancc tgacccnagg tancanaang cagncgcgg | 60 |
| gagcccaccg tcacgnggng gngtctttat nggagggggc ggagccacat cnctggacnt | 120 |
| cntgaccccca actccccncc ncncantgca gtgatgagtg cagaactgaa ggtnacgtgg | 180 |
| caggaaccaa gancaaannc tgctccnntc caagtcggcn naggggggcgg ggctggccac | 240 |
| gcncatcct cnagtgctgn aaagccccnn cctgtctact tgtttggaga acngcnnnga | 300 |
| catgcccagn gttanataac nggcngagag tnantttgcc tctccttcc ggctgcgcan | 360 |
| cgngtntgct tagnggacat aacctgacta cttaactgaa cccnngaatc tnccncccct | 420 |
| ccactaagct cagaacaaaa aacttcgaca ccactcantt gtcacctgnc tgctcaagta | 480 |
| aagtgtaccc catncccaat gtntgctnga ngctctgncc tgcnttangt tcggtcctgg | 540 |
| gaagacctat caattnaagc tatgtttctg actgcctctt gctccctgna acaancnacc | 600 |
| cnncnntcca agggggggnc ggcccccaat cccccaacc ntnaattnan tttanccccn | 660 |
| cccccnggcc cggccttta cnancntcnn nnacngggna aaaccnnngc tttncccaac | 720 |
| nnaatccncc t | 731 |

```
<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20
```

| | |
|---|---|
| ttttttttt tttttttttt taaaaacccc ctccattnaa tgnaaacttc cgaaattgtc | 60 |
| caacccctc ntccaaatnn ccntttccgg gnggggttc caaacccaan ttanntttgg | 120 |
| annttaaatt aaatnttnnt tggnggnnna anccnaatgt nangaaagtt naacccanta | 180 |
| tnacttnaa tncctggaaa ccngtngntt ccaaaaatnt ttaaccctta antccctccg | 240 |
| aaatngttna nggaaaaccc aanttctcnt aaggttgttt gaaggntnaa tnaaaanccc | 300 |
| nnccaattgt ttttngccac gcctgaatta attggnttcc gntgttttcc nttaaaanaa | 360 |
| ggnnancccc ggttantnaa tcccccnnc cccaattata ccganttttt ttngaattgg | 420 |
| ganccncgg gaattaacgg ggnnnntccc tnttgggggg cnggnncccc cccntcggg | 480 |
| ggttngggnc aggncnnaat tgtttaaggg tccgaaaaat ccctccnaga aaaaaanctc | 540 |
| ccaggntgag nntggggttt nccccccccc canggccct ctcgnanagt tggggtttgg | 600 |
| ggggcctggg attttnttc ccctnttncc tcccccccc ccnggganag aggttngngt | 660 |

```
tttgntcnnc ggccccnccn aaganctttn ccganttnan ttaaatccnt gcctnggcga    720
agtccnttgn agggntaaan ggcccccctnn cggg                              754
```

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21

```
atcancccat gaccccnaac nngggaccnc tcanccggnc nnncnaccnc cggccnatca     60
nngtnagnnc actncnnttn natcacnccc cnccnactac gcccncnanc cnacgcncta    120
nncanatncc actganngcg cgangtngan ngagaaanct nataccanag ncaccanacn    180
ccagctgtcc nanaangcct nnnatacngg nnnatccaat ntgnaccctc cnaagtattn    240
nncnncanat gattttcctn anccgattac ccntncccccc tanccctcc ccccaacna    300 cgaaggcnct ggnccnaagg nngcgncncc ccgctagntc cccnncaagt cncncnccta    360
aactcanccn nattacncgc ttcntgagta tcactcccccg aatctcaccc tactcaactc    420
aaaaanatcn gatacaaaat aatncaagcc tgnttatnac actntgactg ggtctctatt    480
ttagnggtcc ntnaancntc ctaatacttc cagtctncct tcnccaattt ccnaanggct    540
ctttcngaca gcatnttttg gttcccnntt gggttcttan ngaattgccc ttcntngaac    600
gggctcntct tttccttcgg ttancctggn ttcnnccggc cagttattat ttcccnttttt    660 aaattcntnc cntttanttt tggcnttcna aaccccccggc cttgaaaacg gcccctggt    720 aaaaggttgt tttganaaaa tttttgtttt gttcc                              755
```

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22

```
tttttttttt ttttangtg tngtcgtgca ggtagaggct tactacaant gtgaanacgt     60
acgctnggan taangcgacc cganttctag ganncnccct aaaatcanac tgtgaagatn    120
atcctgnnna cggaanggtc accggnngat nntgctaggg tgnccnctcc cannncnttn    180
cataactcng nggccctgcc caccaccttc ggcgccccng ngnccgggcc cgggtcattn    240
gnnttaaccn cactnngcna ncggtttccn ncccccnncg acccnggcga tccggggtnc    300
tctgtcttcc cctgnagncn anaaantggg ccncggnccc ctttacccct nnacaagcca    360
cngccntcta nccncngccc ccctccant nnggggact gccnanngct ccgttnctng    420
nnaccccnnn gggtncctcg gttgtcgant cnaccgnang ccanggattc cnaaggaagg    480
tgcgttnttg gccctaccc ttcgctncgg nncaccccttc ccgacnanga nccgctcccg    540
cncnncgnng cctncctcg caacacccgc nctcntcngt ncggnnnccc ccccacccgc    600
nccctcncnc ngncgnancn ctccnccncc gtctcannca ccaccccgcc ccgccaggcc    660
ntcanccacn ggnngacnng nagcncnntc gcnccgcgcn gcgncnccct cgccncngaa    720
```

```
ctncntcngg ccantnncgc tcaanccnna cnaaacgccg ctgcgcggcc cgnagcgncc    780
ncctccncga gtcctcccgn cttccnaccc angnnttccn cgaggacacn nnaccccgcc    840 nncangcgg                                                            849
```

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23

```
gcgcaaacta tacttcgctc gnactcgtgc gcctcgctnc tcttttcctc cgcaaccatg     60
tctgacnanc ccgattnggc ngatatcnan aagntcganc agtccaaact gantaacaca    120
cacacncnan aganaaatcc nctgccttcc anagtanacn attgaacnng agaaccangc    180
nggcgaatcg taataaggcg tgcgccgcca atntgtcncc gtttattntn ccagcntcnc    240
ctnccnaccc tacntcttcn nagctgtcnn acccctngtn cgnaccccc naggtcggga     300 tcgggtttnn nntgaccgng cnnccctcc cccntccat nacgancnc ccgcaccacc      360 nanngcncgc ncccgnnct cttcgccncc ctgtcctntn cccctgtngc ctggcncngn    420
accgcattga ccctcgccnn ctncnngaaa ncgnanacgt ccgggttgnn annancgctg    480
tgggnnngcg tctgcnccgc gttccttccn ncnncttcca ccatcttcnt tacngggtct    540
ccncgccntc tcnnncacnc cctgggacgc tntcctntgc cccccttnac tcccccccctt   600 cgncgtgncc cgncccacc ntcatttnca nacgntcttc acaannncct ggntnncctcc   660 cnancngncn gtcanccnag ggaagggngg ggnnccnntg nttgacgttg ngngangtc    720 cgaanantcc tcncntcan cnctacccct cgggcgnnct ctcgttncc aacttancaa     780 ntctccccg ngngcncntc tcagcctcnc ccnccccnct ctctgcantg tnctctgctc    840
tnaccnntac gantnttcgn cnccctcttt cc                                  872
```

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24

```
gcatgcaagc ttgagtattc tatagngtca cctaaatanc ttggcntaat catggtcnta     60
nctgncttcc tgtgtcaaat gtatacnaan tanatatgaa tctnatntga caagannngta  120 tcntncatta gtaacaantg tnntgtccat cctgtcngan canattccca tnnattncgn    180
cgcattcncn gcncantatn taatngggaa ntcnnntnnn ncaccnncat ctatcntncc    240
gcnccctgac tggnagagat ggatnanttc tnntntgacc nacatgttca tcttggattn    300 aanancccc cgcngnccac cggttngnng cnagccnntc ccaagacctc ctgtggaggt    360
aacctgcgtc aganncatca aacntgggaa acccgcnncc angtnnaagt ngnnncanan   420
gatcccgtcc aggnttnacc atccttcnc agcgccccct ttngtgcctt anagngnagc    480
gtgtccnanc cnctcaacat ganacgcgcc agnccanccg caattnggca caatgtcgnc    540
gaacccccta gggggantna tncaaancccc caggattgtc cncncangaa atcccncanc   600
```

| | |
|---|---:|
| cccnccctac ccnnctttgg dacngtgacc aantcccgga gtnccagtcc ggccngnctc | 660 |
| ccccaccggt nnccntgggg gggtgaanct cngnntcanc cngncgaggn ntcgnaagga | 720 |
| accggncctn ggncgaanng ancnntcnga agngccncnt cgtataaccc ccctcncca | 780 |
| nccacngnt agntccccc cngggtncgg aangg | 815 |

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

| | |
|---|---:|
| ccgagatgtc tcgctccgtg gccttagctg tgctcgcgct actctctctt tctggcctgg | 60 |
| aggctatcca gcgtactcca aagattcagg tttactcacg tcatccagca gagaatggaa | 120 |
| agtcaaattt cctgaattgc tatgtgtctg ggtttcatcc atccgacatt gaanttgact | 180 |
| tactgaagaa tgganagaga attgaaaaag tggagcattc agacttgtct ttcagcaagg | 240 |
| actggtcttt ctatctcntg tactacactg aattcacccc cactgaaaaa gatgagtatg | 300 |
| cctgccgtgt gaaccatgtg actttgtcac agcccaagat agttaagtgg gatcgagaca | 360 |
| tgtaagcagn cnncatggaa gtttgaagat gccgcatttg gattggatga attccaaatt | 420 |
| ctgcttgctt gcnttttaat antgatatgc ntatacaccc taccctttat gncccccaaat | 480 |
| tgtagggggtt acatnantgt tcncntngga catgatcttc ctttataant ccnccnttcg | 540 |
| aattgcccgt cncccngttn ngaatgtttc cnnaaccacg gttggctccc ccaggtcncc | 600 |
| tcttacggaa gggcctgggc cnctttncaa ggttgggga accnaaaatt tcncttntgc | 660 |
| ccncccncca cnntcttgng nncncanttt ggaacccttc cnattcccct tggcctcnna | 720 |
| nccttnncta anaaaacttn aaancgtngc naaannttn acttcccccc ttacc | 775 |

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26

| | |
|---|---:|
| anattantac agtgtaatct tttcccagag gtgtgtanag ggaacggggc ctagaggcat | 60 |
| cccanagata ncttatanca acagtgcttt gaccaagagc tgctgggcac atttcctgca | 120 |
| gaaaaggtgg cggtccccat cactcctcct ctcccatagc catcccagag gggtgagtag | 180 |
| ccatcangcc ttcggtggga gggagtcang gaaacaacan accacagagc anacagacca | 240 |
| ntgatgacca tgggcgggag cgagcctctt ccctgnaccg gggtggcana nganagccta | 300 |
| nctgagggt cacactataa acgttaacga ccnagatnan cacctgcttc aagtgcaccc | 360 |
| ttcctacctg acnaccagng accnnnaact gcngcctggg dacagcnctg ggancagcta | 420 |
| acnnagcact cacctgcccc ccatggccg tncgcntccc tggtcctgnc aagggaagct | 480 |
| ccctgttgga attncgggga naccaaggga nccccctcct ccanctgtga aggaaaaann | 540 |
| gatggaattt tncccttccg gccnntcccc tcttccttta cacgccccct nntactcntc | 600 |

| | | | | |
|---|---|---|---|---|
| tccctctntt | ntcctgncnc | acttttnacc | ccnnnatttc | ccttnattga tcggannctn | 660 |
| ganattccac | tnncgcctnc | cntcnatcng | naanacnaaa | nactntctna cccnggggat | 720 |
| gggnncctcg | ntcatcctct | cttttcnct | accnccnntt | ctttgcctct ccttngatca | 780 |
| tccaaccntc | gntggccntn | cccccccnnn | tcctttnccc | | 820 |

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27

| | | | | |
|---|---|---|---|---|
| tctgggtgat | ggcctcttcc | tcctcaggga | cctctgactg | ctctgggcca aagaatctct | 60 |
| tgtttcttct | ccgagcccca | ggcagcggtg | attcagccct | gcccaacctg attctgatga | 120 |
| ctgcggatgc | tgtgacggac | ccaagggca | aatagggtcc | cagggtccag ggaggggcgc | 180 |
| ctgctgagca | cttccgcccc | tcaccctgcc | cagcccctgc | catgagctct gggctgggtc | 240 |
| tccgcctcca | gggttctgct | cttccangca | ngccancaag | tggcgctggg ccacactggc | 300 |
| ttcttcctgc | cccntccctg | gctctgantc | tctgtcttcc | tgtcctgtgc angcnccttg | 360 |
| gatctcagtt | tccctcnctc | anngaactct | gtttctgann | tcttcantta actntganttt | 420 |
| tatnaccnan | tggnctgtnc | tgtcnnactt | taatgggccn | gaccggctaa tccctcccctc | 480 |
| nctcccttcc | anttcnnnna | accngcttnc | cntcntctcc | ccntancccg ccngggaanc | 540 |
| ctcctttgcc | ctnaccangg | gccnnnaccg | cccntnnctn | gggggcnng gtnnctncnc | 600 |
| ctgntnnccc | cnctcncnnt | tncctcgtcc | cnncnncgcn | nngcannttc ncgtcccnn | 660 |
| tnnctcttcn | ngtntcgnaa | ngtcncntn | tnnnngncn | ngntnntncn tccctctcnc | 720 |
| cnnntgnang | tnnttnnnnc | ncngnnccc | nnnncnnnn | nggnnntnnn tctncncngc | 780 |
| cccnnccccc | ngnattaagg | cctccnntct | ccggccnc | | 818 |

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28

| | | | | |
|---|---|---|---|---|
| aggaagggcg | gagggatatt | gtangggatt | gagggatagg | agnataangg gggaggtgtg | 60 |
| tcccaacatg | anggtgnngt | tctcttttga | angagggttg | ngtttttann ccnggtgggt | 120 |
| gattnaaccc | cattgtatgg | agnnaaaggn | tttnagggat | ttttcggctc ttatcagtat | 180 |
| ntanattcct | gtnaatcgga | aaatnatntt | tcnncnggaa | aatnttgctc ccatccgnaa | 240 |
| attnctcccg | ggtagtgcat | nttngggggn | cngccangtt | tcccaggctg ctanaatcgt | 300 |
| actaaagntt | naagtgggan | tncaaatgaa | aacctnncac | agagnatccn tacccgactg | 360 |
| tnnnttncct | tcgccctntg | actctgcnng | agcccaatac | ccnngngnat gtcnccngn | 420 |
| nnngcgncnc | tgaaannnnc | tcgnggctnn | gancatcang | gggtttcgca tcaaaagcnn | 480 |
| cgtttcncat | naaggcactt | tngcctcatc | caacncntg | ccctcnncca tttngccgtc | 540 |
| nggttcnnct | acgctnnntg | cnccntnnntn | ganattttnc | ccgcctnggg naancctcct | 600 |

```
gnaatgggta gggncttntc ttttnaccnn gnggtntact aatcnnctnc acgcntnctt    660
tctcnacccc ccccttttt caatcccanc ggcnaatggg gtctccccnn cganggggggg    720 nnncccannc c                                                         731
```

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

```
actagtccag tgtggtggaa ttccattgtg ttggggncnc ttctatgant antnttagat     60
cgctcanacc tcacanccctc ccacnangc ctataangaa nannaataga nctgtncnnt    120
atntntacnc tcatanncct cnnnacccac tccctcttaa cccntactgt gcctatngcn    180
tnnctantct ntgccgcctn cnaccaccn gtgggccnac cncnngnatt ctcnatctcc     240
tcnccatntn gcctananta ngtncatacc ctatacctac nccaatgcta nnnctaancn    300
tccatnantt annntaacta ccactgacnt ngactttcnc atnanctcct aatttgaatc    360
tactctgact cccacngcct annnattagc ancntccccc nacnatntct caaccaaatc    420
ntcaacaacc tatctanctg ttcnccaacc nttncctccg atccccnnac aaccccccctc    480 ccaaatacccc nccacctgac ncctaacccn caccatcccg gcaagccnan ggncatttan    540
ccactggaat cacnatngga naaaaaaaac ccnaactctc tancncnnat ctccctaana    600
aatnctcctn naatttactn ncantnccat caancccacn tgaaacnnaa cccctgtttt    660
tanatccctt ctttcgaaaa ccnacccttt annncccaac ctttngggcc ccccncctnc    720
ccnaatgaag gncncccaat cnangaaacg nccntgaaaa ancnaggcna anannntccg    780
canatcctat cccttantt ngggncccctt ncccngggcc cc                       822
```

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

```
cggccgcctg ctctggcaca tgcctcctga atggcatcaa aagtgatgga ctgcccattg     60
ctagagaaga ccttctctcc tactgtcatt atggagccct gcagactgag ggctccccctt   120 gtctgcagga tttgatgtct gaagtcgtgg agtgtggctt ggagctcctc atctacatna   180
gctggaagcc ctggagggcc tctctcgcca gcctccccct tctctccacg ctctccangg   240
acaccagggg ctccaggcag cccattattc ccagnangac atggtgtttc tccacgcgga   300 cccatgggc ctgnaaggcc agggtctcct ttgacaccat ctctcccgtc ctgcctggca   360
ggccgtggga tccactantt ctanaacggn cgccaccncg gtgggagctc cagcttttgt   420
tcccnttaat gaaggttaat tgcncgcttg gcgtaatcat nggtcanaac tntttcctgt   480
gtgaaattgt ttntccccctc ncnattccnc ncnacatacn aacccggaan cataaagtgt   540
taaagcctgg gggtngcctn nngaatnaac tnaactcaat taattgcgtt ggctcatggc   600
```

```
ccgctttccn ttcnggaaaa ctgtcntccc ctgcnttnnt gaatcggcca cccccnggg      660 aaaagcggtt tgcnttttng ggggntcctt ccncttcccc cctcnctaan ccctncgcct     720
cggtcgttnc nggtngcggg gaangggnat nnnctcccnc naaggggng agnnngntat      780 ccccaaa                                                              787

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31 ttttttttttt tttttttggc gatgctactg tttaattgca ggaggtgggg gtgtgtgtac     60
catgtaccag ggctattaga agcaagaagg aaggaggag ggcagagcgc cctgctgagc     120
aacaaaggac tcctgcagcc ttctctgtct gtctcttggc gcaggcacat ggggaggcct    180 cccgcaggt gggggccacc agtccagggg tgggagcact acanggggtg ggagtgggtg     240
gtggctggtn cnaatggcct gncacanatc cctacgattc ttgacacctg gatttcacca    300
ggggaccttc tgttctccca nggnaacttc ntnnatctcn aaagaacaca actgtttctt    360
cngcanttct ggctgttcat ggaaagcaca ggtgtccnat ttnggctggg acttggtaca    420
tatggttccg gcccacctct cccntcnaan aagtaattca cccccccccn ccntctnttg    480
cctgggccct taantaccca caccggaact canttantta ttcatcttng gntgggcttg    540
ntnatcnccn cctgaangcg ccaagttgaa aggccacgcc gtncccnctc cccatagnan    600
nttttnncnt canctaatgc cccccncggc aacnatccaa tccccccccn tggggcccc    660 agcccanggc ccccgnctcg ggnnncnngn cncgnantcc ccaggntctc ccantcngnc    720
ccnnngcncc cccgcacgca gaacanaagg ntngagccnc cgcannnnnn nggtnncnac    780 ctcgccccc ccnncgnng                                                 799

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32
tttttttttt tttttttttt tttttttttt tttttttttt tttttttttt tttttttttt     60
ttttnccnag ggcaggttta ttgacaacct cncgggacac aancaggctg gggacaggac    120
ggcaacaggc tccggcggcg gcggcggcgg ccctacctgc ggtaccaaat ntgcagcctc    180
cgctcccgct tgatnttcct ctgcagctgc aggatgccnt aaaacagggc ctcggccntn    240
ggtgggcacc ctgggatttn aatttccacg ggcacaatgc ggtcgcancc cctcaccacc    300
nattaggaat agtggtnntta cccncncncg ttggcncact cccntggaa accacttntc    360 gcggctccgg catctggtct taaaccttgc aaacnctggg gccctctttt tggttantnt    420
nccngccaca atcatnactc agactggcnc gggctggccc caaaaaancn ccccaaaacc    480
ggnccatgtc ttnncggggt tgctgcnatn tncatcacct cccgggcnca ncaggncaac    540
ccaaaagttc ttgnggcccn caaaaaanct ccgggggngnc ccagtttcaa caaagtcatc    600
```

```
cccettggcc cccaaatcct cccccegntt nctgggtttg ggaacccacg cctctnnctt      660
tggnnggcaa gntggntccc ccttcgggcc ccggtgggc ccnnctctaa ngaaaacncc       720
ntcctnnnca ccatccccc nngnnacgnc tancaangna tccctttttt tanaaacggg      780 ccccccncg                                                             789
```

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33

```
gacagaacat gttggatggt ggagcacctt tctatacgac ttacaggaca gcagatgggg     60
aattcatggc tgttggagca atanaacccc agttctacga gctgctgatc aaaggacttg    120
gactaaagtc tgatgaactt cccaatcaga tgagcatgga tgattggcca gaaatgaana   180
agaagtttgc agatgtattt gcaaagaaga cgaaggcaga gtggtgtcaa atctttgacg    240
gcacagatgc ctgtgtgact ccggttctga cttttgagga ggttgttcat catgatcaca    300
acaangaacg gggctcgttt atcaccantg aggagcagga cgtgagcccc cgccctgcac    360
ctctgctgtt aaacaccca gccatccctt ctttcaaaag ggatccacta cttctagagc     420
ggncgccacc gcggtggagc tccagctttt gttccctta gtgagggtta attgcgcgct    480
tggcgtaatc atggtcatan ctgtttcctg tgtgaaattg ttatccgctc acaattccac    540
acaacatacg anccggaagc atnaaatttt aaagcctggn ggtngcctaa tgantgaact    600
nactcacatt aattggcttt gcgctcactg cccgctttcc agtccggaaa acctgtcctt    660
gccagctgcc nttaatgaat cnggccaccc cccggggaaa aggcngtttg cttnttgggg   720 cgcnttccc gctttctcgc ttcctgaant ccttcccccc ggtctttcgg cttgcggcna    780
acggtatcna cct                                                       793
```

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34

```
gccgcgaccg gcatgtacga gcaactcaag ggcgagtgga accgtaaaag ccccaatctt     60
ancaagtgcg gggaanagct gggtcgactc aagctagttc ttctggagct caacttcttg    120
ccaaccacag ggaccaagct gaccaaacag cagctaattc tggcccgtga catactggag    180
atcggggccc aatggagcat cctacgcaan gacatcccct ccttcgagcg ctacatggcc    240
cagctcaaat gctactactt tgattacaan gagcagctcc ccgagtcagc ctatatgcac    300
cagctcttgg gcctcaacct cctcttcctg ctgtcccaga accgggtggc tgantnccac    360
acgganttgg ancggctgcc tgcccaanga catacanacc aatgtctaca tcnaccacca    420
gtgtcctgga gcaatactga tggnggcag ctaccncaaa gtnttcctgg ccnagggtaa   480
catcccccgc cgagagctac accttcttca ttgacatcct gctcgacact atcagggatg    540
```

```
aaaatcgcng ggttgctcca gaaaggctnc aanaanatcc ttttcnctga aggcccccgg    600
atncnctagt nctagaatcg gcccgccatc gcggtgganc ctccaaccct tcgttncccct   660 ttactgaggg ttnattgccg cccttggcgt tatcatggtc acnccngttn cctgtgttga   720
aattnttaac cccccacaat tccacgccna cattng                             756
```

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35

```
ggggatctct anatcnacct gnatgcatgg ttgtcggtgt ggtcgctgtc gatgaaanatg    60 aacaggatct tgcccttgaa gctctcggct gctgtnttta agttgctcag tctgccgtca   120
tagtcagaca cnctcttggg caaaaaacan caggatntga gtcttgattt cacctccaat   180
aatcttcngg gctgtctgct cggtgaactc gatgacnang ggcagctggt tgtgtntgat   240
aaantccanc angttctcct tggtgacctc cccttcaaag ttgttccggc cttcatcaaa   300
cttctnnaan angannancc canctttgtc gagctggnat ttgganaaca cgtcactgtt   360
ggaaactgat cccaaatggt atgtcatcca tcgcctctgc tgcctgcaaa aaacttgctt    420
ggcncaaatc cgactcccn tccttgaaag aagcccatca caccccccctc cctggactcc   480 nncaangact ctnccgctnc cccntccnng cagggttggt ggcanncccgg gcccntgcgc   540 ttcttcagcc agttcacnat nttcatcagc ccctctgcca gctgttntat tccttggggg   600
ggaanccgtc tctcccttcc tgaannaact ttgaccgtng gaatagccgc gcntcnccnt   660
acntnctggg ccgggttcaa antccctcc ttgncnntcn cctcgggcca ttctggattt   720
nccnaacttt ttccttcccc cnccccncgg ngtttggntt tttcatnggg ccccaactct   780
gctnttggcc antcccctgg gggcntntan cncccccctnt ggtcccntng ggcc        834
```

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36

```
cggncgcttt ccngccgcgc cccgtttcca tgacnaaggc tcccttcang ttaaatacnn    60
cctagnaaac attaatgggt tgctctacta atacatcata cnaaccagta agcctgccca   120
naacgccaac tcaggccatt cctaccaaag gaagaaaggc tggtctctcc accccctgta   180
ggaaaggcct gccttgtaag acaccacaat ncggctgaat ctnaagtctt gtgttttact   240
aatggaaaaa aaaaataaac aanaggtttt gttctcatgg ctgcccaccg cagcctggca   300
ctaaaacanc ccagcgctca cttctgcttg ganaaatatt ctttgctctt ttggacatca   360
ggcttgatgg tatcactgcc acntttccac ccagctgggc ncccttcccc catntttgtc   420
antganctgg aaggcctgaa ncttagtctc caaaagtctc ngcccacaag accggccacc   480 agggganngtc ntttncagtg gatctgccaa anantacccn tatcatcnnt gaataaaaag   540
gcccctgaac ganatgcttc cancanccctt taagacccat aatcctngaa ccatggtgcc   600
```

```
cttccggtct gatccnaaag gaatgttcct gggtcccant ccctcctttg ttncttacgt      660
tgtnttggac ccntgctngn atnacccaan tganatcccc ngaagcaccc tnccctggc       720 atttganttt cntaaattct ctgccctacn nctgaaagca cnattccctn ggcnccnaan      780
ggngaactca agaaggtctn ngaaaaacca cncn                                  814
```

<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

```
gcatgctgct cttcctcaaa gttgttcttg ttgccataac aaccaccata ggtaaagcgg       60
gcgcagtgtt cgctgaaggg gttgtagtac cagcgcggga tgctctcctt gcagagtcct     120
gtgtctggca ggtccacgca atgcccttg tcactgggga aatggatgcg ctggagctcg      180
tcnaanccac tcgtgtattt tcacangca gcctcctccg aagcntccgg gcagttgggg      240
gtgtcgtcac actccactaa actgtcgatn cancagccca ttgctgcagc ggaactgggt     300
gggctgacag gtgccagaac acactggatn ggcctttcca tggaagggcc tgggggaaat     360
cncctnancc caaactgcct ctcaaaggcc accttgcaca cccgacagg ctagaaatgc      420 actcttcttc ccaaaggtag ttgttcttgt tgcccaagca ncctccanca aaccaaaanc     480
ttgcaaaatc tgctccgtgg gggtcatnnn taccanggtt ggggaaanaa accggcngn      540 ganccncctt gtttgaatgc naaggnaata atcctcctgt cttgcttggg tggaanagca     600
caattgaact gttaacnttg ggccngttc cnctngggtg gtctgaaact aatcaccgtc      660
actgaaaaaa ggtangtgcc ttccttgaat tcccaaantt cccctngntt tgggtnnttt     720
ctcctctncc ctaaaaatcg tnttcccccc ccntanggcg                            760
```

<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

```
tttttttttt tttttttttt tttttttttt ttttaaaaa ccccctccat tgaatgaaaa       60
cttccnaaat tgtccaaccc cctcnnccaa atnnccattt ccggggggggg gttccaaacc    120 caaattaatt ttgganttta aattaaatnt tnattngggg aanaanccaa atgtnaagaa     180
aatttaaccc attatnaact taaatnccctn gaaacccntg gnttccaaaa attttttaacc  240 cttaaatccc tccgaaattg ntaanggaaa accaaattcn cctaaggctn tttgaaggtt    300
ngatttaaac ccccttnant tnttttnacc cnngnctnaa ntatttngnt tccggtgttt    360 tcctntttaan cntnggtaac tcccgntaat gaannncccct aanccaatta aaccgaattt  420
tttttgaatt ggaaattccn ngggaattna ccggggtttt tccntttggg gggccatncc    480 cccncttcg gggtttgggn ntaggttgaa ttttnnang nccaaaaaa nccccccaana     540 aaaaaactcc caagnnttaa ttngaantc ccccttccca ggcctttgg gaaaggnggg     600
```

| | |
|---|---:|
| tttntggggg ccngggantt cnttccccn ttnccnccc cccccngt aaanggttat | 660 |
| ngnntttggt ttttgggccc cttnanggac cttccggatn gaaattaaat ccccgggncg | 720 |
| gccg | 724 |

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

| | |
|---|---:|
| tttttttttt ttttctttg ctcacattta atttttattt tgattttttt taatgctgca | 60 |
| caacacaata tttatttcat ttgtttcttt tatttcattt tatttgtttg ctgctgctgt | 120 |
| tttatttatt tttactgaaa gtgagaggga acttttgtgg cctttttcc tttttctgta | 180 |
| ggccgcctta agctttctaa atttggaaca tctaagcaag ctgaaggaa aaggggttt | 240 |
| cgcaaaatca ctcggggaa nggaaaggtt gctttgttaa tcatgccca tggtgggtga | 300 |
| ttaactgctt gtacaattac ntttcacttt taattaattg tgctnaangc tttaattana | 360 |
| cttgggggtt ccctccccan accaacccc ctgacaaaaa gtgccngccc tcaaatnatg | 420 |
| tcccggcnnt cnttgaaaca cacngcngaa ngttctcatt ntccccncnc caggtnaaaa | 480 |
| tgaagggtta ccatnttaa cnccacctcc acntggcnnn gcctgaatcc tcaaaaancn | 540 |
| ccctcaancn aattnctnng ccccggtcnc gcntnngtcc cncccgggct ccgggaantn | 600 |
| caccccnga anncnntnnc naacnaaatt ccgaaaatat tcccnntcnc tcaattcccc | 660 |
| cnnagactnt cctcnncnan cncaattttc ttttnntcac gaacncgnnc cnnaaaatgn | 720 |
| nnnncncctc cnctngtccn naatcnccan c | 751 |

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

| | |
|---|---:|
| gtggtatttt ctgtaagatc aggtgttcct ccctcgtagg tttagaggaa acaccctcat | 60 |
| agatgaaaac cccccgaga cagcagcact gcaactgcca agcagccggg gtaggagggg | 120 |
| cgccctatgc acagctgggc ccttgagaca gcagggcttc gatgtcaggc tcgatgtcaa | 180 |
| tggtctggaa gcggcggctg tacctgcgta ggggcacacc gtcagggccc accaggaact | 240 |
| tctcaaagtt ccaggcaacn tcgttgcgac acaccggaga ccaggtgatn agcttgggt | 300 |
| cggtcataan cgcggtggcg tcgtcgctgg gagctggcag ggcctcccgc aggaaggcna | 360 |
| ataaaaggtg cgccccgca ccgttcanct cgcacttctc naanaccatg angttgggct | 420 |
| cnaacccacc accanncgg acttccttga nggaattccc aaatctcttc gntcttgggc | 480 |
| ttctnctgat gccctanctg gttgcccngn atgccaanca nccccaancc ccgggtcct | 540 |
| aaancacccn cctcctcntt tcatctgggt tnttntcccc ggaccntggt tcctctcaag | 600 |
| ggancccata tctcnaccan tactcaccnt nccccccnt gnnaccancc cttctanngn | 660 |
| ttcccncccg ncctctggcc cntcaaanan gcttncacna cctgggtctg ccttccccc | 720 |

```
tnccctatct gnacccncn tttgtctcan tnt                              753
```

<210> SEQ ID NO 41
<211> LENGTH: 341
<212> TYPE: DNA
<213> ORGANISM: Homo sapien

<400> SEQUENCE: 41

```
actatatcca tcacaacaga catgcttcat cccatagact tcttgacata gcttcaaatg    60
agtgaaccca tccttgattt atatacatat atgttctcag tattttggga gcctttccac   120
ttctttaaac cttgttcatt atgaacactg aaaataggaa tttgtgaaga gttaaaaagt   180
tatagcttgt ttacgtagta agttttttgaa gtctacattc aatccagaca cttagttgag   240
tgttaaactg tgattttaa aaaatatcat ttgagaatat tctttcagag gtattttcat    300
ttttactttt tgattaattg tgttttatat attagggtag t                      341
```

<210> SEQ ID NO 42
<211> LENGTH: 101
<212> TYPE: DNA
<213> ORGANISM: Homo sapien

<400> SEQUENCE: 42

```
acttactgaa tttagttctg tgctcttcct tatttagtgt tgtatcataa atactttgat    60
gtttcaaaca ttctaaataa ataattttca gtggcttcat a                      101
```

<210> SEQ ID NO 43
<211> LENGTH: 305
<212> TYPE: DNA
<213> ORGANISM: Homo sapien

<400> SEQUENCE: 43

```
acatctttgt tacagtctaa gatgtgttct taaatcacca ttccttcctg gtcctcaccc    60
tccagggtgg tctcacactg taattagagc tattgaggag tctttacagc aaattaagat   120
tcagatgcct tgctaagtct agagttctag agttatgttt cagaaagtct aagaaaccca   180
cctcttgaga ggtcagtaaa gaggacttaa tatttcatat ctacaaaatg accacaggat   240
tggatacaga acgagagtta tcctggataa ctcagagctg agtacctgcc cggggggccgc   300
tcgaa                                                              305
```

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44

```
acataaatat cagagaaaag tagtctttga aatatttacg tccaggagtt ctttgtttct    60
gattatttgg tgtgtgtttt ggtttgtgtc caaagtattg gcagcttcag ttttcatttt   120
ctctccatcc tcgggcattc ttcccaaatt tatataccag tcttcgtcca tccacacgct   180
ccagaatttc tcttttgtag taatatctca tagctcggct gagcttttca taggtcatgc   240
tgctgttgtt cttcttttta ccccatagct gagccactgc ctctgatttc aagaacctga   300
agacgccctc agatcggtct tcccatttta ttaatcctgg gttcttgtct gggttcaaga   360
```

```
ggatgtcgcg gatgaattcc cataagtgag tccctctcgg gttgtgcttt ttggtgtggc      420
acttggcagg ggggtcttgc tccttttca tatcaggtga ctctgcaaca ggaaggtgac      480
tggtggttgt catggagatc tgagcccggc agaaagtttt gctgtccaac aaatctactg      540
tgctaccata gttggtgtca tataaatagt tctngtcttt ccaggtgttc atgatggaag      600
gctcagtttg ttcagtcttg acaatgacat tgtgtgtgga ctggaacagg tcactactgc      660
actggccgtt ccacttcaga tgctgcaagt tgctgtagag gagntgcccc gccgtccctg      720
ccgcccgggt gaactcctgc aaactcatgc tgcaaaggtg ctcgccgttg atgtcgaact      780
cntggaaagg gatacaattg gcatccagct ggttggtgtc caggaggtga tggagccact      840
cccacacctg gt                                                          852
```

```
<210> SEQ ID NO 45
<211> LENGTH: 234
<212> TYPE: DNA
<213> ORGANISM: Homo sapien

<400> SEQUENCE: 45
acaacagacc cttgctcgct aacgacctca tgctcatcaa gttggacgaa tccgtgtccg       60
agtctgacac catccggagc atcagcattg cttcgcagtg ccctaccgcg gggaactctt      120
gcctcgtttc tggctggggt ctgctggcga acggcagaat gcctaccgtg ctgcagtgcg      180
tgaacgtgtc ggtggtgtct gaggaggtct gcagtaagct ctatgacccg ctgt           234
```

```
<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46
actttttatt taaatgttta taaggcagat ctatgagaat gatagaaaac atggtgtgta       60
atttgatagc aatattttgg agattacaga gttttagtaa ttaccaatta cacagttaaa      120
aagaagataa tatattccaa gcanatacaa aatatctaat gaaagatcaa ggcaggaaaa      180
tgantataac taattgacaa tggaaaatca attttaatgt gaattgcaca ttatcccttta     240 aaagctttca aaanaaanaa ttattgcagt ctanttaatt caaacagtgt taaatggtat      300
caggataaan aactgaaggg canaaagaat taattttcac ttcatgtaac ncacccanat      360
ttacaatggc ttaaatgcan ggaaaaagca gtggaagtag ggaagtantc aaggtctttc      420
tggtctctaa tctgccttac tctttgggtg tggctttgat cctctggaga cagctgccag      480
ggctcctgtt atatccacaa tcccagcagc aagatgaagg gatgaaaaag gacacatgct      540
gccttccttt gaggagactt catctcactg gccaacactc agtcacatgt                590
```

```
<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47 acaaggggc ataatgaagg agtgggggana gattttaaag aaggaaaaaa aacgaggccc        60
```

```
tgaacagaat tttcctgnac aacgggctt caaaataatt ttcttgggga ggttcaagac      120
gcttcactgc ttgaaactta aatggatgtg ggacanaatt ttctgtaatg accctgaggg      180
cattacagac gggactctgg gaggaaggat aaacagaaag gggacaaagg ctaatcccaa      240
aacatcaaag aaaggaaggt ggcgtcatac ctcccagcct acacagttct ccagggctct      300
cctcatccct ggaggacgac agtggaggaa caactgacca tgtccccagg ctcctgtgtg      360
ctggctcctg gtcttcagcc cccagctctg gaagcccacc ctctgctgat cctgcgtggc      420
ccacactcct tgaacacaca tccccaggtt atattcctgg acatggctga acctcctatt      480
cctacttccg agatgccttg ctccctgcag cctgtcaaaa tcccactcac cctccaaacc      540
acggcatggg aagcctttct gacttgcctg attactccag catcttggaa caatccctga      600
ttccccactc cttagaggca agatagggtg gttaagagta gggctggacc acttggagcc      660
aggctgctgg cttcaaattn tggctcattt acgagctatg gaccttggg caagtnatct      720 tcacttctat gggcntcatt ttgttctacc tgcaaaatgg gggataataa tagt            774

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48
canaaattga aattttataa aaaggcattt ttctcttata tccataaaat gatataattt       60
ttgcaantat anaaatgtgt cataaattat aatgttcctt aattacagct caacgcaact      120
tggt                                                                   124

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49
gccgatgcta ctattttatt gcaggaggtg ggggtgtttt tattattctc tcaacagctt       60
tgtggctaca ggtggtgtct gactgcatna aaaantttt tacgggtgat tgcaaaaatt      120
ttagggcacc catatcccaa gcantgt                                          147

<210> SEQ ID NO 50
<211> LENGTH: 107
<212> TYPE: DNA
<213> ORGANISM: Homo sapien

<400> SEQUENCE: 50
acattaaatt aataaaagga ctgttggggt tctgctaaaa cacatggctt gatatattgc       60
atggtttgag gttaggagga gttaggcata tgttttggga gagggt                     107

<210> SEQ ID NO 51
<211> LENGTH: 204
<212> TYPE: DNA
<213> ORGANISM: Homo sapien
```

<400> SEQUENCE: 51

```
gtcctaggaa gtctagggga cacacgactc tggggtcacg gggccgacac acttgcacgg      60
cgggaaggaa aggcagagaa gtgacaccgt caggggaaa tgacagaaag gaaaatcaag      120
gccttgcaag gtcagaaagg ggactcaggg cttccaccac agccctgccc cacttggcca     180
cctccctttt gggaccagca atgt                                            204
```

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52

```
acaaagataa catttatctt ataacaaaaa tttgatagtt ttaaaggtta gtattgtgta      60
gggtattttc caaagacta aagagataac tcaggtaaaa agttagaaat gtataaaaca     120
ccatcagaca ggttttaaa aaacaacata ttacaaaatt agacaatcat ccttaaaaaa     180
aaaacttctt gtatcaattt cttttgttca aaatgactga cttaantatt tttaaatatt    240
tcanaaacac ttcctcaaaa attttcaana tggtagcttt canatgtncc ctcagtccca    300
atgttgctca gataaataaa tctcgtgaga acttaccacc caccacaagc tttctggggc    360
atgcaacagt gtcttttctt tnctttttct tttttttttt ttacaggcac agaaactcat    420
caatttat t tggataacaa agggtctcca aattatattg aaaatataat ccaagttaat   480
atcactcttg t                                                          491
```

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53

```
acataattta gcagggctaa ttaccataag atgctattta ttaanaggtn tatgatctga      60
gtattaacag ttgctgaagt ttggtatttt tatgcagcat tttcttttg ctttgataac    120
actacagaac ccttaaggac actgaaaatt agtaagtaaa gttcagaaac attagctgct   180
caatcaaatc tctacataac actatagtaa ttaaaacgtt aaaaaaagt gttgaaatct    240
gcactagtat anaccgctcc tgtcaggata anactgcttt ggaacagaaa gggaaaaanc   300
agctttgant ttctttgtgc tgatangagg aaaggctgaa ttaccttgtt gcctctccct    360
aatgattggc aggtcnggta aatnccaaaa catattccaa ctcaacactt cttttccncg    420
tancttgant ctgtgtattc caggancagg cggatggaat gggccagccc ncggatgttc    480
cant                                                                   484
```

<210> SEQ ID NO 54
<211> LENGTH: 151
<212> TYPE: DNA
<213> ORGANISM: Homo sapien

<400> SEQUENCE: 54

```
actaaacctc gtgcttgtga actccataca gaaaacggtg ccatccctga acacggctgg      60
```

-continued

```
ccactgggta tactgctgac aaccgcaaca acaaaaacac aaatccttgg cactggctag      120
tctatgtcct ctcaagtgcc tttttgtttg t                                    151
```

<210> SEQ ID NO 55
<211> LENGTH: 91
<212> TYPE: DNA
<213> ORGANISM: Homo sapien

<400> SEQUENCE: 55

```
acctggcttg tctccgggtg gttcccggcg ccccccacgg tccccagaac ggacactttc       60
gccctccagt ggatactcga gccaaagtgg t                                     91
```

<210> SEQ ID NO 56
<211> LENGTH: 133
<212> TYPE: DNA
<213> ORGANISM: Homo sapien

<400> SEQUENCE: 56

```
ggcggatgtg cgttggttat atacaaatat gtcattttat gtaagggact tgagtatact       60 tggattttttg gtatctgtgg gttgggggga cggtccagga accaataccc catggatacc     120
aagggacaac tgt                                                        133
```

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57

```
actctggaga acctgagccg ctgctccgcc tctgggatga ggtgatgcan gcngtggcgc       60
gactgggagc tgagcccttc cctttgcgcc tgcctcagag gattgttgcc gacntgcana     120
tctcantggg ctggatncat gcagggt                                         147
```

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58

```
acagggatat aggtttnaag ttattgtnat tgtaaaatac attgaatttt ctgtatactc       60
tgattacata catttatcct ttaaaaaaga tgtaaatctt aatttttatg ccatctatta     120
atttaccaat gagttacctt gtaaatgaga agtcatgata gcactgaatt taactagtt      180 ttgacttcta agtttggt                                                   198
```

<210> SEQ ID NO 59
<211> LENGTH: 330
<212> TYPE: DNA
<213> ORGANISM: Homo sapien

<400> SEQUENCE: 59

```
acaacaaatg ggttgtgagg aagtcttatc agcaaaactg gtgatggcta ctgaaaagat       60
```

-continued

| | | | | |
|---|---|---|---|---|
| ccattgaaaa | ttatcattaa | tgattttaaa | tgacaagtta | tcaaaactc actcaatttt | 120 |
| cacctgtgct | agcttgctaa | aatgggagtt | aactctagag | caaatatagt atcttctgaa | 180 |
| tacagtcaat | aaatgacaaa | gccagggcct | acaggtggtt | tccagactttt ccagacccag | 240 |
| cagaaggaat | ctattttatc | acatggatct | ccgtctgtgc | tcaaaatacc taatgatatt | 300 |
| tttcgtcttt | attggacttc | tttgaagagt | | | 330 |

<210> SEQ ID NO 60
<211> LENGTH: 175
<212> TYPE: DNA
<213> ORGANISM: Homo sapien

<400> SEQUENCE: 60

| | | | | |
|---|---|---|---|---|
| accgtgggtg | ccttctacat | tcctgacggc | tccttcacca | acatctggtt ctacttcggc | 60 |
| gtcgtgggct | cctccctctt | catcctcatc | cagctggtgc | tgctcatcga ctttgcgcac | 120 |
| tcctggaacc | agcggtggct | gggcaaggcc | gaggagtgcg | attcccgtgc ctggt | 175 |

<210> SEQ ID NO 61
<211> LENGTH: 154
<212> TYPE: DNA
<213> ORGANISM: Homo sapien

<400> SEQUENCE: 61

| | | | | |
|---|---|---|---|---|
| accccacttt | tcctcctgtg | agcagtctgg | acttctcact | gctacatgat gagggtgagt | 60 |
| ggttgttgct | cttcaacagt | atcctcccct | ttccggatct | gctgagccgg acagcagtgc | 120 |
| tggactgcac | agccccgggg | ctccacattg | ctgt | | 154 |

<210> SEQ ID NO 62
<211> LENGTH: 30
<212> TYPE: DNA
<213> ORGANISM: Homo sapien

<400> SEQUENCE: 62

| | | |
|---|---|---|
| cgctcgagcc | ctatagtgag | tcgtattaga | 30 |

<210> SEQ ID NO 63
<211> LENGTH: 89
<212> TYPE: DNA
<213> ORGANISM: Homo sapien

<400> SEQUENCE: 63

| | | | | |
|---|---|---|---|---|
| acaagtcatt | tcagcaccct | ttgctcttca | aaactgacca | tcttttatat ttaatgcttc | 60 |
| ctgtatgaat | aaaaatggtt | atgtcaagt | | | 89 |

<210> SEQ ID NO 64
<211> LENGTH: 97
<212> TYPE: DNA
<213> ORGANISM: Homo sapien

<400> SEQUENCE: 64

| | | | | |
|---|---|---|---|---|
| accggagtaa | ctgagtcggg | acgctgaatc | tgaatccacc | aataaataaa ggttctgcag | 60 |
| aatcagtgca | tccaggattg | gtccttggat | ctggggt | | 97 |

<210> SEQ ID NO 65
<211> LENGTH: 377
<212> TYPE: DNA
<213> ORGANISM: Homo sapien
<220> FEATURE:
<221> NAME/KEY: misc_feature

```
<222> LOCATION: (1)...(377)
<223> OTHER INFORMATION: n = A,T,C or G

<400> SEQUENCE: 65
acaacaanaa ntcccttctt taggccactg atggaaacct ggaaccccct tttgatggca      60
gcatggcgtc ctaggccttg acacagcggc tggggtttgg gctntcccaa accgcacacc    120
ccaaccctgg tctacccaca nttctggcta tgggctgtct ctgccactga acatcagggt    180
tcggtcataa natgaaatcc caangggac agaggtcagt agaggaagct caatgagaaa     240
ggtgctgttt gctcagccag aaaacagctg cctggcattc gccgctgaac tatgaacccg    300
tgggggtgaa ctaccccan gaggaatcat gcctgggcga tgcaaggtg ccaacaggag      360
gggcgggagg agcatgt                                                    377

<210> SEQ ID NO 66
<211> LENGTH: 305
<212> TYPE: DNA
<213> ORGANISM: Homo sapien

<400> SEQUENCE: 66
acgcctttcc ctcagaattc agggaagaga ctgtcgcctg ccttcctccg ttgttgcgtg      60
agaacccgtg tgccccttcc caccatatcc accctcgctc catctttgaa ctcaaacacg    120
aggaactaac tgcaccctgg tcctctcccc agtccccagt tcaccctcca tccctcacct    180
tcctccactc taagggatat caacactgcc cagcacaggg gccctgaatt tatgtggttt    240
ttatatattt tttaataaga tgcactttat gtcatttttt aataaagtct gaagaattac    300
tgttt                                                                 305

<210> SEQ ID NO 67
<211> LENGTH: 385
<212> TYPE: DNA
<213> ORGANISM: Homo sapien

<400> SEQUENCE: 67
actacacaca ctccacttgc ccttgtgaga cactttgtcc cagcacttta ggaatgctga      60
ggtcggacca gccacatctc atgtgcaaga ttgcccagca gacatcaggt ctgagagttc    120
cccttttaaa aaggggact tgcttaaaaa agaagtctag ccacgattgt gtagagcagc    180
tgtgctgtgc tggagattca cttttgagag agttctcctc tgagacctga tctttagagg    240
ctgggcagtc ttgcacatga gatggggctg gtctgatctc agcactcctt agtctgcttg    300
cctctcccag ggccccagcc tggccacacc tgcttacagg gcactctcag atgcccatac    360
catagtttct gtgctagtgg accgt                                           385

<210> SEQ ID NO 68
<211> LENGTH: 73
<212> TYPE: DNA
<213> ORGANISM: Homo sapien

<400> SEQUENCE: 68
acttaaccag atatattttt accccagatg gggatattct ttgtaaaaaa tgaaaataaa      60
gttttttttaa tgg                                                       73

<210> SEQ ID NO 69
<211> LENGTH: 536
<212> TYPE: DNA
<213> ORGANISM: Homo sapien
<220> FEATURE:
```

<221> NAME/KEY: misc_feature
<222> LOCATION: (1)...(536)
<223> OTHER INFORMATION: n = A,T,C or G

<400> SEQUENCE: 69

```
actagtccag tgtggtggaa ttccattgtg ttgggggctc tcaccctcct ctcctgcagc      60
tccagctttg tgctctgcct ctgaggagac catggcccag catctgagta ccctgctgct     120
cctgctggcc accctagctg tggccctggc ctggagcccc aaggaggagg ataggataat     180
cccgggtggc atctataacg cagacctcaa tgatgagtgg gtacagcgtg cccttcactt     240
cgccatcagc gagtataaca aggccaccaa agatgactac tacagacgtc cgctgcgggt     300
actaagagcc aggcaacaga ccgttggggg ggtgaattac ttcttcgacg tagaggtggg     360
ccgaaccata tgtaccaagt cccagcccaa cttggacacc tgtgccttcc atgaacagcc     420
agaactgcag aagaaacagt tgtgctcttt cgagatctac gaagttccct ggggagaaca     480
gaangtccct gggtgaaatc caggtgtcaa gaaatcctan ggatctgttg ccaggc         536
```

<210> SEQ ID NO 70
<211> LENGTH: 477
<212> TYPE: DNA
<213> ORGANISM: Homo sapien

<400> SEQUENCE: 70

```
atgacccta acaggggccc tctcagcct cctaatgacc tccggcctag ccatgtgatt        60
tcacttccac tccataacgc tcctcatact aggcctacta accaacacac taaccatata     120
ccaatgatgg cgcgatgtaa cacgagaaag cacataccaa ggccaccaca caccacctgt     180
ccaaaaaggc cttcgatacg ggataatcct atttattacc tcagaagttt ttttcttcgc     240
agggattttt ctgagccttt taccactcca gcctagcccc tacccccaa ctaggagggc     300
actggccccc aacaggcatc acccccgctaa atccctaga agtccactc ctaaacacat      360
ccgtattact cgcatcagga gtatcaatca cctgagctca ccatagtcta atagaaaaca     420
accgaaacca aattattcaa agcactgctt attacaattt tactgggtct ctattttt      477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

```
agagctatag gtacagtgtg atctcagctt tgcaaacaca ttttctacat agatagtact      60
aggtattaat agatatgtaa agaaagaaat cacaccatta ataatggtaa gattggttta    120
tgtgatttta gtggtatttt tggcacccct atatatgttt tccaaacttt cagcagtgat    180
attatttcca taacttaaaa agtgagtttg aaaagaaaa tctccagcaa gcatctcatt    240
taaataaagg tttgtcatct ttaaaaatac agcaatatgt gactttttaa aaaagctgtc    300
aaataggtgt gaccctacta ataattatta gaaatacatt taaaaacatc gagtacctca    360
agtcagtttg ccttgaaaaa tatcaaatat aactcttaga gaaatgtaca taaaagaatg    420
cttcgtaatt ttggagtang aggttccctc ctcaattttg tattttaaa aagtacatgg     480
taaaaaaaaa aattcacaac agtatataag gctgtaaaat gaagaattct gcc            533
```

```
<210> SEQ ID NO 72
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 72
tattacggaa aaacacacca cataattcaa ctancaaaga anactgcttc agggcgtgta      60
aaatgaaagg cttccaggca gttatctgat taaagaacac taaaagaggg acaaggctaa    120
aagccgcagg atgtctacac tatancaggc gctatttggg ttggctggag gagctgtgga    180
aaacatggan agattggtgc tgganatcgc cgtggctatt cctcattgtt attacanagt    240
gaggttctct gtgtgcccac tggtttgaaa accgttctnc aataatgata gaatagtaca    300
cacatgagaa ctgaaatggc ccaaacccag aaagaaagcc caactagatc ctcagaaanac   360 gcttctaggg acaataaccg atgaagaaaa gatggcctcc ttgtgccccc gtctgttatg    420
atttctctcc attgcagcna naaacccgtt cttctaagca aacncaggtg atgatggcna    480
aaatacaccc cctcttgaag naccnggagg a                                   511

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73
cagtgccagc actggtgcca gtaccagtac caataacagt gccagtgcca gtgccagcac     60
cagtggtggc ttcagtgctg gtgccagcct gaccgccact ctcacatttg gctcttcgc    120 tggccttggt ggagctggtg ccagcaccag tggcagctct ggtgcctgtg gtttctccta   180
caagtgagat tttagatatt gttaatcctg ccagtctttc tcttcaagcc agggtgcatc    240
ctcagaaacc tactcaacac agcactctag gcagccacta tcaatcaatt gaagttgaca    300
ctctgcatta aatctatttg ccatttctga aaaaaaaaaa aaaaaaggg cggccgctcg     360 antctagagg gcccgtttaa acccgctgat cagcctcgac tgtgccttct anttgccagc    420
catctgttgt ttgcccctcc cccgntgcct tccttgaccc tggaaagtgc cactcccact    480
gtcctttcct aantaaaat                                                499

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74
tttcatagga gaacacactg aggagatact tgaagaattt ggattcagcc gcgaagagat     60
ttatcagctt aactcagata aaatcattga aagtaataag gtaaaagcta gtctctaact    120
tccaggccca cggctcaagt gaatttgaat actgcattta cagtgtagag taacacataa    180
cattgtatgc atggaaacat ggaggaacag tattacagtg tcctaccact ctaatcaaga    240
```

```
aaagaattac agactctgat tctacagtga tgattgaatt ctaaaaatgg taatcattag      300
ggcttttgat ttataanact ttgggtactt atactaaatt atggtagtta tactgccttc      360
cagtttgctt gatatatttg ttgatattaa gattcttgac ttatattttg aatgggttct      420
actgaaaaan gaatgatata ttcttgaaga catcgatata catttattta cactcttgat      480
tctacaatgt agaaaatgaa ggaaatgccc caaattgtat ggtgataaaa gtcccgt        537
```

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75

```
caaanacaat tgttcaaaag atgcaaatga tacactactg ctgcagctca caaacacctc       60
tgcatattac acgtacctcc tcctgctcct caagtagtgt ggtctatttt gccatcatca      120
cctgctgtct gcttagaaga acggctttct gctgcaangg agagaaatca taacagacgg      180
tggcacaagg aggccatctt ttcctcatcg gttattgtcc ctagaagcgt cttctgagga      240
tctagttggg cttttctttct gggtttgggc catttcantt ctcatgtgtg tactattcta      300
tcattattgt ataacggttt tcaaaccngt gggcacncag agaacctcac tctgtaataa      360
caatgaggaa tagccacggt gatctccagc accaaatctc tccatgttnt tccagagctc      420
ctccagccaa cccaaatagc cgctgctatn gtgtagaaca tccctgn                    467
```

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76

```
aagctgacag cattcgggcc gagatgtctc gctccgtggc cttagctgtg ctcgcgctac       60
tctctctttc tggcctggag gctatccagc gtactccaaa gattcaggtt tactcacgtc      120
atccagcaga gaatggaaag tcaaatttcc tgaattgcta tgtgtctggg tttcatccat      180
ccgacattga agttgactta ctgaagaatg gagagagaat tgaaaagtg gagcattcag      240 acttgtcttt cagcaaggac tggtctttct atctcttgta ctacactgaa ttcaccccca      300
ctgaaaaaga tgagtatgcc tgccgtgtga accatgtgac tttgtcacag cccaagatng      360
ttnagtggga tcganacatg taagcagcan catgggaggt                             400
```

<210> SEQ ID NO 77
<211> LENGTH: 248
<212> TYPE: DNA
<213> ORGANISM: Homo sapien

<400> SEQUENCE: 77

```
ctggagtgcc ttggtgtttc aagcccctgc aggaagcaga atgcaccttc tgaggcacct       60
ccagctgccc cggcggggga tgcgaggctc ggagcaccct tgcccggctg tgattgctgc      120
caggcactgt tcatctcagc ttttctgtcc ctttgctccc ggcaagcgct tctgctgaaa      180
gttcatatct ggagcctgat gtcttaacga ataaaggtcc catgctccac ccgaaaaaaa      240
```

| aaaaaaaa | 248 |

<210> SEQ ID NO 78
<211> LENGTH: 201
<212> TYPE: DNA
<213> ORGANISM: Homo sapien

<400> SEQUENCE: 78

| actagtccag tgtggtggaa ttccattgtg ttgggcccaa cacaatggct acctttaaca | 60 |
| tcacccagac cccgccctgc ccgtgcccca cgctgctgct aacgacagta tgatgcttac | 120 |
| tctgctactc ggaaactatt tttatgtaat taatgtatgc tttcttgttt ataaatgcct | 180 |
| gatttaaaaa aaaaaaaaaa a | 201 |

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79

| tcctttttgtt aggtttttga dacaacccta gacctaaact gtgtcacaga cttctgaatg | 60 |
| tttaggcagt gctagtaatt tcctcgtaat gattctgtta ttactttcct attctttatt | 120 |
| cctctttctt ctgaagatta atgaagttga aaattgaggt ggataaatac aaaaaggtag | 180 |
| tgtgatagta taagtatcta agtgcagatg aaagtgtgtt atatatatcc attcaaaatt | 240 |
| atgcaagtta gtaattactc agggttaact aaattacttt aatatgctgt tgaacctact | 300 |
| ctgttccttg gctagaaaaa attataaaca ggactttgtt agtttgggaa gccaaattga | 360 |
| taatattcta tgttctaaaa gttgggctat acataaanta tnaagaaata tggaattta | 420 |
| ttcccaggaa tatggggttc atttatgaat antacccggg anagaagttt tgantnaaac | 480 |
| cngttttggt taatacgtta atatgtcctn aatnaacaag gcntgactta tttccaaaaa | 540 |
| aaaaaaaaaa aa | 552 |

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80

| acagggattt gagatgctaa ggccccagag atcgtttgat ccaaccctct tattttcaga | 60 |
| ggggaaaatg gggcctagaa gttacagagc atctagctgg tgcgctggca ccctggcct | 120 |
| cacacagact cccgagtagc tgggactaca ggcacacagt cactgaagca ggccctgttt | 180 |
| gcaattcacg ttgccacctc caacttaaac attcttcata tgtgatgtcc ttagtcacta | 240 |
| aggtaaaact ttcccaccca gaaaggcaa cttagataaa atcttagagt actttctatac | 300 |
| tcttctaagt cctcttccag cctcactttg agtcctcctt gggggttgat aggaantntc | 360 |
| tcttggcttt ctcaataaaa tctctatcca tctcatgttt aatttggtac gcntaaaaat | 420 |
| gctgaaaaaa ttaaaatgtt ctggtttcnc tttaaaaaaa aaaaaaaaaa aaaaaa | 476 |

<210> SEQ ID NO 81
<211> LENGTH: 232
<212> TYPE: DNA
<213> ORGANISM: Homo sapien
<220> FEATURE:
<221> NAME/KEY: misc_feature
<222> LOCATION: (1)...(232)
<223> OTHER INFORMATION: n = A,T,C or G

<400> SEQUENCE: 81

| | | | | | |
|---|---|---|---|---|---|
| ttttttttttg | tatgccntcn | ctgtggngtt | attgttgctg | ccaccctgga | ggagcccagt | 60 |
| ttcttctgta | tctttctttt | ctgggggatc | ttcctggctc | tgcccctcca | ttcccagcct | 120 |
| ctcatcccca | tcttgcactt | tgctagggt | tggaggcgct | ttcctggtag | cccctcagag | 180 |
| actcagtcag | cgggaataag | tcctaggggt | gggggtgtg | gcaagccggc | ct | 232 |

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82

| | | | | | |
|---|---|---|---|---|---|
| aggcgggagc | agaagctaaa | gccaaagccc | aagaagagtg | gcagtgccag | cactggtgcc | 60 |
| agtaccagta | ccaataacat | gccagtgcca | gtgccagcac | cagtggtggc | ttcagtgctg | 120 |
| gtgccagcct | gaccgccact | ctcacatttg | ggctcttcgc | tggccttggt | ggagctggtg | 180 |
| ccagcaccag | tggcagctct | ggtgcctgtg | gtttctccta | caagtgagat | tttagatatt | 240 |
| gttaatcctg | ccagtctttc | tcttcaagcc | agggtgcatc | ctcagaaacc | tactcaacac | 300 |
| agcactctng | gcagccacta | tcaatcaatt | gaagttgaca | ctctgcatta | aatctatttg | 360 |
| ccatttcaaa | aaaaaaaaaa | aaa | | | | 383 |

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83

| | | | | | |
|---|---|---|---|---|---|
| accgaattgg | gaccgctggc | ttataagcga | tcatgtcctc | cagtattacc | tcaacgagca | 60 |
| gggagatcga | gtctatacgc | tgaagaaatt | tgacccgatg | ggacaacaga | cctgctcagc | 120 |
| ccatcctgct | cggttctccc | cagatgacaa | atactctcga | caccgaatca | ccatcaagaa | 180 |
| acgcttcaag | gtgctcatga | cccagcaacc | gcgccctgtc | ctctgagggt | ccttaaactg | 240 |
| atgtcttttc | tgccacctgt | tacccctcgg | agactccgta | accaaactct | tcggactgtg | 300 |
| agccctgatg | ccttttttgcc | agccatactc | tttggcntcc | agtctctcgt | ggcgattgat | 360 |
| tatgcttgtg | tgaggcaatc | atggtggcat | cacccatnaa | gggaacacat | ttganttttt | 420 |
| tttcncatat | tttaaattac | naccagaata | nttcagaata | aatgaattga | aaaactctta | 480 |
| aaaaaaaaaa | aaaa | | | | | 494 |

<210> SEQ ID NO 84
<211> LENGTH: 380

```
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 84
gctggtagcc tatggcgtgg ccacggangg gctcctgagg cacgggacag tgacttccca      60
agtatcctgc gccgcgtctt ctaccgtccc tacctgcaga tcttcgggca gattccccag     120
gaggacatgg acgtggccct catggagcac agcaactgct cgtcggagcc cggcttctgg     180
gcacaccctc ctggggccca ggcgggcacc tgcgtctccc agtatgccaa ctggctggtg     240
gtgctgctcc tcgtcatctt cctgctcgtg gccaacatcc tgctggtcac ttgctcattg     300
ccatgttcag ttacacattc ggcaaagtac agggcaacag cnatctctac tgggaaggcc     360
agcgttnccg cctcatccgg                                                  380

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85
gagttagctc ctccacaacc ttgatgaggt cgtctgcagt ggcctctcgc ttcataccgc      60
tnccatcgtc atactgtagg tttgccacca cctcctgcat cttggggcgg ctaatatcca     120
ggaaactctc aatcaagtca ccgtcnatna aacctgtggc tggttctgtc ttccgctcgg     180
tgtgaaagga tctccagaag gagtgctcga tcttccccac acttttgatg actttattga     240
gtcgattctg catgtccagc aggaggttgt accagctctc tgacagtgag gtcaccagcc     300
ctatcatgcc nttgaacgtg ccgaagaaca ccgagccttg tgtgggggt gnagtctcac     360 ccagattctg cattaccaga nagccgtggc aaaaganatt gacaactcgc ccaggnngaa     420
aaagaacacc tcctggaagt gctngccgct cctcgtccnt tggtggnngc gcntnccttt     480
t                                                                     481

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86
aacatcttcc tgtataatgc tgtgtaatat cgatccgatn ttgtctgctg agaattcatt      60
acttggaaaa gcaacttnaa gcctggacac tggtattaaa attcacaata tgcaacactt     120
taaacagtgt gtcaatctgc tcccttactt tgtcatcacc agtctgggaa taagggtatg     180
ccctattcac acctgttaaa agggcgctaa gcattttga ttcaacatct ttttttttga      240
cacaagtccg aaaaaagcaa aagtaaacag ttnttaattt gttagccaat tcactttctt     300
catgggacag agccatttga tttaaaaagc aaattgcata atattgagct ttgggagctg     360
atatntgagc ggaagantag cctttctact tcaccagaca caactccttt catattggga     420
```
tgttnacnaa agttatgtct cttacagatg ggatgctttt gtggcaattc tg     472

<210> SEQ ID NO 87
<211> LENGTH: 413
<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87
agaaaccagt atctctnaaa acaacctctc ataccttgtg gacctaattt tgtgtgcgtg      60
tgtgtgtgcg cgcatattat atagacaggc acatctttt tacttttgta aaagcttatg     120
cctctttggt atctatatct gtgaaagttt taatgatctg ccataatgtc ttggggacct    180
ttgtcttctg tgtaaatggt actagagaaa acacctatnt tatgagtcaa tctagttngt    240
tttattcgac atgaaggaaa tttccagatn acaacactna caaactctcc cttgactagg    300
ggggacaaag aaaagcanaa ctgaacatna gaaacaattn cctggtgaga aattncataa    360
acagaaattg ggtngtatat tgaaananng catcattnaa acgttttttt ttt          413

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88
cgcagcgggt cctctctatc tagctccagc ctctcgcctg ccccactccc cgcgtcccgc      60
gtcctagccn accatggccg ggcccctgcg cgccccgctg ctcctgctgg ccatcctggc    120
cgtggccctg gccgtgagcc ccgcggccgg ctccagtccc ggcaagccgc cgcgcctggt    180
gggaggccca tggaccccgc gtggaagaag aaggtgtgcg cgtgcactg gactttgccg     240 tcggcnanta caacaaaccc gcaacnactt ttaccnagcn cgcgctgcag gttgtgccgc    300
cccaancaaa ttgttactng gggtaantaa ttcttggaag ttgaacctgg gccaaacnng    360
tttaccagaa ccnagccaat tngaacaatt nccctccat aacagcccct tttaaaaagg    420
gaancantcc tgntcttttc caaatttt                                       448

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89
gaattttgtg cactggccac tgtgatggaa ccattgggcc aggatgcttt gagtttatca      60
gtagtgattc tgccaaagtt ggtgttgtaa catgagtatg taaaatgtca aaaaattagc    120
agaggtctag gtctgcatat cagcagacag tttgtccgtg tattttgtag ccttgaagtt    180
ctcagtgaca agttnnttct gatgcgaagt tctnattcca gtgttttagt cctttgcatc    240
tttnatgttn agacttgcct ctntnaaatt gcttttgtnt tctgcaggta ctatctgtgg    300
tttaacaaaa tagaannact tctctgcttn gaanatttga atatcttaca tctnaaaatn    360

```
aattctctcc ccatannaaa acccangccc ttgggganaat ttgaaaaang gntccttcnn      420
aattcnnana anttcagntn tcatacaaca naacnggganc ccc                       463
```

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90

```
agggattgaa ggtctnttnt actgtcggac tgttcancca ccaactctac aagttgctgt       60
cttccactca ctgtctgtaa gcntnttaac ccagactgta tcttcataaa tagaacaaat      120
tcttcaccag tcacatcttc taggacctttt ttggattcag ttagtataag ctcttccact    180
tcctttgtta agacttcatc tggtaaagtc ttaagttttg tagaaaggaa tttaattgct      240
cgttctctaa caatgtcctc tccttgaagt atttggctga acaacccacc tnaagtccct      300
ttgtgcatcc atttttaaata tacttaatag ggcattggtn cactaggtta aattctgcaa    360
gagtcatctg tctgcaaaag ttgcgttagt atatctgcca                            400
```

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91

```
gagctcggat ccaataatct ttgtctgagg gcagcacaca tatncagtgc catggnaact       60
ggtctacccc acatgggagc agcatgccgt agntatataa ggtcattccc tgagtcagac      120
atgcctcttt gactaccgtg tgccagtgct ggtgattctc acacacctcc nnccgctctt     180
tgtggaaaaa ctggcacttg nctggaacta gcaagacatc acttacaaat tcacccacga     240
gacacttgaa aggtgtaaca aagcgactct tgcattgctt tttgtccctc cggcaccagt     300
tgtcaatact aacccgctgg tttgcctcca tcacatttgt gatctgtagc tctggataca    360
tctcctgaca gtactgaaga acttcttctt ttgtttcaaa agcaactctt ggtgcctgtt     420
ngatcaggtt cccatttccc agtccgaatg ttcacatggc atatnttact tcccacaaaa    480
```

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92

```
atacagccca natcccacca cgaagatgcg cttgttgact gagaacctga tgcggtcact       60
ggtcccgctg tagccccagc gactctccac ctgctggaag cggttgatgc tgcactcctt      120
cccacgcagg cagcagcggg gccggtcaat gaactccact cgtggcttgg ggttgacggt     180
taantgcagg aagaggctga ccacctcgcg gtccaccagg atgcccgact gtgcgggacc     240
```

| | |
|---|---|
| tgcagcgaaa ctcctcgatg gtcatgagcg ggaagcgaat gangcccagg gccttgccca | 300 |
| gaaccttccg cctgttctct ggcgtcacct gcagctgctg ccgctnacac tcggcctcgg | 360 |
| accagcggac aaacggcgtt gaacagccgc acctcacgga tgcccantgt gtcgcgctcc | 420 |
| aggaacggcn ccagcgtgtc caggtcaatg tcggtgaanc ctccgcgggt aatggcg | 477 |

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93

| | |
|---|---|
| gaacggctgg accttgcctc gcattgtgct gctggcagga ataccttggc aagcagctcc | 60 |
| agtccgagca gccccagacc gctgccgccc gaagctaagc ctgcctctgg ccttcccctc | 120 |
| cgcctcaatg cagaaccant agtgggagca ctgtgtttag agttaagagt gaacactgtn | 180 |
| tgattttact tgggaatttc ctctgttata tagcttttcc caatgctaat ttccaaacaa | 240 |
| caacaacaaa ataacatgtt tgcctgttna gttgtataaa agtangtgat tctgtatnta | 300 |
| aagaaaatat tactgttaca tatactgctt gcaanttctg tatttattgg tnctctggaa | 360 |
| ataaatatat tattaaa | 377 |

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94

| | |
|---|---|
| ccctttgagg ggttagggtc cagttcccag tggaagaaac aggccaggag aantgcgtgc | 60 |
| cgagctgang cagatttccc acagtgaccc cagagccctg gctatagtc tctgacccct | 120 |
| ccaaggaaag accaccttct ggggacatgg gctggagggc aggacctaga ggcaccaagg | 180 |
| gaaggcccca ttccggggct gttccccgag gaggaaggga aggggctctg tgtgcccccc | 240 |
| acgaggaana ggccctgant cctgggatca nacacccctt cacgtgtatc cccacacaaa | 300 |
| tgcaagctca ccaaggtccc ctctcagtcc cttccctaca ccctgaacgg ncactggccc | 360 |
| acacccaccc agancancca cccgccatgg ggaatgtnct caaggaatcg cnggggcaacg | 420 |
| tggactctng tcccnnaagg gggcagaatc tccaatagan ggannngaacc cttgctnana | 480 |
| aaaaaaaana aaaaa | 495 |

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95

| | |
|---|---|
| ggttacttgg tttcattgcc accacttagt ggatgtcatt tagaaccatt ttgtctgctc | 60 |
| cctctggaag ccttgcgcag agcggacttt gtaattgttg gagaataact gctgaatttt | 120 |

```
tagctgtttt gagttgattc gcaccactgc accacaactc aatatgaaaa ctatttnact      180
tatttattat cttgtgaaaa gtatacaatg aaaattttgt tcatactgta tttatcaagt      240
atgatgaaaa gcaatagata tatattcttt tattatgttn aattatgatt gccattatta     300
atcggcaaaa tgtggagtgt atgttctttt cacagtaata tatgccttt gtaacttcac      360 ttggttattt tattgtaaat gaattacaaa attcttaatt taagaaaatg gtangttata     420
tttanttcan taatttcttt ccttgtttac gttaattttg aaaagaatgc at             472
```

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

```
ctgaagcatt tcttcaaact tntctacttt tgtcattgat acctgtagta agttgacaat      60
gtggtgaaat ttcaaaatta tatgtaactt ctactagttt tactttctcc cccaagtctt     120
ttttaactca tgattttttac acacacaatc cagaacttat tatatagcct ctaagtcttt    180
attcttcaca gtagatgatg aaagagtcct ccagtgtctt gngcanaatg ttctagntat     240
agctggatac atacngtggg agttctataa actcatacct cagtgggact naaccaaaat    300
tgtgttagtc tcaattccta ccacactgag ggagcctccc aaatcactat attcttatct    360
gcaggtactc ctccagaaaa acngacaggg caggcttgca tgaaaaagtn acatctgcgt    420
tacaaagtct atcttcctca nangtctgtn aaggaacaat ttaatcttct agcttt        476
```

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

```
actctttcta atgctgatat gatcttgagt ataagaatgc atatgtcact agaatggata      60
aaataatgct gcaaacttaa tgttcttatg caaaatggaa cgctaatgaa acacagctta    120
caatcgcaaa tcaaaactca caagtgctca tctgttgtag atttagtgta ataagactta    180
gattgtgctc cttcggatat gattgtttct canatcttgg gcaatnttcc ttagtcaaat    240
caggctacta gaattctgtt attggatatn tgagagcatg aaattttaa naatacactt     300 gtgattatna aattaatcac aaatttcact tatacctgct atcagcagct agaaaaacat    360
ntnnttttta natcaaagta ttttgtgttt ggaantgtnn aaatgaaatc tgaatgtggg    420
ttcnatctta ttttttcccn gacnactant tncttttta gggnctattc tganccatc     479
```

<210> SEQ ID NO 98
<211> LENGTH: 461
<212> TYPE: DNA
<213> ORGANISM: Homo sapien

<400> SEQUENCE: 98

```
agtgacttgt cctccaacaa aacccttga tcaagtttgt ggcactgaca atcagaccta      60
```

-continued

| | |
|---|---|
| tgctagttcc tgtcatctat tcgctactaa atgcagactg gagggacca aaaaggggca | 120 |
| tcaactccag ctggattatt ttggagcctg caaatctatt cctacttgta cggactttga | 180 |
| agtgattcag tttcctctac ggatgagaga ctggctcaag aatatcctca tgcagcttta | 240 |
| tgaagccact ctgaacacgc tggttatcta gatgagaaca gagaaataaa gtcagaaaat | 300 |
| ttacctggaa aaagaggct ttggctgggg accatcccat gaaccttct cttaaggact | 360 |
| ttaagaaaaa ctaccacatg ttgtgtatcc tggtgccggc cgtttatgaa ctgaccaccc | 420 |
| tttggaataa tcttgacgct cctgaacttg ctcctctgcg a | 461 |

<210> SEQ ID NO 99
<211> LENGTH: 171
<212> TYPE: DNA
<213> ORGANISM: Homo sapien

<400> SEQUENCE: 99

| | |
|---|---|
| gtggccgcgc gcaggtgttt cctcgtaccg cagggccccc tcccttcccc aggcgtccct | 60 |
| cggcgcctct gcgggcccga ggaggagcgg ctggcgggtg gggggagtgt gacccaccct | 120 |
| cggtgagaaa agccttctct agcgatctga gaggcgtgcc ttgggggtac c | 171 |

<210> SEQ ID NO 100
<211> LENGTH: 269
<212> TYPE: DNA
<213> ORGANISM: Homo sapien

<400> SEQUENCE: 100

| | |
|---|---|
| cggccgcaag tgcaactcca gctggggccg tgcggacgaa gattctgcca gcagttggtc | 60 |
| cgactgcgac gacggcggcg gcgacagtcg caggtgcagc gcgggcgcct gggtcttgc | 120 |
| aaggctgagc tgacgccgca gaggtcgtgt cacgtcccac gaccttgacg ccgtcgggga | 180 |
| cagccggaac agagcccggt gaagcgggag gcctcgggga gccctcgggg aagggcggcc | 240 |
| cgagagatac gcaggtgcag gtggccgcc | 269 |

<210> SEQ ID NO 101
<211> LENGTH: 405
<212> TYPE: DNA
<213> ORGANISM: Homo sapien

<400> SEQUENCE: 101

| | |
|---|---|
| tttttttttt ttttggaatc tactgcgagc acagcaggtc agcaacaagt ttattttgca | 60 |
| gctagcaagg taacagggta gggcatggtt acatgttcag gtcaacttcc tttgtcgtgg | 120 |
| ttgattggtt tgtctttatg ggggcggggt ggggtagggg aaacgaagca ataacatgg | 180 |
| agtgggtgca ccctccctgt agaacctggt tacaaagctt ggggcagttc acctggtctg | 240 |
| tgaccgtcat tttcttgaca tcaatgttat tagaagtcag gatatctttt agagagtcca | 300 |
| ctgttctgga gggagattag ggtttcttgc caaatccaac aaaatccact gaaaaagttg | 360 |
| gatgatcagt acgaataccg aggcatattc tcatatcggt ggcca | 405 |

<210> SEQ ID NO 102
<211> LENGTH: 470
<212> TYPE: DNA
<213> ORGANISM: Homo sapien

<400> SEQUENCE: 102

| | |
|---|---|
| tttttttttt tttttttttt tttttttttt tttttttttt tttttttttt tttttttttt | 60 |
| ggcacttaat ccatttttat ttcaaaatgt ctacaaattt aatcccatta tacggtattt | 120 |

-continued

| | |
|---|---|
| tcaaaatcta aattattcaa attagccaaa tccttaccaa ataataccca aaaatcaaaa | 180 |
| atatacttct ttcagcaaac ttgttacata aattaaaaaa atatatacgg ctggtgtttt | 240 |
| caaagtacaa ttatcttaac actgcaaaca ttttaaggaa ctaaaataaa aaaaaacact | 300 |
| ccgcaaaggt taagggaac aacaaattct tttacaacac cattataaaa atcatatctc | 360 |
| aaatcttagg ggaatatata cttcacacgg gatcttaact tttactcact ttgttttattt | 420 |
| ttttaaacca ttgtttgggc ccaacacaat ggaatccccc ctggactagt | 470 |

<210> SEQ ID NO 103
<211> LENGTH: 581
<212> TYPE: DNA
<213> ORGANISM: Homo sapien

<400> SEQUENCE: 103

| | |
|---|---|
| tttttttttt ttttttttga cccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa attttttgact cttgtaaaac atccaaattc | 240 |
| atttttcttg tctttaaaat tatctaatct ttccattttt tccctattcc aagtcaattt | 300 |
| gcttctctag cctcatttcc tagctcttat ctactattag taagtggctt ttttcctaaa | 360 |
| agggaaaaca ggaagagaaa tggcacacaa aacaaacatt ttatattcat atttctacct | 420 |
| acgttaataa aatagcattt tgtgaagcca gctcaaaaga aggcttagat cctttttatgt | 480 |
| ccattttagt cactaaacga tatcaaagtg ccagaatgca aaaggtttgt gaacatttat | 540 |
| tcaaaagcta atataagata tttcacatac tcatctttct g | 581 |

<210> SEQ ID NO 104
<211> LENGTH: 578
<212> TYPE: DNA
<213> ORGANISM: Homo sapien

<400> SEQUENCE: 104

| | |
|---|---|
| tttttttttt tttttttttt ttttctctct cttttttttt gaaatgagga tcgagttttt | 60 |
| cactctctag atagggcatg aagaaaactc atctttccag ctttaaaata acaatcaaat | 120 |
| ctcttatgct atatcatatt ttaagttaaa ctaatgagtc actggcttat cttctcctga | 180 |
| aggaaatctg ttcattcttc tcattcatat agttatatca agtactacct tgcatattga | 240 |
| gaggttttc ttctctattt acacatatat ttccatgtga atttgtatca aacctttatt | 300 |
| ttcatgcaaa ctagaaaata atgtttcttt tgcataagag aagagaacaa tatagcatta | 360 |
| caaaactgct caaattgttt gttaagttat ccattataat tagttggcag gagctaatac | 420 |
| aaatcacatt tacgacagca ataataaaac tgaagtacca gttaaatatc caaataatt | 480 |
| aaaggaacat tttagcctg ggtataatta gctaattcac tttacaagca tttattagaa | 540 |
| tgaattcaca tgttattatt cctagcccaa cacaatgg | 578 |

<210> SEQ ID NO 105
<211> LENGTH: 538
<212> TYPE: DNA
<213> ORGANISM: Homo sapien

<400> SEQUENCE: 105

| | |
|---|---|
| tttttttttt ttttcagta ataatcagaa caatatttat tttatatttt aaaattcata | 60 |

```
gaaaagtgcc ttacatttaa taaaagtttg tttctcaaag tgatcagagg aattagatat    120
gtcttgaaca ccaatattaa tttgaggaaa atacaccaaa atacattaag taaattattt    180
aagatcatag agcttgtaag tgaaagata aaatttgacc tcagaaactc tgagcattaa     240
aaatccacta ttagcaaata aattactatg gacttcttgc tttaattttg tgatgaatat    300
ggggtgtcac tggtaaacca acacattctg aaggatacat tacttagtga tagattctta    360
tgtactttgc taatacgtgg atatgagttg acaagtttct cttcttcaa tcttttaagg     420 ggcgagaaat gaggaagaaa agaaaaggat tacgcatact gttctttcta tggaaggatt    480
agatatgttt cctttgccaa tattaaaaaa ataataatgt ttactactag tgaaaccc     538

<210> SEQ ID NO 106
<211> LENGTH: 473
<212> TYPE: DNA
<213> ORGANISM: Homo sapien

<400> SEQUENCE: 106
tttttttttt ttttttagtc aagtttctat ttttattata attaaagtct tggtcatttc     60
atttattagc tctgcaactt acatatttaa attaaagaaa cgttttagac aactgtacaa    120
tttataaatg taaggtgcca ttattgagta atatattcct ccaagagtgg atgtgtccct    180
tctcccacca actaatgaac agcaacatta gtttaatttt attagtagat atacactgct    240
gcaaacgcta attctcttct ccatccccat gtgatattgt gtatatgtgt gagttggtag    300
aatgcatcac aatctacaat caacagcaag atgaagctag ctgggctttt cggtgaaaat    360
agactgtgtc tgtctgaatc aaatgatctg acctatcctc ggtggcaaga actcttcgaa    420
ccgcttcctc aaaggcgctg ccacatttgt ggctctttgc acttgtttca aaa           473

<210> SEQ ID NO 107
<211> LENGTH: 1621
<212> TYPE: DNA
<213> ORGANISM: Homo sapien

<400> SEQUENCE: 107
cgccatggca ctgcagggca tctcggtcat ggagctgtcc ggcctggccc cgggcccgtt     60
ctgtgctatg gtcctggctg acttcggggc gcgtgtggta cgcgtggacc ggcccggctc    120
ccgctacgac gtgagccgct gggccgggg caagcgctcg ctagtgctgg acctgaagca    180
gccgcgggga gccgccgtgc tgcggcgtct gtgcaagcgg tcggatgtgc tgctggagcc    240
cttccgccgc ggtgtcatgg agaaactcca gctgggccca gagattctgc agcgggaaaa    300
tccaaggctt atttatgcca ggctgagtgg atttggccag tcaggaagct tctgccggtt    360
agctggccac gatatcaact atttggcttt gtcaggtgtt ctctcaaaaa ttggcagaag    420
tggtgagaat ccgtatgccc cgctgaatct cctggctgac tttgctggtg gtggccttat    480
gtgtgcactg ggcattataa tggctctttt tgaccgcaca cgcactgaca agggtcaggt    540
cattgatgca aatatggtgg aaggaacagc atatttaagt tcttttctgt ggaaaactca    600
gaaatcgagt ctgtgggaag cacctcgagg acagaacatg ttggatggtg agcacctttt    660
ctatacgact tacaggacag cagatgggga attcatggct gttggagcaa tagaacccca    720
gttctacgag ctgctgatca aaggacttgg actaaagtct gatgaacttc ccaatcagat    780
gagcatggat gattgccag aaatgaagaa aagtttgca gatgtatttg caaagaagac     840
gaaggcagag tggtgtcaaa tctttgacgg cacagatgcc tgtgtgactc cggttctgac    900
ttttgaggag gttgttcatc atgatcacaa caaggaacgg ggctcgttta tcaccagtga    960
```

-continued

```
ggagcaggac gtgagccccc gccctgcacc tctgctgtta acacccccag ccatcccttc      020
tttcaaaagg gatcctttca taggagaaca cactgaggag atacttgaag aatttggatt     1080
cagccgcgaa gagatttatc agcttaactc agataaaatc attgaaagta ataaggtaaa     1140
agctagtctc taacttccag gcccacggct caagtgaatt tgaatactgc atttacagtg     1200
tagagtaaca cataacattg tatgcatgga acatggagg  aacagtatta cagtgtccta     1260
ccactctaat caagaaaaga attacagact ctgattctac agtgatgatt gaattctaaa     1320
aatggttatc attagggctt ttgatttata aactttggg  tacttatact aaattatggt     1380
agttattctg ccttccagtt tgcttgatat atttgttgat attaagattc ttgacttata     1440
ttttgaatgg gttctagtga aaaggaatg  atatattctt gaagacatcg atatacattt     1500
atttacactc ttgattctac aatgtagaaa atgaggaaat gccacaaatt gtatggtgat     1560
aaaagtcacg tgaaacaaaa aaaaaaaaaa aaaaaaaaaa aaaaaaaaaa aaaaaaaaa      1620
a                                                                    1621
```

<210> SEQ ID NO 108
<211> LENGTH: 382
<212> TYPE: PRT
<213> ORGANISM: Homo sapien

<400> SEQUENCE: 108

```
Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
```

|         |         |         |         |         |         |         |         |         |         |         |         |
|---------|---------|---------|---------|---------|---------|---------|---------|---------|---------|---------|---------|
|         |         |         | 245     |         |         |         | 250     |         |         |         | 255     |
| Asn     | Gln     | Met     | Ser     | Met     | Asp     | Asp     | Trp     | Pro     | Glu     | Met     | Lys     | Lys     | Phe     | Ala     |
|         |         |         |         | 260     |         |         |         |         | 265     |         |         |         | 270     |         |

Asn Gln Met Ser Met Asp Asp Trp Pro Glu Met Lys Lys Phe Ala
                245             250                 255
                    260                 265                 270

Asp Val Phe Ala Lys Lys Thr Lys Ala Glu Trp Cys Gln Ile Phe Asp
            275                 280                 285

Gly Thr Asp Ala Cys Val Thr Pro Val Leu Thr Phe Glu Glu Val Val
        290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Asn Thr Pro Ala
                325                 330                 335

Ile Pro Ser Phe Lys Arg Asp Pro Phe Ile Gly Glu His Thr Glu Glu
                340                 345                 350

Ile Leu Glu Glu Phe Gly Phe Ser Arg Glu Glu Ile Tyr Gln Leu Asn
                355                 360                 365

Ser Asp Lys Ile Ile Glu Ser Asn Lys Val Lys Ala Ser Leu
370                 375                 380

<210> SEQ ID NO 109
<211> LENGTH: 1524
<212> TYPE: DNA
<213> ORGANISM: Homo sapien

<400> SEQUENCE: 109

```
ggcacgaggc tgcgccaggg cctgagcgga ggcgggggca gcctcgccag cgggggcccc     60
gggcctggcc atgcctcact gagccagcgc ctgcgcctct acctcgccga cagctggaac    120
cagtgcgacc tagtggctct cacctgcttc ctcctgggcg tgggctgccg gctgaccccg    180
ggtttgtacc acctgggccg cactgtcctc tgcatcgact tcatggtttt cacggtgcgg    240
ctgcttcaca tcttcacggt caacaaacag ctggggccca gatcgtcat cgtgagcaag    300 atgatgaagg acgtgttctt cttcctcttc ttcctcggcg tgtggctggt agcctatggc    360
gtggccacgg aggggctcct gaggccacgg acagtgact tcccaagtat cctgcgccgc    420
gtcttctacc gtccctacct gcagatcttc gggcagattc cccaggagga catggacgtg    480
gccctcatga gcacagcaa ctgctcgtcg gagcccggct ctgggcaca ccctcctggg    540 gcccaggcgg gcacctgcgt ctcccagtat gccaactggc tggtggtgct gctcctcgtc    600
atcttcctgc tcgtggccaa catcctgctg gtcaacttgc tcattgccat gttcagttac    660
acattcggca agtacagg caacagcgat ctctactgga aggcgcagcg ttaccgcctc    720
atccgggaat tccactctcg gcccgcgctg gccccgccct ttatcgtcat ctcccacttg    780
cgcctcctgc tcaggcaatt gtgcaggcga ccccggagcc cccagccgtc ctccccggcc    840
ctcgagcatt tccgggttta ccttctaag gaagccgagc ggaagctgct aacgtgggaa    900
tcggtgcata aggagaactt tctgctggca cgcgctaggg acaagcggga gagcgactcc    960
gagcgtctga gcgcacgtc ccagaaggtg gacttggcac tgaaacagct gggacacatc   1020
cgcgagtacg aacagcgcct gaaagtgctg gagcgggagg tccagcagtg tagccgcgtc   1080
ctggggtggg tggccgaggc cctgagccgc tctgccttgc tgcccccagg tgggccgcca   1140 cccctgacc tgcctgggtc caaagactga gccctgctgg cggacttcaa ggagaagccc   1200 ccacaggga ttttgctcct agagtaaggc tcatctgggc ctcggccccc gcacctggtg   1260
gccttgtcct tgaggtgagc ccatgtcca tctgggccac tgtcaggacc accttt ggga   1320 gtgtcatcct tacaaaccac agcatgcccg gctcctccca gaaccagtcc cagcctggga   1380
```

-continued

```
ggatcaaggc ctggatcccg ggccgttatc catctggagg ctgcagggtc cttggggtaa      1440
cagggaccac agaccctca ccactcacag attcctcaca ctggggaaat aaagccattt       1500
cagaggaaaa aaaaaaaaaa aaaa                                              1524
```

<210> SEQ ID NO 110
<211> LENGTH: 3410
<212> TYPE: DNA
<213> ORGANISM: Homo sapien

<400> SEQUENCE: 110

```
gggaaccagc ctgcacgcgc tggctccggg tgacagccgc gcgcctcggc caggatctga       60
gtgatgagac gtgtccccac tgaggtgccc cacagcagca ggtgttgagc atgggctgag      120
aagctggacc ggcaccaaag ggctggcaga atgggcgcc tggctgattc ctaggcagtt       180
ggcggcagca aggaggagag gccgcagctt ctggagcaga gccgagacga agcagttctg      240
gagtgcctga acggccccct gagccctacc cgcctggccc actatggtcc agaggctgtg      300
ggtgagccgc ctgctgcggc accggaaagc ccagctcttg ctggtcaacc tgctaacctt      360
tggcctggag gtgtgtttgg ccgcaggcat cacctatgtg ccgcctctgc tgctggaagt      420
gggggtagag gagaagttca tgaccatggt gctgggcatt ggtccagtgc tgggcctggt      480
ctgtgtcccg ctcctaggct cagccagtga ccactggcgt ggacgctatg ccgccgccg       540 gcccttcatc tggcactgt ccttgggcat cctgctgagc ctctttctca tcccaagggc       600
cggctggcta gcagggctgc tgtgcccgga tcccaggccc ctggagctgg cactgctcat      660
cctgggcgtg gggctgctgg acttctgtgg ccaggtgtgc ttcactccac tggaggccct      720
gctctctgac ctcttccggg acccggacca ctgtcgccag gcctactctg tctatgcctt      780
catgatcagt cttgggggct gcctgggcta cctcctgcct gccattgact gggacaccag      840
tgccctggcc ccctacctgg gcacccagga ggagtgcctc tttggcctgc tcaccctcat      900
cttcctcacc tgcgtagcag ccacactgct ggtggctgag gaggcagcgc tgggccccac      960
cgagccagca gaagggctgt cggcccctc cttgtcgccc cactgctgtc catgccgggc     1020
ccgcttggct ttccggaacc tgggcgccct gcttccccgg ctgcaccagc tgtgctgccg     1080
catgccccgc accctgcgcc ggctcttcgt ggctgagctg tgcagctgga tggcactcat     1140
gaccttcacg ctgttttaca cggatttcgt gggcgagggg ctgtaccagg gcgtgcccag     1200
agctgagccg ggcaccgagg cccggagaca ctatgatgaa ggcgttcgga tgggcagcct     1260
ggggctgttc ctgcagtgcg ccatctccct ggtcttctct ctggtcatgg accggctggt     1320
gcagcgattc ggcactcgag cagtctattt ggccagtgtg gcagctttcc ctgtggctgc     1380
cggtgccaca tgcctgtccc acagtgtggc cgtggtgaca gcttcagccg ccctcaccgg     1440
gttcaccttc tcagccctgc agatcctgcc ctacacactg gcctccctct accaccggga     1500
gaagcaggtg ttcctgccca ataccgagg ggacactgga ggtgctagca gtgaggacag     1560
cctgatgacc agcttcctgc caggccctaa gcctggagct cccttcccta atggacacgt     1620
gggtgctgga ggcagtggcc tgctcccacc tccacccgcg ctctgcgggg cctctgcctg     1680
tgatgtctcc gtacgtgtgg tggtgggtga gccaccgag gccagggtgg ttccgggccg     1740
gggcatctgc ctggacctcg ccatcctgga tagtgccttc ctgctgtccc aggtggcccc     1800
atccctgttt atgggctcca ttgtccagct cagccagtct gtcactgcct atatggtgtc     1860
tgccgcaggc ctgggtctgg tcgccatttta ctttgctaca caggtagtat ttgacaagag     1920
```

-continued

```
cgacttggcc aaatactcag cgtagaaaac ttccagcaca ttggggtgga gggcctgcct      1980
cactgggtcc cagctccccg ctcctgttag ccccatgggg ctgccgggct ggccgccagt      2040
ttctgttgct gccaaagtaa tgtggctctc tgctgccacc ctgtgctgct gaggtgcgta      2100
gctgcacagc tgggggctgg ggcgtccctc tcctctctcc ccagtctcta ggctgcctg       2160
actggaggcc ttccaagggg gtttcagtct ggacttatac agggaggcca gaagggctcc      2220
atgcactgga atgcgggac tctgcaggtg gattacccag gctcagggtt aacagctagc       2280
ctcctagttg agacacacct agagaagggt ttttgggagc tgaataaact cagtcacctg      2340
gtttcccatc tctaagcccc ttaacctgca gcttcgttta atgtagctct tgcatgggag      2400
tttctaggat gaaacactcc tccatgggat ttgaacatat gacttatttg taggggaaga      2460
gtcctgaggg gcaacacaca agaaccaggt cccctcagcc cacagcactg tcttttgct       2520
gatccacccc cctcttacct tttatcagga tgtggcctgt tggtccttct gttgccatca      2580
cagagacaca ggcatttaaa tatttaactt atttatttaa caaagtagaa gggaatccat      2640
tgctagcttt tctgtgttgg tgtctaatat ttgggtaggg tggggatcc ccaacaatca       2700
ggtcccctga gatagctggt cattgggctg atcattgcca gaatcttctt ctcctggggt      2760
ctggcccccc aaaatgccta acccaggacc ttggaaattc tactcatccc aaatgataat      2820
tccaaatgct gttacccaag gttagggtgt tgaaggaagg tagagggtgg ggcttcaggt      2880
ctcaacggct tccctaacca cccctcttct cttggcccag cctggttccc cccacttcca      2940
ctcccctcta ctctctctag gactgggctg atgaaggcac tgcccaaaat ttcccctacc      3000
cccaactttc ccctaccccc aactttcccc accagctcca caaccctgtt tggagctact      3060
gcaggaccag aagcacaaag tgcggtttcc caagcctttg tccatctcag cccccagagt      3120
atatctgtgc ttggggaatc tcacacagaa actcaggagc accccctgcc tgagctaagg      3180
gaggtcttat ctctcagggg gggtttaagt gccgtttgca ataatgtcgt cttatttatt      3240
tagcggggtg aatattttat actgtaagtg agcaatcaga gtataatgtt tatggtgaca      3300
aaattaaagg ctttcttata tgtttaaaaa aaaaaaaaaa aaaaaaaaaa aaaaaaaaa       3360
aaaaaaaara aaaaaaaaa aaaaaaaaa aaaaaataa aaaaaaaaa                     3410
```

<210> SEQ ID NO 111
<211> LENGTH: 1289
<212> TYPE: DNA
<213> ORGANISM: Homo sapien
<400> SEQUENCE: 111

```
agccaggcgt ccctctgcct gcccactcag tggcaacacc cgggagctgt tttgtccttt        60
gtggagcctc agcagttccc tctttcagaa ctcactgcca agagccctga acaggagcca       120
ccatgcagtg cttcagcttc attaagacca tgatgatcct cttcaatttg ctcatctttc       180
tgtgtggtgc agccctgttg gcagtgggca tctggtgtc aatcgatggg gcatcctttc        240
tgaagatctt cggccactg tcgtccagtc catgcagtt tgtcaacgtg gctacttcc          300
tcatcgcagc cggcgttgtg gtctttgctc ttggtttcct gggctgctat ggtgctaaga      360
ctgagagcaa gtgtgccctc gtgacgttct tcttcatcct cctcctcatc ttcattgctg      420
aggttgcagc tgctgtggtc gccttggtgt acaccacaat ggctgagcac ttcctgacgt      480
tgctggtagt gcctgccatc aagaaagatt atgttcccag gaagacttc actcaagtgt       540
ggaacaccac catgaaaggg ctcaagtgct gtggcttcac caactatacg gattttgagg      600
actcacccta cttcaaagag aacagtgcct ttcccccatt ctgttgcaat gacaacgtca      660
```

```
ccaacacagc caatgaaacc tgcaccaagc aaaaggctca cgaccaaaaa gtagagggtt      720
gcttcaatca gcttttgtat gacatccgaa ctaatgcagt caccgtgggt ggtgtggcag      780
ctggaattgg gggcctcgag ctggctgcca tgattgtgtc catgtatctg tactgcaatc      840
tacaataagt ccacttctgc ctctgccact actgctgcca catgggaact gtgaagaggc      900
accctggcaa gcagcagtga ttgggggagg ggacaggatc taacaatgtc acttgggcca      960
gaatggacct gcccttctg ctccagactt ggggctagat agggaccact ccttttagcg     1020
atgcctgact ttccttccat tggtgggtgg atgggtgggg ggcattccag agcctctaag     1080
gtagccagtt ctgttgccca ttcccccagt ctattaaacc cttgatatgc ccctaggcc      1140 tagtggtgat cccagtgctc tactggggga tgagagaaag gcattttata gcctgggcat     1200
aagtgaaatc agcagagcct ctggtggat gtgtagaagg cacttcaaaa tgcataaacc     1260
tgttacaatg ttaaaaaaaa aaaaaaaaa                                       1289
```

<210> SEQ ID NO 112
<211> LENGTH: 315
<212> TYPE: PRT
<213> ORGANISM: Homo sapien

<400> SEQUENCE: 112

```
Met Val Phe Thr Val Arg Leu Leu His Ile Phe Thr Val Asn Lys Gln
 1               5                   10                  15

Leu Gly Pro Lys Ile Val Ile Val Ser Lys Met Met Lys Asp Val Phe
                20                  25                  30

Phe Phe Leu Phe Phe Leu Gly Val Trp Leu Val Ala Tyr Gly Val Ala
            35                  40                  45

Thr Glu Gly Leu Leu Arg Pro Arg Asp Ser Asp Phe Pro Ser Ile Leu
        50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Arg Gln
            180                 185                 190

Leu Cys Arg Arg Pro Arg Ser Pro Gln Pro Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255
```

```
Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
            275                 280                 285

Trp Val Ala Glu Ala Leu Ser Arg Ser Ala Leu Leu Pro Pro Gly Gly
            290                 295                 300

Pro Pro Pro Pro Asp Leu Pro Gly Ser Lys Asp
305                 310                 315

<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Leu Arg His Arg Lys Ala
 1               5                  10                  15

Gln Leu Leu Val Asn Leu Leu Thr Phe Gly Leu Glu Val Cys Leu
            20                  25                  30

Ala Ala Gly Ile Thr Tyr Val Pro Pro Leu Leu Leu Glu Val Gly Val
            35                  40                  45

Glu Glu Lys Phe Met Thr Met Val Leu Gly Ile Gly Pro Val Leu Gly
 50                  55                  60

Leu Val Cys Val Pro Leu Leu Gly Ser Ala Ser Asp His Trp Arg Gly
 65                  70                  75                  80

Arg Tyr Gly Arg Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
            100                 105                 110

Leu Cys Pro Asp Pro Arg Pro Leu Glu Leu Ala Leu Leu Ile Leu Gly
            115                 120                 125

Val Gly Leu Leu Asp Phe Cys Gly Gln Val Cys Phe Thr Pro Leu Glu
            130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
            195                 200                 205

Thr Cys Val Ala Ala Thr Leu Leu Val Ala Glu Ala Ala Leu Gly
            210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
            275                 280                 285

Thr Leu Phe Tyr Thr Asp Phe Val Gly Glu Gly Leu Tyr Gln Gly Val
            290                 295                 300

Pro Arg Ala Glu Pro Gly Thr Glu Ala Arg Arg His Tyr Asp Glu Gly
305                 310                 315                 320
```

```
Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
            340                 345                 350

Ala Val Tyr Leu Ala Ser Val Ala Ala Phe Pro Val Ala Ala Gly Ala
            355                 360                 365

Thr Cys Leu Ser His Ser Val Ala Val Thr Ala Ser Ala Ala Leu
            370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
                435                 440                 445

Gly Gly Ser Gly Leu Leu Pro Pro Pro Ala Leu Cys Gly Ala Ser
            450                 455                 460

Ala Cys Asp Val Ser Val Arg Val Val Gly Glu Pro Thr Glu Ala
465                 470                 475                 480

Arg Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
            515                 520                 525

Gly Leu Gly Leu Val Ala Ile Tyr Phe Ala Thr Gln Val Val Phe Asp
            530                 535                 540

Lys Ser Asp Leu Ala Lys Tyr Ser Ala
545                 550

<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
 1               5                  10                  15

Leu Ile Phe Leu Cys Gly Ala Ala Leu Leu Ala Val Gly Ile Trp Val
            20                  25                  30

Ser Ile Asp Gly Ala Ser Phe Leu Lys Ile Phe Gly Pro Leu Ser Ser
        35                  40                  45

Ser Ala Met Gln Phe Val Asn Val Gly Tyr Phe Leu Ile Ala Ala Gly
    50                  55                  60

Val Val Val Phe Ala Leu Gly Phe Leu Gly Cys Tyr Gly Ala Lys Thr
65                  70                  75                  80

Glu Ser Lys Cys Ala Leu Val Thr Phe Phe Ile Leu Leu Leu Ile
                85                  90                  95

Phe Ile Ala Glu Val Ala Ala Ala Val Val Ala Leu Val Tyr Thr Thr
            100                 105                 110

Met Ala Glu His Phe Leu Thr Leu Leu Val Val Pro Ala Ile Lys Lys
            115                 120                 125

Asp Tyr Gly Ser Gln Glu Asp Phe Thr Gln Val Trp Asn Thr Thr Met
```

```
            130                 135                 140
Lys Gly Leu Lys Cys Cys Gly Phe Thr Asn Tyr Thr Asp Phe Glu Asp
145                 150                 155                 160

Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
        195                 200                 205

Arg Thr Asn Ala Val Thr Val Gly Gly Val Ala Ala Gly Ile Gly Gly
    210                 215                 220

Leu Glu Leu Ala Ala Met Ile Val Ser Met Tyr Leu Tyr Cys Asn Leu
225                 230                 235                 240

Gln
```

<210> SEQ ID NO 115
<211> LENGTH: 366
<212> TYPE: DNA
<213> ORGANISM: Homo sapien

<400> SEQUENCE: 115

```
gctctttctc tcccctcctc tgaatttaat tctttcaact tgcaatttgc aaggattaca      60
catttcactg tgatgtatat tgtgttgcaa aaaaaaaaa gtgtctttgt ttaaaattac     120
ttggtttgtg aatccatctt gctttttccc cattggaact agtcattaac ccatctctga     180
actggtagaa aaacatctga agagctagtc tatcagcatc tgacaggtga attggatggt     240
tctcagaacc atttcaccca gacagcctgt ttctatcctg tttaataaat tagtttgggt     300
tctctacatg cataacaaac cctgctccaa tctgtcacat aaaagtctgt gacttgaagt     360
ttagtc                                                                366
```

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116

```
acaaagatga accatttcct atattatagc aaaattaaaa tctacccgta ttctaatatt      60
gagaaatgag atnaaacaca atnttataaa gtctacttag agaagatcaa gtgacctcaa     120
agactttact attttcatat tttaagacac atgatttatc ctattttagt aacctggttc     180
atacgttaaa caaggataaa tgtgaacagc agagaggatt tgttggcaga aaatctatgt     240
tcaatctnga actatctana tcacagacat ttctattcct tt                       282
```

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117

```
acacatgtcg cttcactgcc ttcttagatg cttctggtca acatanagga acagggacca      60
```

```
tatttatcct ccctcctgaa acaattgcaa ataanacaa aatatatgaa acaattgcaa      120
aataaggcaa aatatatgaa acaacaggtc tcgagatatt ggaaatcagt caatgaagga      180
tactgatccc tgatcactgt cctaatgcag gatgtgggaa acagatgagg tcacctctgt     240
gactgcccca gcttactgcc tgtagagagt ttctangctg cagttcagac agggagaaat     300
tgggt                                                                 305
```

<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118

```
accaaggtgt ntgaatctct gacgtgggga tctctgattc ccgcacaatc tgagtggaaa      60
aantcctggg t                                                          71
```

<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119

```
actccggttg gtgtcagcag cacgtggcat tgaacatngc aatgtggagc ccaaaccaca      60
gaaaatgggg tgaaattggc caactttcta tnaacttatg ttggcaantt tgccaccaac     120
agtaagctgg cccttctaat aaaagaaaat tgaaaggttt ctcactaanc ggaattaant     180
aatggantca aganactccc aggcctcagc gt                                   212
```

<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120

```
actcgttgca natcaggggc cccccagagt caccgttgca ggagtccttc tggtcttgcc      60
ctccgccggc gcagaacatg ctggggtggt                                      90
```

<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121

```
tgtancgtga anacgacaga nagggttgtc aaaaatggag aanccttgaa gtcattttga      60
gaataagatt tgctaaaaga tttggggcta aaacatggtt attgggagac atttctgaag     120
```

```
atatncangt aaattangga atgaattcat ggttcttttg ggaattcctt tacgatngcc      180
agcatanact tcatgtgggg atancagcta cccttgta                             218
```

<210> SEQ ID NO 122
<211> LENGTH: 171
<212> TYPE: DNA
<213> ORGANISM: Homo sapien

<400> SEQUENCE: 122

```
tagggtgta tgcaactgta aggacaaaaa ttgagactca actggcttaa ccaataaagg      60
catttgttag ctcatggaac aggaagtcgg atggtggggc atcttcagtg ctgcatgagt     120
caccaccccg gcggggtcat ctgtgccaca ggtccctgtt gacagtgcgg t              171
```

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123

```
tgtagcgtga agacnacaga atggtgtgtg ctgtgctatc caggaacaca tttattatca     60
ttatcaanta ttgtgt                                                     76
```

<210> SEQ ID NO 124
<211> LENGTH: 131
<212> TYPE: DNA
<213> ORGANISM: Homo sapien

<400> SEQUENCE: 124

```
accttccccc aaggccaatg tcctgtgtgc taactggccg gctgcaggac agctgcaatt     60
caatgtgctg ggtcatatgg aggggaggag actctaaaat agccaatttt attctcttgg    120
ttaagatttg t                                                         131
```

<210> SEQ ID NO 125
<211> LENGTH: 432
<212> TYPE: DNA
<213> ORGANISM: Homo sapien

<400> SEQUENCE: 125

```
actttatcta ctggctatga aatagatggt ggaaaattgc gttaccaact ataccactgg     60
cttgaaaaag aggtgatagc tcttcagagg acttgtgact tttgctcaga tgctgaagaa    120
ctacagtctg catttggcag aaatgaagat gaatttggat taaatgagga tgctgaagat    180
ttgcctcacc aaacaaaagt gaaacaactg agagaaaatt tcaggaaaaa agacagtgg    240 ctcttgaagt atcagtcact tttgagaatg tttcttagtt actgcatact tcatggatcc    300
catggtgggg gtcttgcatc tgtaagaatg gaattgattt tgcttttgca agaatctcag    360
caggaaacat cagaaccact attttctagc cctctgtcag agcaaacctc agtgcctctc    420
ctctttgctt gt                                                        432
```

<210> SEQ ID NO 126
<211> LENGTH: 112
<212> TYPE: DNA
<213> ORGANISM: Homo sapien

<400> SEQUENCE: 126

```
acacaacttg aatagtaaaa tagaaactga gctgaaattt ctaattcact ttctaaccat    60
agtaagaatg atatttcccc ccagggatca ccaaatattt ataaaaattt gt           112
```

<210> SEQ ID NO 127
<211> LENGTH: 54
<212> TYPE: DNA
<213> ORGANISM: Homo sapien

<400> SEQUENCE: 127

```
accacgaaac cacaaacaag atggaagcat caatccactt gccaagcaca gcag          54
```

<210> SEQ ID NO 128
<211> LENGTH: 323
<212> TYPE: DNA
<213> ORGANISM: Homo sapien

<400> SEQUENCE: 128

```
acctcattag taattgtttt gttgtttcat ttttttctaa tgtctcccct ctaccagctc    60
acctgagata acagaatgaa aatggaagga cagccagatt tctcctttgc tctctgctca   120
ttctctctga agtctaggtt acccatttg gggacccatt ataggcaata aacacagttc    180
ccaaagcatt tggacagttt cttgttgtgt tttagaatgg ttttcctttt tcttagcctt   240
ttcctgcaaa aggctcactc agtcccttgc ttgctcagtg gactgggctc cccagggcct   300
aggctgcctt cttttccatg tcc                                          323
```

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129

```
acatacatgt gtgtatattt ttaaatatca cttttgtatc actctgactt tttagcatac    60
tgaaaacaca ctaacataat ttntgtgaac catgatcaga tacaacccaa atcattcatc   120
tagcacattc atctgtgata naaagatagg tgagtttcat ttccttcacg ttggccaatg   180
gataaacaaa gt                                                      192
```

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130

```
cccttttta tggaatgagt agactgtatg tttgaanatt tanccacaac ctctttgaca     60
tataatgacg caacaaaaag gtgctgttta gtcctatggt tcagtttatg cccctgacaa   120
gtttccattg tgtttgccg atcttctggc taatcgtggt atcctccatg ttattagtaa    180
ttctgtattc cattttgtta acgcctggta gatgtaacct gctangaggc taactttata   240
cttatttaaa agctcttatt ttgtggtcat taaaatggca atttatgtgc agcactttat   300
tgcagcagga agcacgtgtg ggttggttgt aaagctcttt gctaatctta aaaagtaatg   360
```

<210> SEQ ID NO 131
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

| | | | | | |
|---|---|---|---|---|---|
| cttttttgaaa | gatcgtgtcc | actcctgtgg | acatcttgtt | ttaatggagt | ttcccatgca | 60 |
| gtangactgg | tatggttgca | gctgtccaga | taaaaacatt | tgaagagctc | caaaatgaga | 120 |
| gttctcccag | gttcgccctg | ctgctccaag | tctcagcagc | agcctctttt | aggaggcatc | 180 |
| ttctgaacta | gattaaggca | gcttgtaaat | ctgatgtgat | ttggtttatt | atccaactaa | 240 |
| cttccatctg | ttatcactgg | agaaagccca | gactccccan | gacnggtacg | gattgtgggc | 300 |
| atanaaggat | tgggtgaagc | tggcgttgtg | gt | | | 332 |

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

| | | | | | |
|---|---|---|---|---|---|
| acttttgcca | ttttgtatat | ataaacaatc | ttgggacatt | ctcctgaaaa | ctaggtgtcc | 60 |
| agtggctaag | agaactcgat | ttcaagcaat | tctgaaagga | aaaccagcat | gacacagaat | 120 |
| ctcaaattcc | caaacagggg | ctctgtggga | aaaatgaggg | aggacctttg | tatctcgggt | 180 |
| tttagcaagt | taaaatgaan | atgacaggaa | aggcttattt | atcaacaaag | agaagagttg | 240 |
| ggatgcttct | aaaaaaaact | ttggtagaga | aaataggaat | gctnaatcct | agggaagcct | 300 |
| gtaacaatct | acaattggtc | ca | | | | 322 |

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

| | | | | | |
|---|---|---|---|---|---|
| acaagccttc | acaagtttaa | ctaaattggg | attaatcttt | ctgtanttat | ctgcataatt | 60 |
| cttgtttttc | tttccatctg | gctcctgggt | tgacaatttg | tggaaacaac | tctattgcta | 120 |
| ctatttaaaa | aaaatcacaa | atctttccct | ttaagctatg | ttnaattcaa | actattcctg | 180 |
| ctattcctgt | tttgtcaaag | aaattatatt | tttcaaaata | tgtntatttg | tttgatgggt | 240 |
| cccacgaaac | actaataaaa | accacagaga | ccagcctg | | | 278 |

<210> SEQ ID NO 134
<211> LENGTH: 121
<212> TYPE: DNA
<213> ORGANISM: Homo sapien
<220> FEATURE:
<221> NAME/KEY: misc_feature

```
<222> LOCATION: (1)...(121)
<223> OTHER INFORMATION: n = A,T,C or G

<400> SEQUENCE: 134
gtttanaaaa cttgtttagc tccatagagg aaagaatgtt aaactttgta ttttaaaaca      60
tgattctctg aggttaaact tggttttcaa atgttatttt tacttgtatt ttgcttttgg     120
t                                                                     121

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135
acttanaacc atgcctagca catcagaatc cctcaaagaa catcagtata atcctatacc      60
atancaagtg gtgactggtt aagcgtgcga caaaggtcag ctggcacatt acttgtgtgc    120
aaacttgata cttttgttct aagtaggaac tagtatacag tncctaggan tggtactcca    180
gggtgccccc caactcctgc agccgctcct ctgtgccagn ccctgnaagg aactttcgct    240
ccacctcaat caagccctgg gccatgctac ctgcaattgg ctgaacaaac gtttgctgag    300
ttcccaagga tgcaaagcct ggtgctcaac tcctggggcg tcaactcagt               350

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136
tgtaccgtga agacgacaga agttgcatgg cagggacagg gcaggccga ggccagggtt      60 gctgtgattg tatccgaata ntcctcgtga gaaaagataa tgagatgacg tgagcagcct    120
gcagacttgt gtctgccttc aanaagccag acaggaaggc cctgcctgcc ttggctctga    180
cctggcggcc agccagccag ccacaggtgg gcttcttcct tttgtggtga caacnccaag    240
aaaactgcag aggcccaggg tcaggtgtna gtgggtangt gaccataaaa caccaggtgc    300
tcccaggaac ccgggcaaag gccatcccca cctacagcca gcatgcccac tggcgtgatg    360
ggtgcagang gatgaagcag ccagntgttc tgctgtggt                            399

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137
actggtgtgg tnggggtga tgctggtggt anaagttgan gtgacttcan gatggtgtgt      60
ggaggaagtg tgtgaacgta gggatgtaga ngttttggcc gtgctaaatg agcttcggga    120
ttggctggtc ccactggtgg tcactgtcat tggtggggtt cctgt                    165
```

<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138

| | | | | | |
|---|---|---|---|---|---|
| actcactgga | atgccacatt | cacaacagaa | tcagaggtct | gtgaaaacat | taatggctcc | 60 |
| ttaacttctc | cagtaagaat | cagggacttg | aaatggaaac | gttaacagcc | acatgcccaa | 120 |
| tgctgggcag | tctcccatgc | cttccacagt | gaaagggctt | gagaaaaatc | acatccaatg | 180 |
| tcatgtgttt | ccagccacac | caaaaggtgc | ttggggtgga | gggctggggg | catananggt | 240 |
| cangcctcag | gaagcctcaa | gttccattca | gctttgccac | tgtacattcc | ccatntttaa | 300 |
| aaaaactgat | gccttttttt | tttttttttg | taaaattc | | | 338 |

<210> SEQ ID NO 139
<211> LENGTH: 382
<212> TYPE: DNA
<213> ORGANISM: Homo sapien

<400> SEQUENCE: 139

| | | | | | |
|---|---|---|---|---|---|
| gggaatcttg | gttttggca | tctggtttgc | ctatagccga | ggccactttg | acagaacaaa | 60 |
| gaaagggact | tcgagtaaga | aggtgattta | cagccagcct | agtgcccgaa | gtgaaggaga | 120 |
| attcaaacag | acctcgtcat | tcctggtgtg | agcctggtcg | gctcaccgcc | tatcatctgc | 180 |
| atttgcctta | ctcaggtgct | accggactct | ggcccctgat | gtctgtagtt | tcacaggatg | 240 |
| ccttatttgt | cttctacacc | ccacagggcc | ccctacttct | tcggatgtgt | ttttaataat | 300 |
| gtcagctatg | tgccccatcc | tccttcatgc | cctccctccc | tttcctacca | ctgctgagtg | 360 |
| gcctggaact | tgtttaaagt | gt | | | | 382 |

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140

| | | | | | |
|---|---|---|---|---|---|
| accaaanctt | ctttctgttg | tgttngattt | tactataggg | gtttngcttn | ttctaaanat | 60 |
| acttttcatt | taacanctttt | tgttaagtgt | caggctgcac | tttgctccat | anaattattg | 120 |
| ttttcacatt | tcaacttgta | tgtgtttgtc | tcttanagca | ttggtgaaat | cacatatttt | 180 |
| atattcagca | taaaggagaa | | | | | 200 |

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141

| | | | | | |
|---|---|---|---|---|---|
| actttatttt | caaacactc | atatgttgca | aaaaacacat | agaaaaataa | agtttggtgg | 60 |

```
gggtgctgac taaacttcaa gtcacagact tttatgtgac agattggagc agggtttgtt    120
atgcatgtag agaacccaaa ctaatttatt aaacaggata gaaacaggct gtctgggtga    180
aatggttctg agaaccatcc aattcacctg tcagatgctg atanactagc tcttcagatg    240
tttttctacc agttcagaga tnggttaatg actanttcca atggggaaaa agcaagatgg    300
attcacaaac caagtaattt aaacaaaga cactt                                335

<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142
accaggttaa tattgccaca tatatccttt ccaattgcgg gctaaacaga cgtgtattta     60
gggttgttta aagacaaccc agcttaatat caagagaaat tgtgaccttt catggagtat    120
ctgatggaga aaacactgag ttttgacaaa tcttatttta ttcagatagc agtctgatca    180
cacatggtcc aacaacactc aaataataaa tcaaatatna tcagatgtta aagattggtc    240
ttcaaacatc atagccaatg atgccccgct tgcctataat ctctccgaca taaaaccaca    300
tcaacacctc agtggccacc aaaccattca gcacagcttc cttaactgtg agctgtttga    360
agctaccagt ctgagcacta ttgactatnt ttttcangct ctgaatagct ctagggatct    420
cagcangggt gggaggaacc agctcaacct tggcgtant                          459

<210> SEQ ID NO 143
<211> LENGTH: 140
<212> TYPE: DNA
<213> ORGANISM: Homo sapien

<400> SEQUENCE: 143
acatttcctt ccaccaagtc aggactcctg gcttctgtgg gagttcttat cacctgaggg     60
aaatccaaac agtctctcct agaaggaat agtgtcacca accccaccca tctccctgag    120
accatccgac ttccctgtgt                                                140

<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144
acttcagtaa caacatacaa taacaacatt aagtgtatat tgccatcttt gtcattttct     60
atctatacca ctctccttc tgaaaacaan aatcactanc caatcactta tacaaatttg    120
aggcaattaa tccatatttg ttttcaataa ggaaaaaaag atgt                     164

<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
```

<223> OTHER INFORMATION: n = A,T,C or G

<400> SEQUENCE: 145

| acgtagacca | tccaactttg | tatttgtaat | ggcaaacatc | cagnagcaat | tcctaaacaa | 60 |
| actggagggt | atttataccc | aattatccca | ttcattaaca | tgccctcctc | ctcaggctat | 120 |
| gcaggacagc | tatcataagt | cggcccaggc | atccagatac | taccatttgt | ataaacttca | 180 |
| gtaggggagt | ccatccaagt | gacaggtcta | atcaaaggag | gaaatggaac | ataagcccag | 240 |
| tagtaaaatn | ttgcttagct | gaaacagcca | caaaagactt | accgccgtgg | tgattaccat | 300 |
| caa | | | | | | 303 |

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

| actgcagctc | aattagaagt | ggtctctgac | tttcatcanc | ttctccctgg | gctccatgac | 60 |
| actggcctgg | agtgactcat | tgctctggtt | ggttgagaga | gctcctttgc | caacaggcct | 120 |
| ccaagtcagg | gctgggattt | gtttcctttc | cacattctag | caacaatatg | ctggccactt | 180 |
| cctgaacagg | gagggtggga | ggagccagca | tggaacaagc | tgccactttc | taaagtagcc | 240 |
| agacttgccc | ctgggcctgt | cacacctact | gatgaccttc | tgtgcctgca | ggatggaatg | 300 |
| tagggggtgag | ctgtgtgact | ctatggt | | | | 327 |

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

| acattgtttt | tttgagataa | agcattgana | gagctctcct | taacgtgaca | caatggaagg | 60 |
| actggaacac | atacccacat | ctttgttctg | agggataatt | ttctgataaa | gtcttgctgt | 120 |
| atattcaagc | acatatgtta | tatattattc | agttccatgt | ttatagccta | gtt | 173 |

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

| acaaccactt | tatctcatcg | aattttaac | ccaaactcac | tcactgtgcc | tttctatcct | 60 |
| atgggatata | ttatttgatg | ctccatttca | tcacacatat | atgaataata | cactcatact | 120 |
| gccctactac | ctgctgcaat | aatcacattc | ccttcctgtc | ctgaccctga | agccattggg | 180 |
| gtggtcctag | tggccatcag | tccangcctg | caccttgagc | ccttgagctc | cattgctcac | 240 |
| nccancccac | ctcaccgacc | ccatcctctt | acacagctac | ctccttgctc | tctaacccca | 300 |

```
tagattatnt ccaaattcag tcaattaagt tactattaac actctacccg acatgtccag    360
caccactggt aagccttctc cagccaacac acacacacac acacncacac acacacatat    420
ccaggcacag gctacctcat cttcacaatc accccttaa ttaccatgct atggtgg        477
```

<210> SEQ ID NO 149
<211> LENGTH: 207
<212> TYPE: DNA
<213> ORGANISM: Homo sapien

<400> SEQUENCE: 149

```
acagttgtat tataatatca agaaataaac ttgcaatgag agcatttaag agggaagaac    60
taacgtattt tagagagcca aggaaggttt ctgtggggag tgggatgtaa ggtggggcct    120
gatgataaat aagagtcagc caggtaagtg ggtggtgtgg tatgggcaca gtgaagaaca    180
tttcaggcag agggaacagc agtgaaa                                        207
```

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150

```
accttgattt cattgctgct ctgatggaaa cccaactatc taatttagct aaaacatggg    60
cacttaaatg tggtcagtgt ttggacttgt taactantgg catctttggg t             111
```

<210> SEQ ID NO 151
<211> LENGTH: 196
<212> TYPE: DNA
<213> ORGANISM: Homo sapien

<400> SEQUENCE: 151

```
agcgcggcag gtcatattga acattccaga tacctatcat tactcgatgc tgttgataac    60
agcaagatgg ctttgaactc agggtcacca ccagctattg gaccttacta tgaaaaccat    120
ggataccaac cggaaaaccc ctatcccgca cagcccactg tggtccccac tgtctacgag    180
gtgcatccgg ctcagt                                                    196
```

<210> SEQ ID NO 152
<211> LENGTH: 132
<212> TYPE: DNA
<213> ORGANISM: Homo sapien

<400> SEQUENCE: 152

```
acagcacttt cacatgtaag aagggagaaa ttcctaaatg taggagaaag ataacagaac    60
cttccccttt tcatctagtg gtggaaacct gatgctttat gttgacagga atagaaccag    120
gagggagttt gt                                                        132
```

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153

```
acaanaccca nganaggcca ctggccgtgg tgtcatggcc tccaaacatg aaagtgtcag      60
cttctgctct tatgtcctca tctgacaact ctttaccatt tttatcctcg ctcagcagga     120
gcacatcaat aaagtccaaa gtcttggact tggccttggc ttggaggaag tcatcaacac     180
cctggctagt gagggtgcgg cgccgctcct ggatgacgac atctgtgaag tcgtgcacca     240
gtctgcaggc cctgtggaag cgccgtccac acggagtnag gaatt                     285
```

<210> SEQ ID NO 154
<211> LENGTH: 333
<212> TYPE: DNA
<213> ORGANISM: Homo sapien

<400> SEQUENCE: 154

```
accacagtcc tgttgggcca gggcttcatg acccttctg tgaaaagcca tattatcacc       60
accccaaatt tttccttaaa tatctttaac tgaagggtc agcctcttga ctgcaaagac      120
cctaagccgg ttacacagct aactcccact ggccctgatt tgtgaaattg ctgctgcctg     180
attggcacag gagtcgaagg tgttcagctc ccctcctccg tggaacgaga ctctgatttg     240
agtttcacaa attctcgggc cacctcgtca ttgctcctct gaaataaaat ccggagaatg     300
gtcaggcctg tctcatccat atggatcttc cgg                                   333
```

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155

```
actggaaata ataaaaccca catcacagtg ttgtgtcaaa gatcatcagg gcatggatgg       60
gaaagtgctt tgggaactgt aaagtgccta acacatgatc gatgattttt gttataatat     120
ttgaatcacg gtgcatacaa actctcctgc ctgctcctcc tgggcccag ccccagcccc      180
atcacagctc actgctctgt tcatccaggc ccagcatgta gtggctgatt cttcttggct     240
gcttttagcc tccanaagtt tctctgaagc caaccaaacc tctangtgta aggcatgctg     300
gccctggt                                                               308
```

<210> SEQ ID NO 156
<211> LENGTH: 295
<212> TYPE: DNA
<213> ORGANISM: Homo sapien

<400> SEQUENCE: 156

```
accttgctcg gtgcttggaa catattagga actcaaaata tgagatgata acagtgccta      60
ttattgatta ctgagagaac tgttagacat ttagttgaag atttctaca caggaactga     120
gaataggaga ttatgtttgg ccctcatatt ctctcctatc ctccttgcct cattctatgt     180
ctaatatatt ctcaatcaaa taaggttagc ataatcagga aatcgaccaa ataccaatat     240
aaaaccagat gtctatcctt aagattttca aatagaaaac aaattaacag actat         295
```

<210> SEQ ID NO 157
<211> LENGTH: 126
<212> TYPE: DNA
<213> ORGANISM: Homo sapien

<400> SEQUENCE: 157

| acaagtttaa atagtgctgt cactgtgcat gtgctgaaat gtgaaatcca ccacatttct | 60 |
| gaagagcaaa acaaattctg tcatgtaatc tctatcttgg gtcgtgggta tatctgtccc | 120 |
| cttagt | 126 |

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158

| acccactggt cttggaaaca cccatcctta atacgatgat ttttctgtcg tgtgaaaatg | 60 |
| aanccagcag gctgcccta gtcagtcctt ccttccagag aaaaagagat ttgagaaagt | 120 |
| gcctgggtaa ttcaccatta atttcctccc ccaaactctc tgagtcttcc cttaatattt | 180 |
| ctggtggttc tgaccaaagc aggtcatggt ttgttgagca tttgggatcc cagtgaagta | 240 |
| natgtttgta gccttgcata cttagccctt cccacgcaca aacggagtgg cagagtggtg | 300 |
| ccaaccctgt tttcccagtc cacgtagaca gattcacagt gcggaattct ggaagctgga | 360 |
| nacagacggg ctctttgcag agccgggact ctgagangga catgagggcc tctgcctctg | 420 |
| tgttcattct ctgatgtcct gt | 442 |

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159

| acttccaggt aacgttgttg tttccgttga gcctgaactg atgggtgacg ttgtaggttc | 60 |
| tccaacaaga actgaggttg cagagcgggt agggaagagt gctgttccag ttgcacctgg | 120 |
| gctgctgtgg actgttgttg attcctcact acggcccaag gttgtggaac tggcanaaag | 180 |
| gtgtgttgtt gganttgagc tcgggcggct gtggtaggtt gtgggctctt caacaggggc | 240 |
| tgctgtggtg ccgggangtg aangtgttgt gtcacttgag cttggccagc tctggaaagt | 300 |
| antanattct tcctgaaggc cagcgcttgt ggagctggca ngggtcantg ttgtgtgtaa | 360 |
| cgaaccagtg ctgctgtggg tgggtgtana tcctccacaa agcctgaagt tatggtgtcn | 420 |
| tcaggtaana atgtggtttc agtgtccctg ggcngctgtg gaaggttgta nattgtcacc | 480 |
| aagggaataa gctgtggt | 498 |

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160

-continued

| | |
|---|---|
| acctgcatcc agcttccctg ccaaactcac aaggagacat caacctctag acagggaaac | 60 |
| agcttcagga tacttccagg agacagagcc accagcagca aaacaaatat tcccatgcct | 120 |
| ggagcatggc atagaggaag ctganaaatg tggggtctga ggaagccatt tgagtctggc | 180 |
| cactagacat ctcatcagcc acttgtgtga agagatgccc catgacccca gatgcctctc | 240 |
| ccacccttac ctccatctca cacacttgag ctttccactc tgtataattc taacatcctg | 300 |
| gagaaaaatg gcagtttgac cgaacctgtt cacaacggta gaggctgatt tctaacgaaa | 360 |
| cttgtagaat gaagcctgga | 380 |

<210> SEQ ID NO 161
<211> LENGTH: 114
<212> TYPE: DNA
<213> ORGANISM: Homo sapien

<400> SEQUENCE: 161

| | |
|---|---|
| actccacatc ccctctgagc aggcggttgt cgttcaaggt gtatttggcc ttgcctgtca | 60 |
| cactgtccac tggcccctta tccacttggt gcttaatccc tcgaaagagc atgt | 114 |

<210> SEQ ID NO 162
<211> LENGTH: 177
<212> TYPE: DNA
<213> ORGANISM: Homo sapien

<400> SEQUENCE: 162

| | |
|---|---|
| actttctgaa tcgaatcaaa tgatacttag tgtagtttta atatcctcat atatatcaaa | 60 |
| gttttactac tctgataatt ttgtaaacca ggtaaccaga acatccagtc atacagcttt | 120 |
| tggtgatata taacttggca ataacccagt ctggtgatac ataaaactac tcactgt | 177 |

<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163

| | |
|---|---|
| catttataca gacaggcgtg aagacattca cgacaaaaac gcgaaattct atcccgtgac | 60 |
| canagaaggc agctacggct actcctacat cctggcgtgg gtggccttcg cctgcacctt | 120 |
| catcagcggc atgatgt | 137 |

<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164

| | |
|---|---|
| cttatcacaa tgaatgttct cctgggcagc gttgtgatct ttgccacctt cgtgacttta | 60 |
| tgcaatgcat catgctattt catacctaat gagggagttc caggagattc aaccaggaaa | 120 |
| tgcatggatc tcaaaggaaa caaacaccca ataaactcgg agtggcagac tgacaactgt | 180 |
| gagacatgca cttgctacga aacagaaatt tcatgttgca cccttgtttc tacacctgtg | 240 |
| ggttatgaca agacaactg ccaaagaatc ttcaagaagg aggactgcaa gtatatcgtg | 300 |

```
gtggagaaga aggacccaaa aaagacctgt tctgtcagtg aatggataat ctaatgtgct     360
tctagtaggc acagggctcc caggccaggc ctcattctcc tctggcctct aatagtcaat     420
gattgtgtag ccatgcctat cagtaaaaag atntttgagc aaacacttt                469
```

<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165

```
acagtttttt atanatatcg acattgccgg cacttgtgtt cagtttcata aagctggtgg      60
atccgctgtc atccactatt ccttggctag agtaaaaatt attcttatag cccatgtccc     120
tgcaggccgc ccgcccgtag ttctcgttcc agtcgtcttg gcacacaggg tgccaggact     180
tcctctgaga tgagt                                                     195
```

<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166

```
acatcttagt agtgtggcac atcagggggc catcagggtc acagtcactc atagcctcgc      60
cgaggtcgga gtccacacca ccggtgtagg tgtgctcaat cttgggcttg gcgcccacct     120
ttggagaagg gatatgctgc acacacatgt ccacaaagcc tgtgaactcg ccaaagaatt     180
tttgcagacc agcctgagca agggcggat gttcagcttc agctcctcct tcgtcaggtg     240
gatgccaacc tcgtctangg tccgtgggaa gctggtgtcc acntcaccta caacctgggc     300
gangatctta taaagaggct ccnagataaa ctccacgaaa cttctctggg agctgctagt     360 ngggggccttt ttggtgaact ttc                                            383
```

<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167

```
acagagccag accttggcca taaatgaanc agagattaag actaaacccc aagtcganat      60
tggagcagaa actggagcaa gaagtgggcc tggggctgaa gtagagacca aggccactgc     120
tatanccata cacagagcca actctcaggc caaggcnatg gttggggcag anccagagac     180
tcaatctgan tccaaagtgg tggctggaac actggtcatg acanaggcag tgactctgac     240 tgangtc                                                              247
```

<210> SEQ ID NO 168
<211> LENGTH: 273
<212> TYPE: DNA

```
<213> ORGANISM: Homo sapien
<220> FEATURE:
<221> NAME/KEY: misc_feature
<222> LOCATION: (1)...(273)
<223> OTHER INFORMATION: n = A,T,C or G

<400> SEQUENCE: 168
acttctaagt tttctagaag tggaaggatt gtantcatcc tgaaaatggg tttacttcaa      60
aatccctcan ccttgttctt cacnactgtc tatactgana gtgtcatgtt tccacaaagg    120
gctgacacct gagcctgnat tttcactcat ccctgagaag ccctttccag tagggtgggc    180
aattcccaac ttccttgcca caagcttccc aggctttctc ccctggaaaa ctccagcttg    240
agtcccagat acactcatgg gctgccctgg gca                                  273

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169
acagccttgg cttccccaaa ctccacagtc tcagtgcaga aagatcatct tccagcagtc      60
agctcagacc agggtcaaag gatgtgacat caacagtttc tggtttcaga acaggttcta    120
ctactgtcaa atgaccccccc atacttcctc aaaggctgtg gtaagttttg cacaggtgag    180
ggcagcagaa aggggtgtant tactgatgga caccatcttc tctgtatact ccacactgac    240
cttgccatgg gcaaaggccc ctaccacaaa acaataggga tcactgctgg gcaccagctc    300
acgcacatca ctgacaaccg ggatggaaaa agaantgcca actttcatac atccaactgg    360
aaagtgatct gatactggat tcttaattac cttcaaaagc ttctgggggc catcagctgc    420
tcgaacactg a                                                           431

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170
acctgtgggc tgggctgtta tgcctgtgcc ggctgctgaa agggagttca gaggtggagc      60
tcaaggagct ctgcaggcat tttgccaanc ctctccanag canagggagc aacctacact    120
ccccgctaga aagacaccag attggagtcc tgggaggggg agttggggtg ggcatttgat    180
gtatacttgt cacctgaatg aangagccag agaggaanga gacgaanatg anattggcct    240
tcaaagctag gggtctggca ggtgga                                          266

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171
```

-continued

```
ggcagccaaa tcataaacgg cgaggactgc agcccgcact cgcagccctg gcaggcggca      60
ctggtcatgg aaaacgaatt gttctgctcg ggcgtcctgg tgcatccgca gtgggtgctg     120
tcagccgcac actgtttcca gaagtgagtg cagagctcct acaccatcgg gctgggcctg     180
cacagtcttg aggccgacca agagccaggg agccagatgg tggaggccag cctctccgta     240
cggcacccag agtacaacag acccttgctc gctaacgacc tcatgctcat caagttggac     300
gaatccgtgt ccgagtctga caccatccgg agcatcagca ttgcttcgca gtgccctacc     360
gcggggaact cttgcctcgt ttctggctgg ggtctgctgg cgaacggcag aatgcctacc     420
gtgctgcagt gcgtgaacgt gtcggtggtg tctgaggagg tctgcagtaa gctctatgac     480
ccgctgtacc accccagcat gttctgcgcc ggcggagggc aagaccagaa ggactcctgc     540
aacggtgact ctgggggggcc cctgatctgc aacgggtact gcagggcct tgtgtctttc     600
ggaaaagccc cgtgtggcca agttggcgtg ccaggtgtct acaccaacct ctgcaaattc     660
actgagtgga tagagaaaac cgtccaggcc agttaactct ggggactggg aacccatgaa     720
attgaccccc aaatacatcc tgcggaagga attcaggaat atctgttccc agcccctcct     780
ccctcaggcc caggagtcca ggcccccagc ccctcctccc tcaaaccaag ggtacagatc     840
cccagccccct cctccctcag acccaggagt ccagaccccc cagcccctcc tccctcagac     900
ccaggagtcc agcccctcct ccctcagacc caggagtcca gacccccag cccctcctcc     960
ctcagaccca gggtccagg ccccaaccc ctcctccctc agactcagag gtccaagccc    1020
ccaacccntc attccccaga cccagaggtc caggtcccag ccctcntcc ctcagaccca    1080
gcggtccaat gccacctaga ctntccctgt acacagtgcc ccttgtggc acgttgaccc    1140
aaccttacca gttggttttt cattttnngt cccttttcccc tagatccaga aataaagttt    1200
aagagaagng caaaaaaaaa aaaaaaaaaa aaaaaaaaa aaaaaaaa                  1248
```

<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

```
Met Val Glu Ala Ser Leu Ser Val Arg His Pro Glu Tyr Asn Arg Pro
  1               5                  10                  15

Leu Leu Ala Asn Asp Leu Met Leu Ile Lys Leu Asp Glu Ser Val Ser
             20                  25                  30

Glu Ser Asp Thr Ile Arg Ser Ile Ser Ile Ala Ser Gln Cys Pro Thr
         35                  40                  45

Ala Gly Asn Ser Cys Leu Val Ser Gly Trp Gly Leu Leu Ala Asn Gly
     50                  55                  60

Arg Met Pro Thr Val Leu Gln Cys Val Asn Val Ser Val Val Ser Glu
 65                  70                  75                  80

Glu Val Cys Ser Lys Leu Tyr Asp Pro Leu Tyr His Pro Ser Met Phe
                 85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125
```

```
Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173

| | | | | | |
|---|---|---|---|---|---|
| ggcagcccgc | actcgcagcc | ctggcaggcg | gcactggtca | tggaaaacga | attgttctgc | 60 |
| tcgggcgtcc | tggtgcatcc | gcagtgggtg | ctgtcagccg | cacactgttt | ccagaactcc | 120 |
| tacaccatcg | ggctgggcct | gcacagtctt | gaggccgacc | aagagccagg | gagccagatg | 180 |
| gtggaggcca | gcctctccgt | acggcaccca | gagtacaaca | gacccttgct | cgctaacgac | 240 |
| ctcatgctca | tcaagttgga | cgaatccgtg | tccgagtctg | acaccatccg | gagcatcagc | 300 |
| attgcttcgc | agtgccctac | cgcggggaac | tcttgcctcg | tttctggctg | ggtctgctg | 360 |
| gcgaacggtg | agctcacggg | tgtgtgtctg | ccctcttcaa | ggaggtcctc | tgcccagtcg | 420 |
| cgggggctga | cccagagctc | tgcgtcccag | gcagaatgcc | taccgtgctg | cagtgcgtga | 480 |
| acgtgtcggt | ggtgtctgag | gaggtctgca | gtaagctcta | tgacccgctg | taccacccca | 540 |
| gcatgttctg | cgccggcgga | gggcaagacc | agaaggactc | ctgcaacggt | gactctgggg | 600 |
| ggcccctgat | ctgcaacggg | tacttgcagg | gccttgtgtc | tttcggaaaa | gccccgtgtg | 660 |
| gccaagttgg | cgtgccaggt | gtctacacca | acctctgcaa | attcactgag | tggatagaga | 720 |
| aaaccgtcca | ggccagttaa | ctctggggac | tgggaaccca | tgaaattgac | ccccaaatac | 780 |
| atcctgcgga | aggaattcag | gaatatctgt | tcccagcccc | tcctccctca | ggcccaggag | 840 |
| tccaggcccc | cagcccctcc | tccctcaaac | caagggtaca | gatccccagc | cctcctccc | 900 |
| tcagacccag | gagtccagac | cccccagccc | ctcctccctc | agacccagga | gtccagcccc | 960 |
| tcctccntca | gacccaggag | tccagacccc | ccagcccctc | tccctcaga | cccagggggtt | 1020 |
| gaggccccca | ccccctcctc | cttcagagtc | agaggtccaa | gcccccaacc | cctcgttccc | 1080 |
| cagacccaga | ggtnnaggtc | ccagcccctc | ttccntcaga | cccagnggtc | caatgccacc | 1140 |
| tagattttcc | ctgnacacag | tgccccccttg | tggnangttg | acccaaccttt | accagttggt | 1200 |
| ttttcatttt | tngtcccttt | ccctagatc | cagaaataaa | gtttaagaga | ngngcaaaaa | 1260 |
| aaaaa | | | | | | 1265 |

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174

| | | | | | |
|---|---|---|---|---|---|
| ggtcagccgc | acactgtttc | cagaagtgag | tgcagagctc | ctacaccatc | gggctgggcc | 60 |
| tgcacagtct | tgaggccgac | caagagccag | ggagccagat | ggtggaggcc | agcctctccg | 120 |
| tacggcaccc | agagtacaac | agaccccttgc | tcgctaacga | cctcatgctc | atcaagttgg | 180 |

```
acgaatccgt gtccgagtct gacaccatcc ggagcatcag cattgcttcg cagtgcccta      240
ccgcggggaa ctcttgcctc gtttctggct ggggtctgct ggcgaacggt gagctcacgg      300
gtgtgtgtct gccctcttca aggaggtcct ctgcccagtc gcggggctg acccagagct       360 ctgcgtccca ggcagaatgc ctaccgtgct gcagtgcgtg aacgtgtcgg tggtgtctga      420
ngaggtctgc antaagctct atgacccgct gtaccacccc ancatgttct cgccggcgg       480 agggcaagac cagaaggact cctgcaacgt gagagagggg aaaggggagg gcaggcgact      540
cagggaaggg tggagaaggg ggagacagag acacacaggg ccgcatggcg agatgcagag      600
atggagagac acacagggag acagtgacaa ctagagagag aaactgagag aaacagagaa      660
ataaacacag gaataaagag aagcaaagga agagagaaac agaaacagac atggggaggc      720
agaaacacac acacatagaa atgcagttga ccttccaaca gcatgggcc tgagggcggt       780 gacctccacc caatagaaaa tcctcttata acttttgact ccccaaaaac ctgactagaa      840
atagcctact gttgacgggg agccttacca ataacataaa tagtcgattt atgcatacgt      900
tttatgcatt catgatatac ctttgttgga attttttgat atttctaagc tacacagttc      960
gtctgtgaat ttttttaaat tgttgcaact ctcctaaaat ttttctgatg tgtttattga     1020
aaaaatccaa gtataagtgg acttgtgcat tcaaaccagg gttgttcaag ggtcaactgt     1080
gtacccagag ggaaacagtg acacagattc atagaggtga aacacgaaga gaaacaggaa     1140
aaatcaagac tctacaaaga ggctgggcag ggtggctcat gcctgtaatc ccagcacttt     1200
gggaggcgag gcaggcagat cacttgaggt aaggagttca agaccagcct ggccaaaatg     1260
gtgaaatcct gtctgtacta aaaatacaaa agttagctgg atatggtggc aggcgcctgt     1320
aatcccagct acttgggagg ctgaggcagg agaattgctt gaatatggga ggcagaggtt     1380
gaagtgagtt gagatcacac cactatactc cagctggggc aacagagtaa gactctgtct     1440 caaaaaaaa aaaaaaaa                                                   1459

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175
gcgcagccct ggcaggcggc actggtcatg gaaaacgaat tgttctgctc gggcgtcctg       60
gtgcatccgc agtgggtgct gtcagccgca cactgtttcc agaactccta caccatcggg      120
ctgggcctgc acagtcttga ggccgaccaa gagccaggga ccagatggt ggaggccagc       180 ctctccgtac ggcacccaga gtacaacaga ctcttgctcg ctaacgacct catgctcatc      240
aagttggacg aatccgtgtc cgagtctgac accatccgga gcatcagcat tgcttcgcag      300
tgccctaccg cggggaactc ttgcctcgtn tctggctggg gtctgctggc aacggcaga      360 atgcctaccg tgctgcactg cgtgaacgtg tcggtggtgt ctgaggangt ctgcagtaag      420
ctctatgacc cgctgtacca ccccagcatg ttctgcgccg cggagggca agaccagaag      480 gactcctgca acggtgactc tgggggccc ctgatctgca acgggtactt gcagggcctt      540
gtgtctttcg gaaaagcccc gtgtggccaa cttggcgtgc caggtgtcta caccaacctc      600
tgcaaattca ctgagtggat agagaaaacc gtccagncca gttaactctg gggactggga      660
```

```
acccatgaaa ttgaccccca aatacatcct gcggaangaa ttcaggaata tctgttccca      720
gcccctcctc cctcaggccc aggagtccag gcccccagcc cctcctccct caaaccaagg      780
gtacagatcc ccagcccctc ctccctcaga cccaggagtc cagaccccccc agccctctcnt    840 ccntcagacc caggagtcca gcccctcctc cntcagacgc aggagtccag acccccagc      900 ccntcntccg tcagacccag gggtgcaggc ccccaacccc tcntcntca gagtcagagg      960 tccaagcccc caacccctcg ttccccagac ccagaggtnc aggtcccagc ccctcctccc     1020
tcagacccag cggtccaatg ccacctagan tntccctgta cacagtgccc ccttgtggca     1080
ngttgaccca accttaccag ttggtttttc attttttgtc cctttcccct agatccagaa     1140
ataaagtnta agagaagcgc aaaaaaa                                          1167
```

<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Leu Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
    130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205
```

<210> SEQ ID NO 177
<211> LENGTH: 1119
<212> TYPE: DNA
<213> ORGANISM: Homo sapien

<400> SEQUENCE: 177

```
gcgcactcgc agccctggca ggcggcactg gtcatggaaa acgaattgtt ctgctcgggc       60
```

-continued

```
gtcctggtgc atccgcagtg ggtgctgtca gccgcacact gtttccagaa ctcctacacc    120
atcgggctgg gcctgcacag tcttgaggcc gaccaagagc cagggagcca gatggtggag    180
gccagcctct ccgtacggca cccagagtac aacagaccct gctcgctaa cgacctcatg     240 ctcatcaagt tggacgaatc cgtgtccgag tctgacacca tccggagcat cagcattgct    300
tcgcagtgcc ctaccgcggg gaactcttgc ctcgtttctg gctggggtct gctggcgaac    360
gatgctgtga ttgccatcca gtcccagact gtgggaggct gggagtgtga aagctttcc    420 caaccctggc agggttgtac catttcggca acttccagtg caaggacgtc ctgctgcatc    480
ctcactgggt gctcactact gctcactgca tcacccggaa cactgtgatc aactagccag    540
caccatagtt ctccgaagtc agactatcat gattactgtg ttgactgtgc tgtctattgt    600
actaaccatg ccgatgttta ggtgaaatta gcgtcacttg gcctcaacca tcttggtatc    660
cagttatcct cactgaattg agatttcctg cttcagtgtc agccattccc acataatttc    720
tgacctacag aggtgaggga tcatatagct cttcaaggat gctggtactc ccctcacaaa    780
ttcatttctc ctgttgtagt gaaaggtgcg ccctctggag cctcccaggg tgggtgtgca    840
ggtcacaatg atgaatgtat gatcgtgttc ccattaccca aagcctttaa atccctcatg    900
ctcagtacac cagggcaggt ctagcatttc ttcatttagt gtatgctgtc cattcatgca    960
accacctcag gactcctgga ttctctgcct agttgagctc ctgcatgctg cctccttggg    1020
gaggtgaggg agagggccca tggttcaatg ggatctgtgc agttgtaaca cattaggtgc    1080
ttaataaaca gaagctgtga tgttaaaaaa aaaaaaaaa                           1119
```

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Leu Thr Ala Ser
145                 150                 155                 160

Pro Gly Thr Leu
```

<210> SEQ ID NO 179
<211> LENGTH: 250
<212> TYPE: DNA
<213> ORGANISM: Homo sapien

<400> SEQUENCE: 179

| | | | | | |
|---|---|---|---|---|---|
| ctggagtgcc | ttggtgtttc | aagcccctgc | aggaagcaga | atgcaccttc | tgaggcacct | 60 |
| ccagctgccc | ccggccgggg | gatgcgaggc | tcggagcacc | cttgccggc | tgtgattgct | 120 |
| gccaggcact | gttcatctca | gcttttctgt | ccctttgctc | ccggcaagcg | cttctgctga | 180 |
| aagttcatat | ctggagcctg | atgtcttaac | gaataaaggt | cccatgctcc | acccgaaaaa | 240 |
| aaaaaaaaaa | | | | | | 250 |

<210> SEQ ID NO 180
<211> LENGTH: 202
<212> TYPE: DNA
<213> ORGANISM: Homo sapien

<400> SEQUENCE: 180

| | | | | | |
|---|---|---|---|---|---|
| actagtccag | tgtggtggaa | ttccattgtg | ttgggcccaa | cacaatggct | acctttaaca | 60 |
| tcacccagac | cccgcccctg | cccgtgcccc | acgctgctgc | taacgacagt | atgatgctta | 120 |
| ctctgctact | cggaaactat | ttttatgtaa | ttaatgtatg | ctttcttgtt | tataaatgcc | 180 |
| tgatttaaaa | aaaaaaaaaa | aa | | | | 202 |

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181

| | | | | | |
|---|---|---|---|---|---|
| tccytttgkt | naggttttkkg | agacamcccck | agacctwaan | ctgtgtcaca | gacttcyngg | 60 |
| aatgtttagg | cagtgctagt | aatttcytcg | taatgattct | gttattactt | tcctnattct | 120 |
| ttattcctct | ttcttctgaa | gattaatgaa | gttgaaaatt | gaggtggata | aatacaaaaa | 180 |
| ggtagtgtga | tagtataagt | atctaagtgc | agatgaaagt | gtgttatata | tatccattca | 240 |
| aaattatgca | agttagtaat | tactcagggt | taactaaatt | actttaatat | gctgttgaac | 300 |
| ctactctgtt | ccttggctag | aaaaaattat | aaacaggact | ttgttagttt | gggaagccaa | 360 |
| attgataata | ttctatgttc | taaaagttgg | gctatacata | aattattaag | aaatatggaw | 420 |
| ttttattccc | aggaatatgg | kgttcattt | atgaatatta | cscrggatag | awgtwtgagt | 480 |
| aaaaycagtt | ttggtwaata | ygtwaatatg | tcmtaaataa | acaakgcttt | gacttatttc | 540 |
| caaaaaaaaa | aaaaaaaa | | | | | 558 |

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182

| | |
|---|---:|
| acagggwttk grggatgcta agsccccrga rwtygtttga tccaaccctg gcttwttttc | 60 |
| agagggaaa atgggccta aagttacag mscatytagy tggtgcgmtg gcaccctgg | 120 |
| cstcacacag astcccgagt agctgggact acaggcacac agtcactgaa gcaggccctg | 180 |
| ttwgcaattc acgttgccac ctccaactta aacattcttc atatgtgatg tccttagtca | 240 |
| ctaaggttaa actttcccac ccagaaaagg caacttagat aaaatcttag agtactttca | 300 |
| tactmttcta agtcctcttc cagcctcact kkgagtcctm cytgggggtt gataggaant | 360 |
| ntctcttggc tttctcaata aartctctat ycatctcatg tttaatttgg tacgcatara | 420 |
| awtgstgara aaattaaaat gttctggtty mactttaaaa araaaaaaaa aaaaaaaaa | 479 |

<210> SEQ ID NO 183
<211> LENGTH: 384
<212> TYPE: DNA
<213> ORGANISM: Homo sapien

<400> SEQUENCE: 183

| | |
|---|---:|
| aggcgggagc agaagctaaa gccaaagccc aagaagagtg gcagtgccag cactggtgcc | 60 |
| agtaccagta ccaataacag tgccagtgcc agtgccagca ccagtggtgg cttcagtgct | 120 |
| ggtgccagcc tgaccgccac tctcacattt gggctcttcg ctggccttgg tggagctggt | 180 |
| gccagcacca gtggcagctc tggtgcctgt ggtttctcct acaagtgaga ttttagatat | 240 |
| tgttaatcct gccagtcttt ctcttcaagc cagggtgcat cctcagaaac ctactcaaca | 300 |
| cagcactcta ggcagccact atcaatcaat tgaagttgac actctgcatt aratctattt | 360 |
| gccatttcaa aaaaaaaaaa aaaa | 384 |

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

| | |
|---|---:|
| accgaattgg gaccgctggc ttataagcga tcatgtyynt ccrgtatkac ctcaacgagc | 60 |
| agggagatcg agtctatacg ctgaagaaat ttgacccgat gggacaacag acctgctcag | 120 |
| cccatcctgc tcggttctcc ccagatgaca aatactctsg acaccgaatc accatcaaga | 180 |
| aacgcttcaa ggtgctcatg acccagcaac cgcgccctgt cctctgaggg tcccttaaac | 240 |
| tgatgtcttt tctgccacct gttaccccct ggagactccg taaccaaact cttcggactg | 300 |
| tgagccctga tgccttttg ccagccatac tctttggcat ccagtctctc gtggcgattg | 360 |
| attatgcttg tgtgaggcaa tcatggtggc atcacccata aagggaacac atttgactt | 420 |
| tttttctcat atttttaaatt actacmagaw tattwmagaw waaatgawtt gaaaaactst | 480 |
| taaaaaaaaa aaaaaa | 496 |

<210> SEQ ID NO 185
<211> LENGTH: 384
<212> TYPE: DNA
<213> ORGANISM: Homo sapien

<400> SEQUENCE: 185

| | |
|---|---:|
| gctggtagcc tatggcgkgg cccacggagg ggctcctgag gccacggrac agtgacttcc | 60 |
| caagtatcyt gcgcsgcgtc ttctaccgtc cctacctgca gatcttcggg cagattcccc | 120 |

| | |
|---|---|
| aggaggacat ggacgtggcc ctcatggagc acagcaactg ytcgtcggag cccggcttct | 180 |
| gggcacaccc tcctggggcc caggcgggca cctgcgtctc ccagtatgcc aactggctgg | 240 |
| tggtgctgct cctcgtcatc ttcctgctcg tggccaacat cctgctggtc aacttgctca | 300 |
| ttgccatgtt cagttacaca ttcggcaaag tacagggcaa cagcgatctc tactgggaag | 360 |
| gcgcagcgtt accgcctcat ccgg | 384 |

<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

| | |
|---|---|
| gagttagctc ctccacaacc ttgatgaggt cgtctgcagt ggcctctcgc ttcataccgc | 60 |
| tnccatcgtc atactgtagg tttgccacca cytcctggca tcttggggcg gcntaatatt | 120 |
| ccaggaaact ctcaatcaag tcaccgtcga tgaaacctgt gggctggttc tgtcttccgc | 180 |
| tcggtgtgaa aggatctccc agaaggagtg ctcgatcttc cccacacttt tgatgacttt | 240 |
| attgagtcga ttctgcatgt ccagcaggag gttgtaccag ctctctgaca gtgaggtcac | 300 |
| cagccctatc atgccgttga mcgtgccgaa garcaccgag ccttgtgtgg gggkkgaagt | 360 |
| ctcacccaga ttctgcatta ccagagagcc gtggcaaaag acattgacaa actcgcccag | 420 |
| gtggaaaaag amcamctcct ggargtgctn gccgctcctc gtcmgttggt ggcagcgctw | 480 |
| tccttttgac acacaaacaa gttaaaggca ttttcagccc ccagaaantt gtcatcatcc | 540 |
| aagatntcgc acagcactna tccagttggg attaaat | 577 |

<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

| | |
|---|---|
| aacatcttcc tgtataatgc tgtgtaatat cgatccgatn ttgtctgstg agaatycatw | 60 |
| actkggaaaa gmaacattaa agcctggaca ctggtattaa aattcacaat atgcaacact | 120 |
| ttaaacagtg tgtcaatctg ctcccyynac tttgtcatca ccagtctggg aakaagggta | 180 |
| tgccctattc acacctgtta aaagggcgct aagcattttt gattcaacat ctttttttttt | 240 |
| gacacaagtc cgaaaaaagc aaaagtaaac agttatyaat ttgttagcca attcactttc | 300 |
| ttcatgggac agagccatyt gatttaaaaa gcaaattgca taatattgag cttygggagc | 360 |
| tgatatttga gcggaagagt agcctttcta cttcaccaga cacaactccc tttcatattg | 420 |
| ggatgttnac naaagtwatg tctctwacag atgggatgct tttgtggcaa ttctgttctg | 480 |
| aggatctccc agtttattta ccacttgcac aagaaggcgt tttcttcctc aggc | 534 |

<210> SEQ ID NO 188
<211> LENGTH: 761
<212> TYPE: DNA
<213> ORGANISM: Homo sapien
<220> FEATURE:

```
<221> NAME/KEY: misc_feature
<222> LOCATION: (1)...(761)
<223> OTHER INFORMATION: n = A,T,C or G

<400> SEQUENCE: 188
agaaaccagt atctctnaaa acaacctctc ataccttgtg gacctaattt tgtgtgcgtg    60
tgtgtgtgcg cgcatattat atagacaggc acatctttt tactttgta aaagcttatg   120 cctctttggt atctatatct gtgaaagttt taatgatctg ccataatgtc ttggggacct   180
ttgtcttctg tgtaaatggt actagagaaa acacctatnt tatgagtcaa tctagttngt   240
tttattcgac atgaaggaaa tttccagatn acaacactna caaactctcc ctkgackarg   300
ggggacaaag aaaagcaaaa ctgamcataa raaacaatwa cctggtgaga arttgcataa   360
acagaaatwr ggtagtatat tgaarnacag catcattaaa rmgttwtktt wttctcccctt   420 gcaaaaaaca tgtacngact tcccgttgag taatgccaag ttgttttttt tatnataaaa   480
cttgcccttc attacatgtt tnaaagtggt gtggtgggcc aaaatattga aatgatggaa   540
ctgactgata aagctgtaca aataagcagt gtgcctaaca agcaacacag taatgttgac   600
atgcttaatt cacaaatgct aatttcatta taaatgtttg ctaaaataca ctttgaacta   660 ttttttctgtn ttcccagagc tgagatntta gattttatgt agtataagt gaaaaantac   720 gaaataata acattgaaga aaanananaa aaanaaaaaa a                        761

<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189
tttttttttt tttgccgatn ctactatttt attgcaggan gtggggtgt atgcaccgca    60 caccggggct atnagaagca agaaggaagg agggagggca cagccccttg ctgagcaaca   120
aagccgcctg ctgccttctc tgtctgtctc ctggtgcagg cacatgggga gaccttcccc   180
aaggcagggg ccaccagtcc agggggtggga atacaggggg tgggangtgt gcataagaag   240
tgataggcac aggccacccg gtacagaccc ctcggctcct gacaggtnga tttcgaccag   300
gtcattgtgc cctgcccagg cacagcgtan atctggaaaa dacagaatgc tttccttttc   360
aaatttggct ngtcatngaa nggcantttt tccaanttng gctnggtctt ggtacncttg   420
gttcggccca gctccncgtc caaaaantat tcacccnnct ccnaattgct tgcnggnccc   480
cc                                                                 482

<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190
tttttttttt ttttaaaaca gttttcaca acaaaattta ttagaagaat agtggttttg    60
aaaactctcg catccagtga gaactaccat acaccacatt acagctngga atgtnctcca   120
aatgtctggt caaatgatac aatggaacca ttcaatctta cacatgcacg aaagaacaag   180
```

```
cgcttttgac atacaatgca caaaaaaaaa agggggggggg gaccacatgg attaaaattt        240
taagtactca tcacatacat taagacacag ttctagtcca gtcnaaaatc agaactgcnt        300
tgaaaaattt catgtatgca atccaaccaa agaacttnat tggtgatcat gantnctcta        360
ctacatcnac cttgatcatt gccaggaacn aaaagttnaa ancacncngt acaaaaanaa        420
tctgtaattn anttcaacct ccgtacngaa aaatnttnnt tatacactcc c                 471

<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191
gagggattga aggtctgttc tastgtcggm ctgttcagcc accaactcta acaagttgct        60
gtcttccact cactgtctgt aagcttttta acccagacwg tatcttcata aatagaacaa       120
attcttcacc agtcacatct tctaggacct ttttggattc agttagtata agctcttcca       180
cttcctttgt taagacttca tctggtaaag tcttaagttt tgtagaaagg aattyaattg       240
ctcgttctct aacaatgtcc tctccttgaa gtatttggct gaacaaccca cctaaagtcc       300
cttttgtcat ccattttaaa tatacttaat agggcattgk tncactaggt taaattctgc       360
aagagtcatc tgtctgcaaa agttgcgtta gtatatctgc ca                          402

<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192
gagctcggat ccaataatct ttgtctgagg gcagcacaca tatncagtgc catggnaact        60
ggtctacccc acatgggagc agcatgccgt agntatataa ggtcattccc tgagtcagac       120
atgcytyttt gaytaccgtg tgccaagtgc tggtgattct yaacacacyt ccatcccgyt       180
cttttgtgga aaaactggca cttktctgga actagcarga catcacttac aaattcaccc       240
acgagacact tgaaaggtgt aacaaagcga ytcttgcatt gcttttttgtc cctccggcac       300 cagttgtcaa tactaacccg ctggtttgcc tccatcacat ttgtgatctg tagctctgga       360
tacatctcct gacagtactg aagaacttct tcttttgttt caaaagcarc tcttggtgcc       420
tgttggatca ggttcccatt tcccagtcyg aatgttcaca tggcatattt wacttcccac       480
aaaacattgc gatttgaggc tcagcaacag caaatcctgt tccggcattg gctgcaagag       540
cctcgatgta gccggccagc gccaaggcag gcgccgtgag cccaccagc agcagaagca       600 g                                                                       601

<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
```

<223> OTHER INFORMATION: n = A,T,C or G

<400> SEQUENCE: 193

```
atacagccca natcccacca cgaagatgcg cttgttgact gagaacctga tgcggtcact      60
ggtcccgctg tagccccagc gactctccac ctgctggaag cggttgatgc tgcactcytt    120
cccaacgcag gcagmagcgg gsccggtcaa tgaactccay tcgtggcttg gggtkgacgg    180
tkaagtgcag gaagaggctg accacctcgc ggtccaccag gatgcccgac tgtgcgggac    240
ctgcagcgaa actcctcgat ggtcatgagc gggaagcgaa tgaggcccag ggccttgccc    300
agaaccttcc gcctgttctc tggcgtcacc tgcagctgct gccgctgaca ctcggcctcg    360
gaccagcgga caaacggcrt tgaacagccg cacctcacgg atgcccagtg tgtcgcgctc    420
caggammgsc accagcgtgt ccaggtcaat gtcggtgaag ccctccgcgg gtratggcgt    480
ctgcagtgtt tttgtcgatg ttctccaggc acaggctggc cagctgcggt tcatcgaaga    540
gtcgcgcctg cgtgagcagc atgaaggcgt tgtcggctcg cagttcttct tcaggaactc    600
cacgcaat                                                             608
```

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194

```
gaacggctgg accttgcctc gcattgtgct tgctggcagg gaatacctttg gcaagcagyt     60
ccagtccgag cagccccaga ccgctgccgc ccgaagctaa gcctgcctct ggccttcccc    120
tccgcctcaa tgcagaacca gtagtgggag cactgtgttt agagttaaga gtgaacactg    180
tttgatttta cttgggaatt tcctctgtta tatagctttt cccaatgcta atttccaaac    240
aacaacaaca aaataacatg tttgcctgtt aagttgtata aaagtaggtg attctgtatt    300
taaagaaaat attactgtta catatactgc ttgcaatttc tgtatttatt gktnctstgg    360
aaataaatat agttattaaa ggttgtcant cc                                   392
```

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195

```
ccsttkgagg ggtkaggkyc cagttyccga gtggaagaaa caggccagga gaagtgcgtg     60
ccgagctgag gcagatgttc ccacagtgac ccccagagcc stgggstata gtytctgacc    120
cctcncaagg aaagaccacs ttctggggac atgggctgga gggcaggacc tagaggcacc    180
aaggaaggc cccattccgg ggstgttccc cgaggaggaa gggaagggc tctgtgtgcc    240
ccccasgagg aagaggccct gagtcctggg atcagacacc ccttcacgtg tatccccaca    300
caaatgcaag ctcaccaagg tccctctca gtcccttcc stacccctg amcggccact    360
gscscacacc cacccagagc acgccacccg ccatggggar tgtgctcaag gartcgcngg    420
gcarcgtgga catctngtcc cagaaggggg cagaatctcc aatagangga ctgarcmstt    480
```

```
gctnanaaaa aaaaanaaaa aa                                                  502
```

<210> SEQ ID NO 196
<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196

```
ggttacttgg tttcattgcc accacttagt ggatgtcatt tagaaccatt ttgtctgctc          60
cctctggaag ccttgcgcag agcggactt  gtaattgttg gagaataact gctgaatttt         120
wagctgttk  gagttgatts gcaccactgc acccacaact tcaatatgaa aacyawttga         180
actwatttat tatcttgtga aaagtataac aatgaaaatt ttgttcatac tgtattkatc         240
aagtatgatg aaaagcaawa gatatatatt cttttattat gttaaattat gattgccatt        300
attaatcggc aaaatgtgga gtgtatgttc ttttcacagt aatatatgcc ttttgtaact        360
tcacttggtt attttattgt aaatgartta caaaattctt aatttaagar aatggtatgt        420
watatttatt tcattaattt ctttcctkgt ttacgtwaat tttgaaaaga wtgcatgatt        480
tcttgacaga aatcgatctt gatgctgtgg aagtagttg  acccacatcc ctatgagttt        540
ttcttagaat gtataaaggt tgtagcccat cnaacttcaa agaaaaaaat gaccacatac        600
tttgcaatca ggctgaaatg tggcatgctn ttctaattcc aactttataa actagcaaan        660
aagtg                                                                    665
```

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197

```
ttttnttttt tttttttgc  aggaaggatt ccatttattg tggatgcatt ttcacaatat         60
atgtttattg gagcgatcca ttatcagtga aaagtatcaa gtgtttataa nattttagg         120
aaggcagatt cacagaacat gctngtcngc ttgcagtttt acctcgtana gatnacagag        180
aattatagtc naaccagtaa acnaggaatt tacttttcaa aagattaaat ccaaactgaa        240
caaaattcta ccctgaaact tactccatcc aaatattgga ataanagtca gcagtgatac        300
attctcttct gaactttaga ttttctagaa aaatatgtaa tagtgatcag gaagagctct        360
tgttcaaaag tacaacnaag caatgttccc ttaccatagg ccttaattca aactttgatc        420
catttcactc ccatcacggg agtcaatgct acctgggaca cttgtatttt gttcatnctg        480
ancntggctt aa                                                            492
```

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

```
<400> SEQUENCE: 198
tttnttttgn atttcantct gtannaanta ttttcattat gtttattana aaaatatnaa      60
tgtntccacn acaaatcatn ttacntnagt aagaggccan ctacattgta caacatacac     120
tgagtatatt ttgaaaagga caagtttaaa gtanacncat attgccganc atancacatt     180
tatacatggc ttgattgata tttagcacag canaaactga gtgagttacc agaaanaaat    240
natatatgtc aatcngattt aagatacaaa acagatccta tggtacatan catcntgtag    300
gagttgtggg tttatgttta ctgaaagtca atgcagttcc tgtacaaaga gatggccgta    360
agcattctag tacctctact ccatggttaa gaatcgtaca cttatgttta catatgtnca    420
gggtaagaat tgtgttaagt naanttatgg agaggtccan gagaaaaatt tgatncaa     478

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199
agtgacttgt cctccaacaa aaccccttga tcaagtttgt ggcactgaca atcagaccta     60
tgctagttcc tgtcatctat tcgctactaa atgcagactg gaggggacca aaaaggggca    120
tcaactccag ctggattatt ttggagcctg caaatctatt cctacttgta cggactttga    180
agtgattcag tttcctctac ggatgagaga ctggctcaag aatatcctca tgcagcttta    240
tgaagccnac tctgaacacg ctggttatct nagatgagaa ncagagaaat aaagtcnaga    300
aaatttacct ggangaaaag aggctttngg ctggggacca tcccattgaa ccttctctta    360
anggacttta agaanaaact accacatgtn tgtngtatcc tggtgccngg ccgtttantg    420
aacntngacn ncacccttnt ggaatanant cttgacngcn tcctgaactt gctcctctgc    480
ga                                                                  482

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200
cggccgcaag tgcaactcca gctggggccg tgcggacgaa gattctgcca gcagttggtc     60
cgactgcgac gacggcggcg gcgacagtcg caggtgcagc gcgggcgcct ggggtcttgc    120
aaggctgagc tgacgccgca gaggtcgtgt cacgtcccac gaccttgacg ccgtcgggga    180
cagccggaac agagcccggt gaangcggga ggcctcgggg agcccctcgg gaagggcggc    240
ccgagagata cgcaggtgca ggtggccgcc                                    270

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G
```

<400> SEQUENCE: 201

| | | | | | |
|---|---|---|---|---|---|
| tttttttttt | ttttggaatc | tactgcgagc | acagcaggtc | agcaacaagt | ttattttgca | 60 |
| gctagcaagg | taacagggta | gggcatggtt | acatgttcag | gtcaacttcc | tttgtcgtgg | 120 |
| ttgattggtt | tgtctttatg | ggggcggggt | ggggtagggg | aaancgaagc | anaantaaca | 180 |
| tggagtgggt | gcaccctccc | tgtagaacct | ggttacnaaa | gcttgggca | gttcacctgg | 240 |
| tctgtgaccg | tcattttctt | gacatcaatg | ttattagaag | tcaggatatc | ttttagagag | 300 |
| tccactgtnt | ctggagggag | attagggttt | cttgccaana | tccaancaaa | atccacntga | 360 |
| aaaagttgga | tgatncangt | acngaatacc | ganggcatan | ttctcatant | cggtggcca | 419 |

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

| | | | | | |
|---|---|---|---|---|---|
| tttnttttt | tttttttttt | tttttttttt | tttttttttt | tttttttttt | tttttttttt | 60 |
| tggcacttaa | tccattttta | tttcaaaatg | tctacaaant | ttnaatncnc | cattatacng | 120 |
| gtnattttnc | aaaatctaaa | nnttattcaa | atntnagcca | aantccttac | ncaaatnnaa | 180 |
| tacncncaaa | aatcaaaaat | atacntntct | ttcagcaaac | ttngttacat | aaattaaaaa | 240 |
| aatatatacg | gctggtgttt | tcaaagtaca | attatcttaa | cactgcaaac | atntttnnaa | 300 |
| ggaactaaaa | taaaaaaaaa | cactnccgca | aaggttaaag | ggaacaacaa | attcntttta | 360 |
| caacancnnc | nattataaaa | atcatatctc | aaatcttagg | ggaatatata | cttcacacng | 420 |
| ggatcttaac | ttttactnca | ctttgtttat | tttttttanaa | ccattgtntt | gggcccaaca | 480 |
| caatggnaat | nccnccncnc | tggactagt | | | | 509 |

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

| | | | | | |
|---|---|---|---|---|---|
| tttttttttt | ttttttttga | ccccctctt | ataaaaaca | agttaccatt | ttatttact | 60 |
| tacacatatt | tatttataa | ttggtattag | atattcaaaa | ggcagctttt | aaaatcaaac | 120 |
| taaatggaaa | ctgccttaga | tacataattc | ttaggaatta | gcttaaaatc | tgcctaaagt | 180 |
| gaaaatcttc | tctagctctt | ttgactgtaa | attttttgact | cttgtaaaac | atccaaattc | 240 |
| atttttcttg | tctttaaaat | tatctaatct | ttccatttt | tccctattcc | aagtcaattt | 300 |
| gcttctctag | cctcatttcc | tagctcttat | ctactattag | taagtggctt | ttttcctaaa | 360 |
| agggaaaaca | ggaagagana | atggcacaca | aaacaaacat | tttatattca | tatttctacc | 420 |
| tacgttaata | aaatagcatt | ttgtgaagcc | agctcaaaag | aaggcttaga | tccttttatg | 480 |
| tccatttag | tcactaaacg | atatcnaaag | tgccagaatg | caaaggttt | gtgaacattt | 540 |
| attcaaaagc | taatataaga | tatttcacat | actcatcttt | ctg | | 583 |

<210> SEQ ID NO 204
<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204

| | | | | | |
|---|---|---|---|---|---|
| ttttttttnt | tttttttttt | tttttncto | ttcttttttt | ttganaatga | ggatcgagtt | 60 |
| tttcactctc | tagatagggc | atgaagaaaa | ctcatctttc | cagctttaaa | ataacaatca | 120 |
| aatctcttat | gctatatcat | attttaagtt | aaactaatga | gtcactggct | tatcttctcc | 180 |
| tgaaggaaat | ctgttcattc | ttctcattca | tatagttata | tcaagtacta | ccttgcatat | 240 |
| tgagaggttt | tcttctcta | tttacacata | tatttccatg | tgaatttgta | tcaaaccttt | 300 |
| attttcatgc | aaactagaaa | ataatgtntt | cttttgcata | agagaagaga | acaatatnag | 360 |
| cattacaaaa | ctgctcaaat | tgtttgttaa | gnttatccat | tataattagt | tnggcaggag | 420 |
| ctaatacaaa | tcacatttac | ngacnagcaa | taataaaact | gaagtaccag | ttaaatatcc | 480 |
| aaaataatta | aaggaacatt | tttagcctgg | gtataattag | ctaattcact | ttacaagcat | 540 |
| ttattnagaa | tgaattcaca | tgttattatt | ccntagccca | acacaatgg | | 589 |

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205

| | | | | | |
|---|---|---|---|---|---|
| tttttntttt | tttttttcagt | aataatcaga | acaatattta | ttttatatt | taaaattcat | 60 |
| agaaaagtgc | cttacattta | ataaagttt | gtttctcaaa | gtgatcagag | gaattagata | 120 |
| tngtcttgaa | caccaatatt | aatttgagga | aaatacacca | aaatacatta | agtaaattat | 180 |
| ttaagatcat | agagcttgta | agtgaaaaga | taaaatttga | cctcagaaac | tctgagcatt | 240 |
| aaaaatccac | tattagcaaa | taaattacta | tggacttctt | gctttaattt | tgtgatgaat | 300 |
| atggggtgtc | actggtaaac | caacacattc | tgaaggatac | attacttagt | gatagattct | 360 |
| tatgtactt | gctanatnac | gtggatatga | gttgacaagt | ttctctttct | tcaatctttt | 420 |
| aaggggcnga | ngaaatgagg | aagaaaagaa | aaggattacg | catactgttc | tttctatngg | 480 |
| aaggattaga | tatgtttcct | ttgccaatat | taaaaaaata | ataatgttta | ctactagtga | 540 |
| aaccc | | | | | | 545 |

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206

| | | | | | |
|---|---|---|---|---|---|
| tttttttttt | tttttagtc | aagtttctna | ttttattat | aattaaagtc | ttggtcattt | 60 |
| catttattag | ctctgcaact | tacatattta | aattaaagaa | acgttnttag | acaactgtna | 120 |

```
caatttataa atgtaaggtg ccattattga gtanatatat tcctccaaga gtggatgtgt    180
cccttctccc accaactaat gaancagcaa cattagttta atttattag tagatnatac     240 actgctgcaa acgctaattc tcttctccat ccccatgtng atattgtgta tatgtgtgag    300
ttggtnagaa tgcatcanca atctnacaat caacagcaag atgaagctag gcntgggctt    360
tcggtgaaaa tagactgtgt ctgtctgaat caaatgatct gacctatcct cggtggcaag    420
aactcttcga accgcttcct caaaggcngc tgccacattt gtggcntctn ttgcacttgt    480
ttcaaaa                                                              487
```

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207

```
tgaattggct aaaagactgc attttttanaa ctagcaactc ttatttcttt cctttaaaaa   60
tacatagcat taaatcccaa atcctatttta aagacctgac agcttgagaa ggtcactact   120
gcatttatag gaccttctgg tggttctgct gttacntttg aantctgaca atccttgana   180
atctttgcat gcagaggagg taaaaggtat tggattttca cagaggaana acacagcgca   240
gaaatgaagg ggccaggctt actgagcttg tccactggag ggctcatggg tgggacatgg   300
aaaagaaggc agcctaggcc ctggggagcc ca                                  332
```

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208

```
agggcgtggt gcggagggcg ttactgtttt gtctcagtaa caataaatac aaaaagactg    60
gttgtgttcc ggccccatcc aaccacgaag ttgatttctc ttgtgtgcag agtgactgat    120
tttaaaggac atggagcttg tcacaatgtc acaatgtcac agtgtgaagg gcacactcac    180
tcccgcgtga ttcacattta gcaaccaaca atagctcatg agtccatact tgtaaatact    240
tttggcagaa tacttnttga aacttgcaga tgataactaa gatccaagat atttcccaaa    300
gtaaatagaa gtgggtcata atattaatta cctgttcaca tcagcttcca tttacaagtc    360
atgagcccag acactgacat caaactaagc ccacttagac tcctcaccac cagtctgtcc    420
tgtcatcaga caggaggctg tcaccttgac caaattctca ccagtcaatc atctatccaa    480
aaaccattac ctgatccact tccggtaatg caccaccttg tga                      524
```

<210> SEQ ID NO 209
<211> LENGTH: 159
<212> TYPE: DNA
<213> ORGANISM: Homo sapien

<400> SEQUENCE: 209

```
gggtgaggaa atccagagtt gccatggaga aaattccagt gtcagcattc ttgctccttg     60
```

| | |
|---|---|
| tggccctctc ctacactctg gccagagata ccacagtcaa acctggagcc aaaaaggaca | 120 |
| caaaggactc tcgacccaaa ctgccccaga ccctctcca | 159 |

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210

| | |
|---|---|
| actccctggc agacaaaggc agaggagaga gctctgttag ttctgtgttg ttgaactgcc | 60 |
| actgaatttc tttccacttg gactattaca tgccanttga gggactaatg gaaaaacgta | 120 |
| tggggagatt ttanccaatt tangtntgta aatggggaga ctggggcagg cgggagagat | 180 |
| ttgcagggtg naaatgggan ggctggtttg ttanatgaac agggacatag gaggtaggca | 240 |
| ccaggatgct aaatca | 256 |

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211

| | |
|---|---|
| acattgtttt tttgagataa agcattgaga gagctctcct taacgtgaca caatggaagg | 60 |
| actggaacac atacccacat ctttgttctg agggataatt ttctgataaa gtcttgctgt | 120 |
| atattcaagc acatatgtta tatattattc agttccatgt ttatagccta gttaaggaga | 180 |
| ggggagatac attcngaaag aggactgaaa gaaatactca agtnggaaaa cagaaaaaga | 240 |
| aaaaaggag caaatgagaa gcct | 264 |

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212

| | |
|---|---|
| acccaaaaat ccaatgctga atatttggct tcattattcc canattcttt gattgtcaaa | 60 |
| ggatttaatg ttgtctcagc ttgggcactt cagttaggac ctaaggatgc cagccggcag | 120 |
| gtttatatat gcagcaacaa tattcaagcg cgacaacagg ttattgaact tgcccgccag | 180 |
| ttnaatttca ttcccattga cttgggatcc ttatcatcag ccagagagat tgaaaattta | 240 |
| ccccctacnac tctttactct ctgganaggg ccagtggtgg tagctataag cttggccaca | 300 |
| ttttttttc ctttattcct ttgtcaga | 328 |

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

```
acttatgagc agagcgacat atccnagtgt agactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataanc catgttaana aacaaatatc tctctnacct     240
tctcatcggt                                                            250
```

<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

```
acccagaatc caatgctgaa tatttggctt cattattccc agattctttg attgtcaaag      60
gatttaatgt tgtctcagct tgggcacttc agttaggacc taaggatgcc agccggcagg     120
tttatatatg cagcaacaat attcaagcgc gacaacaggt tattgaactt gcccgccagt     180
tgaatttcat tcccattgac ttgggatcct tatcatcagc canagagatt gaaaatttac     240
ccctacgact ctttactctc tggagagggc cagtggtggt agctataagc ttggccacat     300
ttttttttcc tttattcctt tgtcagagat gcgattcatc catatgctan aaaccaacag     360
agtgactttt acaaaattcc tataganatt gtgaataaaa ccttacctat agttgccatt     420
actttgctct ccctaatata cctc                                            444
```

<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

```
acttatgagc agagcgacat atccaagtgt anactgaata aaactgaatt ctctccagtt      60
taaagcattg ctcactgaag ggatagaagt gactgccagg agggaaagta agccaaggct     120
cattatgcca aagganatat acatttcaat tctccaaact tcttcctcat tccaagagtt     180
ttcaatattt gcatgaacct gctgataagc catgttgaga aacaaatatc tctctgacct     240
tctcatcggt aagcagaggc tgtaggcaac atggaccata gcgaanaaaa aacttagtaa     300
tccaagctgt tttctacact gtaaccaggt ttccaaccaa ggtggaaatc tcctatactt     360
ggtgcc                                                                366
```

<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

```
<400> SEQUENCE: 216
ctgtataaac agaactccac tgcangaggg agggccgggc caggagaatc tccgcttgtc    60
caagacaggg gcctaaggag ggtctccaca ctgctnntaa gggctnttnc atttttttat   120
taataaaaag tnnaaaaggc ctcttctcaa cttttttccc ttnggctgga aaatttaaaa   180
atcaaaaatt tcctnaagtt ntcaagctat catatatact ntatcctgaa aaagcaacat   240
aattcttcct tccctccttt                                               260

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217
acctacgtgg gtaagtttan aaatgttata atttcaggaa naggaacgca tataattgta    60
tcttgcctat aattttctat tttaataagg aaatagcaaa ttggggtggg gggaatgtag   120
ggcattctac agtttgagca aaatgcaatt aaatgtggaa ggacagcact gaaaaatttt   180
atgaataatc tgtatgatta tatgtctcta gagtagattt ataattagcc acttacccta   240
atatccttca tgcttgtaaa gt                                            262

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218
accaaggtgg tgcattaccg gaantggatc aangacacca tcgtggccaa ccctgagca     60 ccctatcaa ctccttttg tagtaaactt ggaaccttgg aaatgaccag gccaagactc    120
aggcctcccc agttctactg acctttgtcc ttangtntna ngtccagggt tgctaggaaa   180
anaaatcagc agacacaggt gtaaa                                         205

<210> SEQ ID NO 219
<211> LENGTH: 114
<212> TYPE: DNA
<213> ORGANISM: Homo sapien

<400> SEQUENCE: 219
tactgttttg tctcagtaac aataaataca aaagactgg ttgtgttccg gccccatcca     60
accacgaagt tgatttctct tgtgtgcaga gtgactgatt ttaaaggaca tgga         114

<210> SEQ ID NO 220
<211> LENGTH: 93
<212> TYPE: DNA
<213> ORGANISM: Homo sapien

<400> SEQUENCE: 220
actagccagc acaaaaggca gggtagcctg aattgctttc tgctctttac atttctttta    60
aaataagcat ttagtgctca gtccctactg agt                                 93
```

```
<210> SEQ ID NO 221
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 221
actangtgca ggtgcgcaca aatatttgtc gatattccct tcatcttgga ttccatgagg      60
tcttttgccc agcctgtggc tctactgtag taagtttctg ctgatgagga gccagnatgc     120
cccccactac cttccctgac gctccccana atcacccaa cctctgt                    167

<210> SEQ ID NO 222
<211> LENGTH: 351
<212> TYPE: DNA
<213> ORGANISM: Homo sapien

<400> SEQUENCE: 222
agggcgtggt gcggagggcg gtactgacct cattagtagg aggatgcatt ctggcacccc      60
gttcttcacc tgtcccccaa tccttaaaag gccatactgc ataaagtcaa caacagataa     120
atgtttgctg aattaaagga tggatgaaaa aaattaataa tgaattttg cataatccaa      180 ttttctcttt tatatttcta gaagaagttt ctttgagcct attagatccc gggaatcttt     240
taggtgagca tgattagaga gcttgtaggt tgcttttaca tatatctggc atatttgagt     300
ctcgtatcaa aacaatagat tggtaaaggt ggtattattg tattgataag t              351

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223
aaaacaaaca aacaaaaaaa acaattcttc attcagaaaa attatcttag ggactgatat      60
tggtaattat ggtcaatta atwrtrttkt ggggcatttc cttacattgt cttgacaaga     120
ttaaaatgtc tgtgccaaaa ttttgtattt tatttggaga cttcttatca aaagtaatgc     180
tgccaaagga agtctaagga attagtagtg ttcccmtcac ttgtttggag tgtgctattc     240
taaaagattt tgatttcctg gaatgacaat tatattttaa ctttggtggg ggaaanagtt     300
ataggaccac agtcttcact tctgatactt gtaaattaat cttttattgc acttgttttg     360
accattaagc tatatgttta aaa                                            383

<210> SEQ ID NO 224
<211> LENGTH: 320
<212> TYPE: DNA
<213> ORGANISM: Homo sapien

<400> SEQUENCE: 224
cccctgaagg cttcttgtta gaaatagta cagttacaac caataggaac aacaaaaga       60 aaagtttgt gacattgtag tagggagtgt gtacccctta ctccccatca aaaaaaaat      120 ggatacatgg ttaaaggata raagggcaat attttatcat atgttctaaa agagaaggaa    180
gagaaaatac tactttctcr aaatggaagc ccttaaaggt gctttgatac tgaaggacac    240
```

| | |
|---|---|
| aaatgtggcc gtccatcctc ctttaragtt gcatgacttg dacacggtaa ctgttgcagt | 300 |
| tttaractcm gcattgtgac | 320 |

<210> SEQ ID NO 225
<211> LENGTH: 1214
<212> TYPE: DNA
<213> ORGANISM: Homo sapien

<400> SEQUENCE: 225

| | |
|---|---|
| gaggactgca gcccgcactc gcagccctgg caggcggcac tggtcatgga aaacgaattg | 60 |
| ttctgctcgg gcgtcctggt gcatccgcag tgggtgctgt cagccgcaca ctgtttccag | 120 |
| aactcctaca ccatcgggct gggcctgcac agtcttgagg ccgaccaaga gccagggagc | 180 |
| cagatggtgg aggccagcct ctccgtacgg cacccagagt acaacagacc cttgctcgct | 240 |
| aacgacctca tgctcatcaa gttggacgaa tccgtgtccg agtctgacac catccggagc | 300 |
| atcagcattg cttcgcagtg ccctaccgcg gggaactctt gcctcgtttc tggctggggt | 360 |
| ctgctggcga acggcagaat gcctaccgtg ctgcagtgcg tgaacgtgtc ggtggtgtct | 420 |
| gaggaggtct gcagtaagct ctatgacccg ctgtaccacc ccagcatgtt ctgcgccggc | 480 |
| ggagggcaag accagaagga ctcctgcaac ggtgactctg gggggcccct gatctgcaac | 540 |
| gggtacttgc agggccttgt gtctttcgga aaagcccgt gtggccaagt tggcgtgcca | 600 |
| ggtgtctaca ccaacctctg caattcact gagtggatag agaaaaccgt ccaggccagt | 660 |
| taactctggg gactgggaac ccatgaaatt gaccccccaaa tacatcctgc ggaaggaatt | 720 |
| caggaatatc tgttcccagc ccctcctccc tcaggcccag gagtccaggc ccccagcccc | 780 |
| tcctccctca aaccaagggt acagatcccc agccctcct ccctcagacc caggagtcca | 840 |
| gaccccccag cccctcctcc ctcagaccca ggagtccagc ccctcctccc tcagacccag | 900 |
| gagtccagac cccccagccc ctcctccctc agacccaggg gtccaggccc caacccctc | 960 |
| ctccctcaga ctcagaggtc caagccccca ccctccttc cccagaccc agaggtccag | 1020 |
| gtcccagccc ctcctccctc agacccagcg gtccaatgcc acctagactc tccctgtaca | 1080 |
| cagtgccccc ttgtggcacg ttgacccaac cttaccagtt ggttttttcat tttttgtccc | 1140 |
| tttcccctag atccagaaat aaagtctaag agaagcgcaa aaaaaaaaaa aaaaaaaaaa | 1200 |
| aaaaaaaaaa aaaa | 1214 |

<210> SEQ ID NO 226
<211> LENGTH: 119
<212> TYPE: DNA
<213> ORGANISM: Homo sapien

<400> SEQUENCE: 226

| | |
|---|---|
| acccagtatg tgcagggaga cggaaccca tgtgacagcc cactccacca gggttcccaa | 60 |
| agaacctggc ccagtcataa tcattcatcc tgacagtggc aataatcacg ataaccagt | 119 |

<210> SEQ ID NO 227
<211> LENGTH: 818
<212> TYPE: DNA
<213> ORGANISM: Homo sapien

<400> SEQUENCE: 227

| | |
|---|---|
| acaattcata gggacgacca atgaggacag ggaatgaacc cggctctccc ccagccctga | 60 |
| ttttttgctac atatggggtc ccttttcatt ctttgcaaaa acactgggtt ttctgagaac | 120 |
| acggacggtt cttagcacaa tttgtgaaat ctgtgtaraa ccgggctttg caggggagat | 180 |

| | |
|---|---|
| aattttcctc ctctggagga aaggtggtga ttgacaggca gggagacagt gacaaggcta | 240 |
| gagaaagcca cgctcggcct tctctgaacc aggatggaac ggcagacccc tgaaaacgaa | 300 |
| gcttgtcccc ttccaatcag ccacttctga aacccccat ctaacttcct actggaaaag | 360 |
| agggcctcct caggagcagt ccaagagttt caaagataa cgtgacaact accatctaga | 420 |
| ggaaagggtg caccctcagc agagaagccg agagcttaac tctggtcgtt ccagagaca | 480 |
| acctgctggc tgtcttggga tgcgcccagc ctttgagagg ccactacccc atgaacttct | 540 |
| gccatccact ggacatgaag ctgaggacac tgggcttcaa cactgagttg tcatgagagg | 600 |
| gacaggctct gccctcaagc cggctgaggg cagcaaccac tctcctcccc tttctcacgc | 660 |
| aaagccattc ccacaaatcc agaccatacc atgaagcaac gagacccaaa cagtttggct | 720 |
| caagaggata tgaggactgt ctcagcctgg ctttgggctg acaccatgca cacacacaag | 780 |
| gtccacttct aggttttcag cctagatggg agtcgtgt | 818 |

<210> SEQ ID NO 228
<211> LENGTH: 744
<212> TYPE: DNA
<213> ORGANISM: Homo sapien

<400> SEQUENCE: 228

| | |
|---|---|
| actggagaca ctgttgaact tgatcaagac ccagaccacc ccaggtctcc ttcgtgggat | 60 |
| gtcatgacgt ttgacatacc tttggaacga gcctcctcct tggaagatgg aagaccgtgt | 120 |
| tcgtggccga cctggcctct cctggcctgt ttcttaagat gcggagtcac atttcaatgg | 180 |
| taggaaaagt ggcttcgtaa aatagaagag cagtcactgt ggaactacca atggcgaga | 240 |
| tgctcggtgc acattggggt gctttgggat aaaagattta tgagccaact attctctggc | 300 |
| accagattct aggccagttt gttccactga agcttttccc acagcagtcc acctctgcag | 360 |
| gctggcagct gaatggcttg ccggtggctc tgtggcaaga tcacactgag atcgatgggt | 420 |
| gagaaggcta ggatgcttgt ctagtgttct tagctgtcac gttggctcct tccaggttgg | 480 |
| ccagacggtg ttggccactc ccttctaaaa cacaggcgcc ctcctggtga cagtgacccg | 540 |
| ccgtggtatg ccttggccca ttccagcagt cccagttatg catttcaagt ttggggtttg | 600 |
| ttctttttcgt taatgttcct ctgtgttgtc agctgtcttc atttcctggg ctaagcagca | 660 |
| ttgggagatg tggaccagag atccactcct taagaaccag tggcgaaaga cactttcttt | 720 |
| cttcactctg aagtagctgg tggt | 744 |

<210> SEQ ID NO 229
<211> LENGTH: 300
<212> TYPE: DNA
<213> ORGANISM: Homo sapien

<400> SEQUENCE: 229

| | |
|---|---|
| cgagtctggg ttttgtctat aaagtttgat ccctcctttt ctcatccaaa tcatgtgaac | 60 |
| cattacacat cgaaataaaa gaaaggtggc agacttgccc aacgccaggc tgacatgtgc | 120 |
| tgcagggttg ttgttttta attattattg ttagaaacgt caccacagt ccctgttaat | 180 |
| ttgtatgtga cagccaactc tgagaaggtc ctatttttcc acctgcagag gatccagtct | 240 |
| cactaggctc ctccttgccc tcacactgga gtctccgcca gtgtgggtgc ccactgacat | 300 |

<210> SEQ ID NO 230
<211> LENGTH: 301
<212> TYPE: DNA

-continued

<213> ORGANISM: Homo sapien

<400> SEQUENCE: 230

| cagcagaaca aatacaaata tgaagagtgc aaagatctca taaaatctat gctgaggaat | 60 |
| gagcgacagt tcaaggagga gaagcttgca gagcagctca agcaagctga ggagctcagg | 120 |
| caatataaag tcctggttca cactcaggaa cgagagctga cccagttaag ggagaagttg | 180 |
| cgggaaggga gagatgcctc cctctcattg aatgagcatc tccaggccct cctcactccg | 240 |
| gatgaaccgg acaagtccca ggggcaggac ctccaagaaa cagacctcgg ccgcgaccac | 300 |
| g | 301 |

<210> SEQ ID NO 231
<211> LENGTH: 301
<212> TYPE: DNA
<213> ORGANISM: Homo sapien

<400> SEQUENCE: 231

| gcaagcacgc tggcaaatct ctgtcaggtc agctccagag aagccattag tcattttagc | 60 |
| caggaactcc aagtccacat ccttggcaac tggggacttg cgcaggttag ccttgaggat | 120 |
| ggcaacacgg gacttctcat caggaagtgg gatgtagatg agctgatcaa gacggccagg | 180 |
| tctgaggatg gcaggatcaa tgatgtcagg ccggttggta ccgccaatga tgaacacatt | 240 |
| ttttttttgtg gacatgccat ccatttctgt caggatctgg ttgatgactc ggtcagcagc | 300 |
| c | 301 |

<210> SEQ ID NO 232
<211> LENGTH: 301
<212> TYPE: DNA
<213> ORGANISM: Homo sapien

<400> SEQUENCE: 232

| agtaggtatt tcgtgagaag ttcaacacca aaactggaac atagttctcc ttcaagtgtt | 60 |
| ggcgacagcg ggcttcctg attctggaat ataactttgt gtaaattaac agccaccttat | 120 |
| agaagagtcc atctgctgtg aaggagagac agagaactct gggttccgtc gtcctgtcca | 180 |
| cgtgctgtac caagtgctgg tgccagcctg ttacctgttc tcactgaaaa tctggctaat | 240 |
| gctcttgtgt atcacttctg attctgacaa tcaatcaatc aatggcctag agcactgact | 300 |
| g | 301 |

<210> SEQ ID NO 233
<211> LENGTH: 301
<212> TYPE: DNA
<213> ORGANISM: Homo sapien

<400> SEQUENCE: 233

| atgactgact tcccagtaag gctctctaag gggtaagtag gaggatccac aggatttgag | 60 |
| atgctaaggc cccagagatc gtttgatcca accctcttat tttcagaggg gaaaatgggg | 120 |
| cctagaagtt acagagcatc tagctggtgc gctggcaccc ctggcctcac acagactccc | 180 |
| gagtagctgg gactacaggc acacagtcac tgaagcaggc cctgttagca attctatgcg | 240 |
| tacaaattaa catgagatga gtagagactt tattgagaaa gcaagagaaa atcctatcaa | 300 |
| c | 301 |

<210> SEQ ID NO 234
<211> LENGTH: 301

```
<212> TYPE: DNA
<213> ORGANISM: Homo sapien

<400> SEQUENCE: 234
aggtcctaca catcgagact catccatgat tgatatgaat ttaaaaatta caagcaaaga      60 catttattc atcatgatgc tttcttttgt ttcttctttt cgttttcttc ttttctttt      120 tcaatttcag caacatactt ctcaatttct tcaggattta aaatcttgag ggattgatct    180
cgcctcatga cagcaagttc aatgtttttg ccacctgact gaaccacttc caggagtgcc   240
ttgatcacca gcttaatggt cagatcatct gcttcaatgg cttcgtcagt atagttcttc    300
t                                                                   301

<210> SEQ ID NO 235
<211> LENGTH: 283
<212> TYPE: DNA
<213> ORGANISM: Homo sapien

<400> SEQUENCE: 235
tggggctgtg catcaggcgg gtttgagaaa tattcaattc tcagcagaag ccagaatttg     60
aattccctca tcttttaggg aatcatttac caggtttgga gaggattcag acagctcagg    120
tgctttcact aatgtctctg aacttctgtc cctctttgtt catggatagt ccaataaata    180
atgttatctt tgaactgatg ctcataggag agaatataag aactctgagt gatatcaaca    240
ttagggattc aaagaaatat tagatttaag ctcacactgg tca                     283

<210> SEQ ID NO 236
<211> LENGTH: 301
<212> TYPE: DNA
<213> ORGANISM: Homo sapien

<400> SEQUENCE: 236
aggtcctcca ccaactgcct gaagcacggt taaaattggg aagaagtata gtgcagcata     60 aatacttta atcgatcag atttccctaa cccacatgca atcttcttca ccagaagagg    120
tcggagcagc atcattaata ccaagcagaa tgcgtaatag ataaatacaa tggtatatag   180
tgggtagacg gcttcatgag tacagtgtac tgtggtatcg taatctggac ttgggttgta    240
aagcatcgtg taccagtcag aaagcatcaa tactcgacat gaacgaatat aaagaacacc    300
a                                                                   301

<210> SEQ ID NO 237
<211> LENGTH: 301
<212> TYPE: DNA
<213> ORGANISM: Homo sapien

<400> SEQUENCE: 237
cagtggtagt ggtggtggac gtggcgttgg tcgtggtgcc ttttttggtg cccgtcacaa     60
actcaatttt tgttcgctcc ttttttggcct tttccaattt gtccatctca attttctggg   120
ccttggctaa tgcctcatag taggagtcct cagaccagcc atgggatcag aacatatcct   180
ttgggtagtt ggtgccaagc tcgtcaatgg cacagaatgg atcagcttct cgtaaatcta   240
gggttccgaa attctttctt cctttggata atgtagttca tatccattcc ctcctttatc    300
t                                                                   301

<210> SEQ ID NO 238
<211> LENGTH: 301
<212> TYPE: DNA
```

<213> ORGANISM: Homo sapien

<400> SEQUENCE: 238

| gggcaggttt | tttttttttt | tttttttgatg | gtgcagaccc | ttgctttatt | tgtctgactt | 60 |
| gttcacagtt | cagcccctg | ctcagaaaac | caacgggcca | gctaaggaga | ggaggaggca | 120 |
| ccttgagact | tccggagtcg | aggctctcca | gggttccca | gcccatcaat | cattttctgc | 180 |
| acccctgcc | tgggaagcag | ctccctgggg | ggtgggaatg | ggtgactaga | agggatttca | 240 |
| gtgtgggacc | caggtctgt | tcttcacagt | aggaggtgga | agggatgact | aatttcttta | 300 |
| t | | | | | | 301 |

<210> SEQ ID NO 239
<211> LENGTH: 239
<212> TYPE: DNA
<213> ORGANISM: Homo sapien

<400> SEQUENCE: 239

| ataagcagct | agggaattct | ttatttagta | atgtcctaac | ataaagttc | acataactgc | 60 |
| ttctgtcaaa | ccatgatact | gagctttgtg | acaacccaga | aataactaag | agaaggcaaa | 120 |
| cataatacct | tagagatcaa | gaaacattta | cacagttcaa | ctgttaaaa | atagctcaac | 180 |
| attcagccag | tgagtagagt | gtgaatgcca | gcatacacag | tatacaggtc | cttcaggga | 239 |

<210> SEQ ID NO 240
<211> LENGTH: 300
<212> TYPE: DNA
<213> ORGANISM: Homo sapien

<400> SEQUENCE: 240

| ggtcctaatg | aagcagcagc | ttccacattt | taacgcaggt | ttacggtgat | actgtccttt | 60 |
| gggatctgcc | ctccagtgga | accttttaag | gaagaagtgg | gcccaagcta | agttccacat | 120 |
| gctgggtgag | ccagatgact | tctgttccct | ggtcactttc | ttcaatgggg | cgaatggggg | 180 |
| ctgccaggtt | tttaaaatca | tgcttcatct | tgaagcacac | ggtcacttca | ccctcctcac | 240 |
| gctgtgggtg | tactttgatg | aaaatacca | ctttgttggc | cttctgaag | ctataatgtc | 300 |

<210> SEQ ID NO 241
<211> LENGTH: 301
<212> TYPE: DNA
<213> ORGANISM: Homo sapien

<400> SEQUENCE: 241

| gaggtctggt | gctgaggtct | ctgggctagg | aagaggagtt | ctgtggagct | ggaagccaga | 60 |
| cctctttgga | ggaaactcca | gcagctatgt | tggtgtctct | gagggaatgc | aacaaggctg | 120 |
| ctcctccatg | tattggaaaa | ctgcaaactg | gactcaactg | gaaggaagtg | ctgctgccag | 180 |
| tgtgaagaac | cagcctgagg | tgacagaaac | ggaagcaaac | aggaacagcc | agtctttct | 240 |
| tcctcctcct | gtcatacggt | ctctctcaag | catcctttgt | tgtcagggc | ctaaaaggga | 300 |
| g | | | | | | 301 |

<210> SEQ ID NO 242
<211> LENGTH: 301
<212> TYPE: DNA
<213> ORGANISM: Homo sapien

<400> SEQUENCE: 242

| ccgaggtcct | gggatgcaac | caatcactct | gtttcacgtg | acttttatca | ccatacaatt | 60 |

```
tgtggcattt cctcattttc tacattgtag aatcaagagt gtaaataaat gtatatcgat        120
gtcttcaaga atatatcatt cctttttcac tagaacccat tcaaaatata agtcaagaat        180
cttaatatca acaaatatat caagcaaact ggaaggcaga ataactacca taatttagta        240
taagtaccca aagttttata aatcaaaagc cctaatgata accatttta  gaattcaatc        300 a                                                                        301
```

```
<210> SEQ ID NO 243
<211> LENGTH: 301
<212> TYPE: DNA
<213> ORGANISM: Homo sapien

<400> SEQUENCE: 243
aggtaagtcc cagtttgaag ctcaaaagat ctggtatgag cataggctca tcgacgacat         60 ggtgcccaa  gctatgaaat cagagggagg cttcatctgg gcctgtaaaa actatgatgg        120
tgacgtgcag tcggactctg tggcccaagg gtatggctct tcggcatga  tgaccagcgt        180 gctggtttgt ccagatggca agacagtaga agcagaggct gcccacggga ctgtaacccg        240
tcactaccgc atgttccaga aggacagga  gacgtccacc aatcccattg cttccatttt        300
t                                                                        301
```

```
<210> SEQ ID NO 244
<211> LENGTH: 300
<212> TYPE: DNA
<213> ORGANISM: Homo sapien

<400> SEQUENCE: 244
gctggtttgc aagaatgaaa tgaatgattc tacagctagg acttaacctt gaaatggaaa         60
gtcatgcaat cccatttgca ggatctgtct gtgcacatgc ctctgtagag agcagcattc        120
ccagggacct tggaaacagt tgacactgta aggtgcttgc tccccaagac acatcctaaa        180
aggtgttgta atggtgaaaa cgtcttcctt ctttattgcc ccttcttatt tatgtgaaca        240
actgtttgtc ttttgtgtat cttttttaaa ctgtaaagtt caattgtgaa aatgaatatc        300
```

```
<210> SEQ ID NO 245
<211> LENGTH: 301
<212> TYPE: DNA
<213> ORGANISM: Homo sapien

<400> SEQUENCE: 245
gtctgagtat ttaaaatgtt attgaaatta tccccaacca atgttagaaa agaaagaggt         60
tatatactta gataaaaaat gaggtgaatt actatccatt gaaatcatgc tcttagaatt        120
aaggccagga gatattgtca ttaatgtara cttcaggaca ctagagtata gcagccctat        180
gttttcaaag agcagagatg caattaaata ttgtttagca tcaaaaggc  cactcaatac        240 agctaataaa atgaaagacc taatttctaa agcaattctt tataatttac aaagttttaa        300
g                                                                        301
```

```
<210> SEQ ID NO 246
<211> LENGTH: 301
<212> TYPE: DNA
<213> ORGANISM: Homo sapien

<400> SEQUENCE: 246
ggtctgtcct acaatgcctg cttcttgaaa gaagtcggca ctttctagaa tagctaaata         60
```

| | |
|---|---|
| acctgggctt attttaaaga actatttgta gctcagattg gttttcctat ggctaaaata | 120 |
| agtgcttctt gtgaaaatta aataaaacag ttaattcaaa gccttgatat atgttaccac | 180 |
| taacaatcat actaaatata ttttgaagta caaagtttga catgctctaa agtgacaacc | 240 |
| caaatgtgtc ttacaaaaca cgttcctaac aaggtatgct ttacactacc aatgcagaaa | 300 |
| c | 301 |

<210> SEQ ID NO 247
<211> LENGTH: 301
<212> TYPE: DNA
<213> ORGANISM: Homo sapien

<400> SEQUENCE: 247

| | |
|---|---|
| aggtcctttg gcagggctca tggatcagag ctcaaactgg agggaaaggc atttcgggta | 60 |
| gcctaagagg gcgactggcg gcagcacaac caaggaaggc aaggttgttt ccccacgct | 120 |
| gtgtcctgtg ttcaggtgcg acacacaatc ctcatgggaa caggatcacc catgcgctgc | 180 |
| ccttgatgat caaggttggg gcttaagtgg attaagggag gcaagttctg ggttccttgc | 240 |
| cttttcaaac catgaagtca ggctctgtat ccctcctttt cctaactgat attctaacta | 300 |
| a | 301 |

<210> SEQ ID NO 248
<211> LENGTH: 301
<212> TYPE: DNA
<213> ORGANISM: Homo sapien

<400> SEQUENCE: 248

| | |
|---|---|
| aggtccttgg agatgccatt tcagccgaag gactcttctw ttcggaagta caccctcact | 60 |
| attaggaaga ttcttagggg taattttct gaggaaggag aactagccaa cttaagaatt | 120 |
| acaggaagaa agtggtttgg aagacagcca agaaataaa agcagattaa attgtatcag | 180 |
| gtacattcca gcctgttggc aactccataa aaacatttca gattttaatc ccgaatttag | 240 |
| ctaatgagac tggattttg ttttttatgt tgtgtgtcgc agagctaaaa actcagttcc | 300 |
| c | 301 |

<210> SEQ ID NO 249
<211> LENGTH: 301
<212> TYPE: DNA
<213> ORGANISM: Homo sapien

<400> SEQUENCE: 249

| | |
|---|---|
| gtccagagga agcacctggt gctgaactag gcttgccctg ctgtgaactt gcacttggag | 60 |
| ccctgacgct gctgttctcc ccgaaaaacc cgaccgacct ccgcgatctc cgtcccgccc | 120 |
| ccagggagac acagcagtga ctcagagctg gtcgcacact gtgcctccct cctcaccgcc | 180 |
| catcgtaatg aattattttg aaaattaatt ccaccatcct ttcagattct ggatggaaag | 240 |
| actgaatctt tgactcagaa ttgtttgctg aaaagaatga tgtgactttc ttagtcattt | 300 |
| a | 301 |

<210> SEQ ID NO 250
<211> LENGTH: 301
<212> TYPE: DNA
<213> ORGANISM: Homo sapien

<400> SEQUENCE: 250

| | |
|---|---|
| ggtctgtgac aaggacttgc aggctgtggg aggcaagtga cccttaacac tacacttctc | 60 |

```
cttatcttta ttggcttgat aaacataatt atttctaaca ctagcttatt tccagttgcc      120
cataagcaca tcagtacttt tctctggctg aatagtaaa ctaaagtatg gtacatctac       180
ctaaaagact actatgtgga ataatacata ctaatgaagt attacatgat ttaaagacta      240
caataaaacc aaacatgctt ataacattaa gaaaacaat aaagatacat gattgaaacc       300
a                                                                     301

<210> SEQ ID NO 251
<211> LENGTH: 301
<212> TYPE: DNA
<213> ORGANISM: Homo sapien

<400> SEQUENCE: 251
gccgaggtcc tacatttggc ccagtttccc cctgcatcct ctccagggcc cctgcctcat       60
agacaacctc atagagcata ggagaactgg ttgccctggg ggcaggggga ctgtctggat      120 ggcagggtc ctcaaaatg ccactgtcac tgccaggaaa tgcttctgag cagtacacct        180
cattgggatc aatgaaaagc ttcaagaaat cttcaggctc actctcttga aggcccggaa      240
cctctggagg ggggcagtgg aatcccagct ccaggacgga tcctgtcgaa aagatatcct     300
c                                                                     301

<210> SEQ ID NO 252
<211> LENGTH: 301
<212> TYPE: DNA
<213> ORGANISM: Homo sapien

<400> SEQUENCE: 252
gcaaccaatc actctgtttc acgtgacttt tatcaccata caatttgtgg catttcctca       60
ttttctacat tgtagaatca agagtgtaaa taaatgtata tcgatgtctt caagaatata     120
tcattccttt ttcactagga acccattcaa aatataagtc aagaatctta atatcaacaa      180
atatatcaag caaactggaa ggcagaataa ctaccataat ttagtataag tacccaaagt      240
tttataaatc aaaagcccta atgataacca tttttagaat tcaatcatca ctgtagaatc      300
a                                                                     301

<210> SEQ ID NO 253
<211> LENGTH: 301
<212> TYPE: DNA
<213> ORGANISM: Homo sapien

<400> SEQUENCE: 253
ttccctaaga agatgttatt ttgttgggtt ttgttccccc tccatctcga ttctcgtacc       60
caactaaaaa aaaaaaataa agaaaaaatg tgctgcgttc tgaaaaataa ctccttagct      120
tggtctgatt gttttcagac cttaaaatat aaacttgttt cacaagcttt aatccatgtg      180
gatttttttt cttagagaac cacaaaacat aaaaggagca agtcggactg aatacctgtt      240
tccatagtgc ccacagggta ttcctcacat tttctccata ggaaaatgct ttttcccaag      300
g                                                                     301

<210> SEQ ID NO 254
<211> LENGTH: 301
<212> TYPE: DNA
<213> ORGANISM: Homo sapien

<400> SEQUENCE: 254
```

```
cgctgcgcct ttcccttggg ggaggggcaa ggccagaggg ggtccaagtg cagcacgagg    60
aacttgacca attcccttga agcgggtggg ttaaaccctg taaatgggaa caaaatcccc   120
ccaaatctct tcatcttacc ctggtggact cctgactgta aatttttttg gttgaaacaa   180
gaaaaaaata aagctttgga cttttcaagg ttgcttaaca ggtactgaaa gactggcctc   240
acttaaactg agccaggaaa agctgcagat ttattaatgg gtgtgttagt gtgcagtgcc   300
t                                                                  301
```

<210> SEQ ID NO 255
<211> LENGTH: 302
<212> TYPE: DNA
<213> ORGANISM: Homo sapien

<400> SEQUENCE: 255

```
agcttttttt tttttttttt tttttttttt ttcattaaaa aatagtgctc tttattataa    60
attactgaaa tgtttctttt ctgaatataa atataaatat gtgcaaagtt tgacttggat   120
tgggattttg ttgagttctt caagcatctc ctaatacccct caagggcctg agtagggggg   180
aggaaaaagg actggaggtg gaatctttat aaaaaacaag agtgattgag gcagattgta   240
aacattatta aaaacaaga aacaaacaaa aaaatagaga aaaaaaccac cccaacacac   300
aa                                                                 302
```

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256

```
gttccagaaa acattgaagg tggcttccca agtctaact agggatacccc cctctagcct    60 aggaccctcc tccccacacc tcaatccacc aaaccatcca taatgcaccc agataggccc   120 accccccaaaa gcctggacac cttgagcaca cagttatgac caggacagac tcatctctat   180
aggcaaatag ctgctggcaa actggcatta cctggtttgt ggggatgggg gggcaagtgt   240
gtggcctctc ggcctggtta gcaagaacat tcagggtagg cctaagttan tcgtgttagt   300
t                                                                  301
```

<210> SEQ ID NO 257
<211> LENGTH: 301
<212> TYPE: DNA
<213> ORGANISM: Homo sapien

<400> SEQUENCE: 257

```
gttgtggagg aactctggct tgctcattaa gtcctactga ttttcactat cccctgaatt    60
tccccactta ttttttgtctt tcactatcgc aggccttaga agaggtctac ctgcctccag   120
tcttacctag tccagtctac ccctggagt tagaatggcc atcctgaagt gaaaagtaat   180
gtcacattac tcccttcagt gatttcttgt agaagtgcca atccctgaat gccaccaaga   240
tcttaatctt cacatctta atcttatctc tttgactcct ctttacaccg gagaaggctc   300
c                                                                  301
```

<210> SEQ ID NO 258
<211> LENGTH: 301

```
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 258
cagcagtagt agatgccgta tgccagcacg cccagcactc ccaggatcag caccagcacc        60
aggggcccag ccaccaggcg cagaagcaag ataaacagta ggctcaagac cagagccacc       120
cccagggcaa caagaatcca ataccaggac tgggcaaaat cttcaaagat cttaacactg       180
atgtctcggg cattgaggct gtcaataana cgctgatccc ctgctgtatg gtggtgtcat       240
tggtgatccc tgggagcgcc ggtggagtaa cgttggtcca tggaaagcag cgcccacaac       300
t                                                                      301

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259
tcatatatgc aaacaaatgc agactangcc tcaggcagag actaaaggac atctcttggg        60
gtgtcctgaa gtgatttgga cccctgaggg cagacaccta agtaggaatc ccagtgggaa       120
gcaaagccat aaggaagccc aggattcctt gtgatcagga agtgggccag gaaggtctgt       180
tccagctcac atctcatctg catgcagcac ggaccggatg cgcccactgg gtcttggctt       240
ccctcccatc ttctcaagca gtgtccttgt tgagccattt gcatccttgg ctccaggtgg       300
c                                                                      301

<210> SEQ ID NO 260
<211> LENGTH: 301
<212> TYPE: DNA
<213> ORGANISM: Homo sapien

<400> SEQUENCE: 260
ttttttttct ccctaaggaa aaagaaggaa caagtctcat aaaaccaaat aagcaatggt        60
aaggtgtctt aacttgaaaa agattaggag tcactggttt acaagttata attgaatgaa       120
agaactgtaa cagccacagt tggccatttc atgccaatgg cagcaaacaa caggattaac       180
tagggcaaaa taaataagtg tgtggaagcc ctgataagtg cttaataaac agactgattc       240
actgagacat cagtacctgc ccgggcggcc gctcgagccg aattctgcag atatccatca       300
c                                                                      301

<210> SEQ ID NO 261
<211> LENGTH: 301
<212> TYPE: DNA
<213> ORGANISM: Homo sapien

<400> SEQUENCE: 261
aaatattcga gcaaatcctg taactaatgt gtctccataa aaggctttga actcagtgaa        60
tctgcttcca tccacgattc tagcaatgac ctctcggaca tcaaagctcc tcttaaggtt       120
agcaccaact attccataca attcatcagc aggaaataaa ggctcttcag aaggttcaat       180
```

```
ggtgacatcc aatttcttct gataatttag attcctcaca accttcctag ttaagtgaag    240
ggcatgatga tcatccaaag cccagtggtc acttactcca gactttctgc aatgaagatc    300
a                                                                    301

<210> SEQ ID NO 262
<211> LENGTH: 301
<212> TYPE: DNA
<213> ORGANISM: Homo sapien

<400> SEQUENCE: 262
gaggagagcc tgttacagca tttgtaagca cagaatactc caggagtatt tgtaattgtc     60
tgtgagcttc ttgccgcaag tctctcagaa atttaaaaag atgcaaatcc ctgagtcacc    120
cctagacttc ctaaaccaga tcctctgggg ctggaacctg gcactctgca tttgtaatga    180
gggctttctg gtgcacacct aattttgtgc atctttgccc taaatcctgg attagtgccc    240
catcattacc cccacattat aatgggatag attcagagca gatactctcc agcaaagaat    300
c                                                                    301

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263
tttagcttgt ggtaaatgac tcacaaaact gattttaaaa tcaagttaat gtgaattttg     60
aaaattacta cttaatccta attcacaata acaatggcat taaggtttga cttgagttgg    120
ttcttagtat tatttatggt aaataggctc ttaccacttg caaataactg gccacatcat    180
taatgactga cttcccagta aggctctcta aggggtaagt angaggatcc acaggatttg    240
agatgctaag gccccagaga tcgtttgatc caaccctctt atttttcagag gggaaaatgg    300 g                                                                    301

<210> SEQ ID NO 264
<211> LENGTH: 301
<212> TYPE: DNA
<213> ORGANISM: Homo sapien

<400> SEQUENCE: 264
aaagacgtta aaccactcta ctaccacttg tggaactctc aaagggtaaa tgacaaascc     60
aatgaatgac tctaaaaaca atatttacat ttaatggttt gtagacaata aaaaaacaag    120
gtggatagat ctagaattgt aacattttaa gaaaaccata scatttgaca gatgagaaag    180
ctcaattata gatgcaaagt tataactaaa ctactatagt agtaaagaaa tacatttcac    240
acccttcata taaattcact atcttggctt gaggcactcc ataaaatgta tcacgtgcat    300
a                                                                    301

<210> SEQ ID NO 265
<211> LENGTH: 301
<212> TYPE: DNA
<213> ORGANISM: Homo sapien

<400> SEQUENCE: 265
tgcccaagtt atgtgtaagt gtatccgcac ccagaggtaa aactacactg tcatctttgt     60
```

```
cttcttgtga cgcagtattt cttctctggg gagaagccgg gaagtcttct cctggctcta    120
catattcttg gaagtctcta atcaactttt gttccatttg tttcatttct tcaggaggga    180
ttttcagttt gtcaacatgt tctctaacaa cacttgccca tttctgtaaa gaatccaaag    240
cagtccaagg ctttgacatg tcaacaacca gcataactag agtatccttc agagatacgg    300
c                                                                   301

<210> SEQ ID NO 266
<211> LENGTH: 301
<212> TYPE: DNA
<213> ORGANISM: Homo sapien

<400> SEQUENCE: 266
taccgtctgc ccttcctccc atccaggcca tctgcgaatc tacatgggtc ctcctattcg     60
acaccagatc actctttcct ctacccacag gcttgctatg agcaagagac acaacctcct    120
ctcttctgtg ttccagcttc ttttcctgtt ctcccaccc cttaagttct attcctgggg     180
atagagacac caatacccat aacctctctc ctaagcctcc ttataaccca gggtgcacag    240
cacagactcc tgacaactgg taaggccaat gaactgggag ctcacagctg ctgtgcctg     300 a                                                                   301

<210> SEQ ID NO 267
<211> LENGTH: 301
<212> TYPE: DNA
<213> ORGANISM: Homo sapien

<400> SEQUENCE: 267
aaagagcaca ggccagctca gcctgccctg gccatctaga ctcagcctgg ctccatgggg     60
gttctcagtg ctgagtccat ccaggaaaag ctcacctaga ccttctgagg ctgaatcttc    120
atcctcacag gcagcttctg agagcctgat attcctagcc ttgatggtct ggagtaaagc    180
ctcattctga ttcctctcct tcttttcttt caagttggct ttcctcacat ccctctgttc    240
aattcgcttc agcttgtctg ctttagccct catttccaga agcttcttct ctttggcatc    300
t                                                                   301

<210> SEQ ID NO 268
<211> LENGTH: 301
<212> TYPE: DNA
<213> ORGANISM: Homo sapien

<400> SEQUENCE: 268
aatgtctcac tcaactactt cccagcctac cgtggcctaa ttctgggagt tttcttctta     60
gatcttggga gagctggttc ttctaaggag aaggaggaag gacagatgta actttggatc    120
tcgaagagga agtctaatgg aagtaattag tcaacggtcc ttgtttagac tcttggaata    180
tgctgggtgg ctcagtgagc ccttttggag aaagcaagta ttattcttaa ggagtaacca    240
cttcccattg ttctactttc taccatcatc aattgtatat tatgtattct ttggagaact    300
a                                                                   301

<210> SEQ ID NO 269
<211> LENGTH: 301
<212> TYPE: DNA
<213> ORGANISM: Homo sapien

<400> SEQUENCE: 269
```

| | |
|---|---|
| taacaatata cactagctat ctttttaact gtccatcatt agcaccaatg aagattcaat | 60 |
| aaaattacct ttattcacac atctcaaaac aattctgcaa attcttagtg aagtttaact | 120 |
| atagtcacag accttaaata ttcacattgt tttctatgtc tactgaaaat aagttcacta | 180 |
| cttttctgga tattctttac aaaatcttat taaaattcct ggtattatca cccccaatta | 240 |
| tacagtagca caaccacctt atgtagtttt tacatgatag ctctgtagaa gtttcacatc | 300 |
| t | 301 |

<210> SEQ ID NO 270
<211> LENGTH: 301
<212> TYPE: DNA
<213> ORGANISM: Homo sapien

<400> SEQUENCE: 270

| | |
|---|---|
| cattgaagag cttttgcgaa acatcagaac acaagtgctt ataaaattaa ttaagcctta | 60 |
| cacaagaata catattcctt ttatttctaa ggagttaaac atagatgtag ctgatgtgga | 120 |
| gagcttgctg gtgcagtgca tattggataa cactattcat ggccgaattg atcaagtcaa | 180 |
| ccaactcctt gaactggatc atcagaagaa gggtggtgca cgatatactg cactagataa | 240 |
| tggaccaacc aactaaattc tctcaccagg ctgtatcagt aaactggctt aacagaaaac | 300 |
| a | 301 |

<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271

| | |
|---|---|
| aaaaggttct cataagatta acaatttaaa taaatatttg atagaacatt ctttctcatt | 60 |
| tttatagctc atctttaggg ttgatattca gttcatgctt cccttgctgt tcttgatcca | 120 |
| gaattgcaat cacttcatca gcctgtattc gctccaattc tctataaagt gggtccaagg | 180 |
| tgaaccacag agccacagca cacctctttc ccttggtgac tgccttcacc ccatganggt | 240 |
| tctctcctcc agatganaac tgatcatgcg cccacatttt gggtttttata gaagcagtca | 300 |
| c | 301 |

<210> SEQ ID NO 272
<211> LENGTH: 301
<212> TYPE: DNA
<213> ORGANISM: Homo sapien

<400> SEQUENCE: 272

| | |
|---|---|
| taaattgcta agccacagat aacaccaatc aaatggaaca aatcactgtc ttcaaatgtc | 60 |
| ttatcagaaa accaaatgag cctggaatct tcataatacc taaacatgcc gtatttagga | 120 |
| tccaataatt ccctcatgat gagcaagaaa aattctttgc gcacccctcc tgcatccaca | 180 |
| gcatcttctc caacaaatat aaccttgagt ggcttcttgt aatctatgtt ctttgttttc | 240 |
| ctaaggactt ccattgcatc tcctacaata ttttctctac gcaccactag aattaagcag | 300 |
| g | 301 |

<210> SEQ ID NO 273
<211> LENGTH: 301

```
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 273
acatgtgtgt atgtgtatct ttgggaaaan aanaagacat cttgtttayt attttttgg      60 agagangctg ggacatggat aatcacwtaa tttgctayta tyactttaat ctgactygaa    120
gaaccgtcta aaaataaaat ttaccatgtc dtatattcct tatagtatgc ttatttcacc    180
ttytttctgt ccagagagag tatcagtgac ananatttma gggtgaamac atgmattggt    240
gggacttnty tttacngagm accctgcccg sgcgccctcg makcngantt ccgcsananc    300
t                                                                    301

<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274
cttatatact ctttctcaga ggcaaaagag gagatgggta atgtagacaa ttctttgagg     60
aacagtaaat gattattaga gagaangaat ggaccaagga gacagaaatt aacttgtaaa   120
tgattctctt tggaatctga atgagatcaa gaggccagct ttagcttgtg gaaaagtcca   180
tctaggtatg gttgcattct cgtcttcttt tctgcagtag ataatgaggt aaccgaaggc   240
aattgtgctt cttttgataa gaagctttct tggtcatatc aggaaattcc aganaaagtc   300
c                                                                   301

<210> SEQ ID NO 275
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275
tcggtgtcag cagcacgtgg cattgaacat tgcaatgtgg agcccaaacc acagaaaatg     60
gggtgaaatt ggccaacttt ctattaactt atgttggcaa ttttgccacc aacagtaagc   120
tggcccttct aataaaagaa aattgaaagg tttctcacta aacggaatta agtagtggag   180
tcaagagact cccaggcctc agcgtacctg cccgggcggc cgctcgaagc cgaattctgc   240
agatatccat cacactggcg gncgctcgan catgcatcta aaggnccaa ttcgccctat    300 a                                                                   301

<210> SEQ ID NO 276
<211> LENGTH: 301
<212> TYPE: DNA
<213> ORGANISM: Homo sapien

<400> SEQUENCE: 276
tgtacacata ctcaataaat aaatgactgc attgtggtat tattactata ctgattatat     60
```

```
ttatcatgtg acttctaatt agaaaatgta tccaaaagca aaacagcaga tatacaaaat    120
taaagagaca gaagatagac attaacagat aaggcaactt atacattgag aatccaaatc    180
caatacattt aaacatttgg gaaatgaggg ggacaaatgg aagccagatc aaatttgtgt    240
aaaactattc agtatgtttc ccttgcttca tgtctgagaa ggctctcctt caatggggat    300
g                                                                   301
```

<210> SEQ ID NO 277
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277

```
tttgttgatg tcagtatttt attacttgcg ttatgagtgc tcacctggga aattctaaag    60
atacagagga cttggaggaa gcagagcaac tgaatttaat ttaaaagaag gaaaacattg    120
gaatcatggc actcctgata ctttcccaaa tcaacactct caatgcccca ccctcgtcct    180
caccatagtg gggagactaa agtggccacg gatttgcctt angtgtgcag tgcgttctga    240
gttcnctgtc gattacatct gaccagtctc ctttttccga agtccntccg ttcaatcttg    300
c                                                                   301
```

<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278

```
taccactaca ctccagcctg ggcaacagag caagacctgt ctcaaagcat aaaatggaat    60
aacatatcaa atgaaacagg gaaaatgaag ctgacaattt atggaagcca gggcttgtca    120
cagtctctac tgttattatg cattacctgg gaatttatat aagcccttaa taataatgcc    180
aatgaacatc tcatgtgtgc tcacaatgtt ctggcactat tataagtgct tcacaggttt    240
tatgtgttct tcgtaacttt atggantagg tactcggccg cgaacacgct aagccgaatt    300
c                                                                   301
```

<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279

```
aaagcaggaa tgacaaagct tgcttttctg gtatgttcta ggtgtattgt gactttact     60 gttatattaa ttgccaatat aagtaaatat agattatata tgtatagtgt ttcacaaagc    120
ttagaccttt accttccagc caccccacag tgcttgatat ttcagagtca gtcattggtt    180
atacatgtgt agttccaaag cacataagct agaanaanaa atatttctag ggagcactac    240
catctgtttt cacatgaaat gccacacaca tagaactcca acatcaattt cattgcacag    300
``` a                                                                                301

<210> SEQ ID NO 280
<211> LENGTH: 301
<212> TYPE: DNA
<213> ORGANISM: Homo sapien

<400> SEQUENCE: 280
ggtactggag ttttcctccc ctgtgaaaac gtaactactg ttgggagtga attgaggatg    60
tagaaaggtg gtggaaccaa attgtggtca atggaaatag gagaatatgg ttctcactct   120
tgagaaaaaa acctaagatt agcccaggta gttgcctgta acttcagttt ttctgcctgg   180
gtttgatata gtttagggtt ggggttagat taagatctaa attacatcag gacaaagaga   240
cagactatta actccacagt taattaagga ggtatgttcc atgtttattt gttaaagcag   300
t                                                                            301

<210> SEQ ID NO 281
<211> LENGTH: 301
<212> TYPE: DNA
<213> ORGANISM: Homo sapien

<400> SEQUENCE: 281
aggtacaaga aggggaatgg gaaagagctg ctgctgtggc attgttcaac ttggatattc    60
gccgagcaat ccaaatcctg aatgaagggg catcttctga aaaggagat ctgaatctca   120 atgtggtagc aatggctta tcgggttata cggatgagaa gaactcccct tggagagaaa   180
tgtgtagcac actgcgatta cagctaaata acccgtattt gtgtgtcatg tttgcatttc   240
tgacaagtga aacaggatct tacgatggag ttttgtatga aaacaaagtt gcagtacctc   300
g                                                                            301

<210> SEQ ID NO 282
<211> LENGTH: 301
<212> TYPE: DNA
<213> ORGANISM: Homo sapien

<400> SEQUENCE: 282
caggtactac agaattaaaa tactgacaag caagtagttt cttggcgtgc acgaattgca    60
tccagaaccc aaaaattaag aaattcaaaa agacattttg tgggcacctg ctagcacaga   120
agcgcagaag caaagcccag gcagaaccat gctaaccta cagctcagcc tgcacagaag   180
cgcagaagca aagcccaggc agaaccatgc taaccttaca gctcagcctg cacagaagcg   240
cagaagcaaa gcccaggcag aacatgctaa ccttacagct cagcctgcac agaagcacag   300
a                                                                            301

<210> SEQ ID NO 283
<211> LENGTH: 301
<212> TYPE: DNA
<213> ORGANISM: Homo sapien

<400> SEQUENCE: 283
atctgtatac ggcagacaaa ctttatarag tgtagagagg tgagcgaaag gatgcaaaag    60
cactttgagg gctttataat aatatgctgc ttgaaaaaaa aaatgtgtag ttgatactca   120
gtgcatctcc agacatagta aggggttgct ctgaccaatc aggtgatcat ttttctatc   180 acttcccagg ttttatgcaa aaattttgtt aaattctata atggtgatat gcatctttta   240

| | |
|---|---|
| ggaaacatat acatttttaa aaatctattt tatgtaagaa ctgacagacg aatttgcttt | 300 |
| g | 301 |

<210> SEQ ID NO 284
<211> LENGTH: 301
<212> TYPE: DNA
<213> ORGANISM: Homo sapien

<400> SEQUENCE: 284

| | |
|---|---|
| caggtacaaa acgctattaa gtggcttaga atttgaacat tgtggtctt tatttacttt | 60 |
| gcttcgtgtg tgggcaaagc aacatcttcc ctaaatatat attaccaaga aaagcaagaa | 120 |
| gcagattagg tttttgacaa acaaacagg ccaaaagggg gctgacctgg agcagagcat | 180 |
| ggtgagaggc aaggcatgag agggcaagtt tgttgtggac agatctgtgc ctactttatt | 240 |
| actggagtaa aagaaaacaa agttcattga tgtcgaagga tatatacagt gttagaaatt | 300 |
| a | 301 |

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285

| | |
|---|---|
| acatcaccat gatcggatcc cccacccatt atacgttgta tgtttacata aatactcttc | 60 |
| aatgatcatt agtgttttaa aaaaaatact gaaaactcct tctgcatccc aatctctaac | 120 |
| caggaaagca aatgctattt acagacctgc aagccctccc tcaaacnaaa ctatttctgg | 180 |
| attaaatatg tctgacttct tttgaggtca cacgactagg caaatgctat ttacgatctg | 240 |
| caaaagctgt ttgaagagtc aaagccccca tgtgaacacg atttctggac cctgtaacag | 300 |
| t | 301 |

<210> SEQ ID NO 286
<211> LENGTH: 301
<212> TYPE: DNA
<213> ORGANISM: Homo sapien

<400> SEQUENCE: 286

| | |
|---|---|
| taccactgca ttccagcctg ggtgacagag tgagactccg tctccaaaaa aaactttgct | 60 |
| tgtatattat ttttgcctta cagtggatca ttctagtagg aaaggacagt aagatttttt | 120 |
| atcaaaatgt gtcatgccag taagagatgt tatattcttt tctcatttct tccccaccca | 180 |
| aaaataagct accatatagc ttataagtct caaattttg ccttttacta aaatgtgatt | 240 |
| gtttctgttc attgtgtatg cttcatcacc tatattaggc aaattccatt ttttcccttg | 300 |
| t | 301 |

<210> SEQ ID NO 287
<211> LENGTH: 301
<212> TYPE: DNA
<213> ORGANISM: Homo sapien

<400> SEQUENCE: 287

| | |
|---|---|
| tacagatctg ggaactaaat attaaaaatg agtgtggctg gatatatgga gaatgttggg | 60 |
| cccagaagga acgtagagat cagatattac aacagctttg ttttgagggt tagaaatatg | 120 |

```
aaatgatttg gttatgaacg cacagtttag gcagcagggc cagaatcctg accctctgcc    180
ccgtggttat ctcctcccca gcttggctgc ctcatgttat cacagtattc cattttgttt    240
gttgcatgtc ttgtgaagcc atcaagattt tctcgtctgt tttcctctca ttggtaatgc    300
t                                                                   301
```

<210> SEQ ID NO 288
<211> LENGTH: 301
<212> TYPE: DNA
<213> ORGANISM: Homo sapien

<400> SEQUENCE: 288

```
gtacacctaa ctgcaaggac agctgaggaa tgtaatgggc agccgctttt aaagaagtag     60
agtcaatagg aagacaaatt ccagttccag ctcagtctgg gtatctgcaa agctgcaaaa    120
gatctttaaa gacaatttca agagaatatt tccttaaagt tggcaatttg gagatcatac    180
aaaagcatct gcttttgtga tttaatttag ctcatctggc cactggaaga atccaaacag    240
tctgccttaa ttttggatga atgcatgatg gaaattcaat aatttagaaa gttaaaaaaa    300
a                                                                   301
```

<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

```
ggtacactgt ttccatgtta tgtttctaca cattgctacc tcagtgctcc tggaaactta     60
gcttttgatg tctccaagta gtccaccttc atttaactct ttgaaactgt atcatctttg    120
ccaagtaaga gtggtggcct atttcagctg ctttgacaaa atgactggct cctgacttaa    180
cgttctataa atgaatgtgc tgaagcaaag tgcccatggt ggcggcgaan aagagaaaga    240
tgtgttttgt tttggactct ctgtggtccc ttccaatgct gtgggtttcc aaccagngga    300
a                                                                   301
```

<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290

```
acactgagct cttcttgata aatatacaga atgcttggca tatacaagat tctatactac     60
tgactgatct gttcatttct ctcacagctc ttacccccaa aagcttttcc accctaagtg    120
ttctgacctc cttttctaat cacagtaggg atagaggcag anccacctac aatgaacatg    180
gagttctatc aagaggcaga aacagcacag aatcccagtt ttaccattcg ctagcagtgc    240
tgccttgaac aaaaacattt ctccatgtct cattttcttc atgcctcaag taacagtgag    300
a                                                                   301
```

<210> SEQ ID NO 291

```
<211> LENGTH: 301
<212> TYPE: DNA
<213> ORGANISM: Homo sapien

<400> SEQUENCE: 291
caggtaccaa tttcttctat cctagaaaca tttcatttta tgttgttgaa acataacaac      60
tatatcagct agatttttttt tctatgcttt acctgctatg gaaaatttga cacattctgc    120
tttactcttt tgtttatagg tgaatcacaa aatgtatttt tatgtattct gtagttcaat    180
agccatggct gtttacttca tttaatttat ttagcataaa gacattatga aaaggcctaa    240
acatgagctt cacttcccca ctaactaatt agcatctgtt atttcttaac cgtaatgcct    300
a                                                                     301

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292 acctttagt agtaatgtct aataataaat aagaaatcaa ttttataagg tccatatagc       60
tgtattaaat aattttttaag tttaaaagat aaaataccat cattttaaat gttggtattc    120
aaaaccaaag natataaccg aaaggaaaaa cagatgagac ataaaatgat ttgcnagatg    180
ggaaatatag tasttyatga atgttnatta aattccagtt ataatagtgg ctacacactc    240
tcactacaca cacagacccc acagtcctat atgccacaaa cacatttcca taacttgaaa    300
a                                                                     301

<210> SEQ ID NO 293
<211> LENGTH: 301
<212> TYPE: DNA
<213> ORGANISM: Homo sapien

<400> SEQUENCE: 293
ggtaccaagt gctggtgcca gcctgttacc tgttctcact gaaaagtctg gctaatgctc      60
ttgtgtagtc acttctgatt ctgacaatca atcaatcaat ggcctagagc actgactgtt    120
aacacaaacg tcactagcaa agtagcaaca gctttaagtc taaatacaaa gctgttctgt    180
gtgagaattt tttaaaaggc tacttgtata ataaccttg tcatttttaa tgtacctcgg     240
ccgcgaccac gctaagccga attctgcaga tatccatcac actggcggcc gctcgagcat    300
g                                                                     301

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294
tgacccataa caatatacac tagctatctt tttaactgtc catcattagc accaatgaag      60
attcaataaa attaccttta ttcacacatc tcaaaacaat tctgcaaatt cttagtgaag    120
tttaactata gtcacaganc ttaaatattc acattgtttt ctatgtctac tgaaataag     180
```

```
ttcactactt ttctgggata ttctttacaa aatcttatta aaattcctgg tattatcacc      240
cccaattata cagtagcaca accaccttat gtagtttta catgatagct ctgtagaggt      300
t                                                                     301
```

<210> SEQ ID NO 295
<211> LENGTH: 305
<212> TYPE: DNA
<213> ORGANISM: Homo sapien

<400> SEQUENCE: 295

```
gtactctttc tctccctcc tctgaattta attctttcaa cttgcaattt gcaaggatta       60
cacatttcac tgtgatgtat attgtgttgc aaaaaaaaaa gtgtctttgt ttaaaattac     120
ttggtttgtg aatccatctt gctttttccc cattggaact agtcattaac ccatctctga    180
actggtagaa aaacrtctga agagctagtc tatcagcatc tgacaggtga attggatggt    240
tctcagaacc atttcaccca gacagcctgt ttctatcctg tttaataaat tagtttgggt    300
tctct                                                                305
```

<210> SEQ ID NO 296
<211> LENGTH: 301
<212> TYPE: DNA
<213> ORGANISM: Homo sapien

<400> SEQUENCE: 296

```
aggtactatg ggaagctgct aaaataatat ttgatagtaa aagtatgtaa tgtgctatct     60
cacctagtag taaactaaaa ataaactgaa actttatgga atctgaagtt attttccttg   120
attaaataga attaataaac caatatgagg aaacatgaaa ccatgcaatc tactatcaac   180
tttgaaaaag tgattgaacg aaccacttag ctttcagatg atgaacactg ataagtcatt   240
tgtcattact ataaattta aaatctgtta ataagatggc ctatagggag gaaaagggg    300 c                                                                    301
```

<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297

```
actgagtttt aactggacgc caagcaggca aggctggaag gttttgctct ctttgtgcta     60
aaggttttga aaaccttgaa ggagaatcat tttgacaaga agtacttaag agtctagaga   120
acaaagangt gaaccagctg aaagctctcg ggggaancatt acatgtgttg ttaggcctgt   180
tccatcattg ggagtgcact ggccatccct caaaatttgt ctgggctggc ctgagtggtc   240
accgcacctc ggccgcgacc acgctaagcc gaattctgca gatatccatc acactggcgg   300
```

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298

```
tatgggttt gtcacccaaa agctgatgct gagaaaggcc tccctggggc cctcccgcg        60
ggcatctgag agacctggtg ttccagtgtt tctggaaatg ggtcccagtg ccgccggctg     120
tgaagctctc agatcaatca cgggaagggc ctggcggtgg tggccacctg gaaccaccct    180
gtcctgtctg tttacatttc actaycaggt tttctctggg cattacnatt tgttccccta    240
caacagtgac ctgtgcattc tgctgtggcc tgctgtgtct gcaggtggct ctcagcgagg    300
t                                                                    301
```

<210> SEQ ID NO 299
<211> LENGTH: 301
<212> TYPE: DNA
<213> ORGANISM: Homo sapien

<400> SEQUENCE: 299

```
gttttgagac ggagtttcac tcttgttgcc cagactggac tgcaatggca gggtctctgc     60
tcactgcacc ctctgcctcc caggttcgag caattctcct gcctcagcct cccaggtagc    120
tgggattgca ggctcacgcc accatacccca gctaattttt ttgtattttt agtagagacg   180
gagtttcgcc atgttggcca gctggtctca actcctgac ctcaagcgac ctgcctgcct    240
cggcctccca aagtgctgga attataggca tgagtcaaca cgcccagcct aaagatattt    300
t                                                                    301
```

<210> SEQ ID NO 300
<211> LENGTH: 301
<212> TYPE: DNA
<213> ORGANISM: Homo sapien

<400> SEQUENCE: 300

```
attcagtttt atttgctgcc ccagtatctg taaccaggag tgccacaaaa tcttgccaga     60
tatgtcccac acccactggg aaaggctccc acctggctac ttcctctatc agctgggtca    120
gctgcattcc acaaggttct cagcctaatg agtttcacta cctgccagtc tcaaaactta    180
gtaaagcaag accatgacat tcccccacgg aaatcagagt ttgccccacc gtcttgttac    240
tataaagcct gcctctaaca gtccttgctt cttcacacca atcccgagcg catcccccat    300
g                                                                    301
```

<210> SEQ ID NO 301
<211> LENGTH: 301
<212> TYPE: DNA
<213> ORGANISM: Homo sapien

<400> SEQUENCE: 301

```
ttaaattttt gagaggataa aaaggacaaa taatctagaa atgtgtcttc ttcagtctgc     60
agaggacccc aggtctccaa gcaaccacat ggtcaagggc atgaataatt aaaagttggt    120
gggaactcac aaagaccctc agagctgaga caccccacaac agtgggagct cacaaagacc   180
ctcagagctg agacacccac aacagtggga gctcacaaag accctcagag ctgagacacc   240
cacaacagca cctcgttcag ctgccacatg tgtgaataag gatgcaatgt ccagaagtgt    300
t                                                                    301
```

<210> SEQ ID NO 302
<211> LENGTH: 301
<212> TYPE: DNA
<213> ORGANISM: Homo sapien

<400> SEQUENCE: 302

```
aggtacacat ttagcttgtg gtaaatgact cacaaaactg attttaaaat caagttaatg      60
tgaattttga aaattactac ttaatcctaa ttcacaataa caatggcatt aaggtttgac     120
ttgagttggt tcttagtatt atttatggta aataggctct taccacttgc aaataactgg     180
ccacatcatt aatgactgac ttcccagtaa ggctctctaa ggggtaagta ggaggatcca     240
caggatttga gatgctaagg ccccagagat cgtttgatcc aaccctctta ttttcagagg     300
g                                                                    301
```

<210> SEQ ID NO 303
<211> LENGTH: 301
<212> TYPE: DNA
<213> ORGANISM: Homo sapien

<400> SEQUENCE: 303

```
aggtaccaac tgtggaaata ggtagaggat cattttttct ttccatatca actaagttgt      60
atattgtttt ttgacagttt aacacatctt cttctgtcag agattctttc acaatagcac     120
tggctaatgg aactaccgct tgcatgttaa aaatggtggt ttgtgaaatg atcataggcc     180
agtaacgggt atgttttctt aactgatctt ttgctcgttc caagggacc tcaagacttc      240
catcgatttt atatctgggg tctagaaaag gagttaatct gttttccctc ataaattcac     300
c                                                                    301
```

<210> SEQ ID NO 304
<211> LENGTH: 301
<212> TYPE: DNA
<213> ORGANISM: Homo sapien

<400> SEQUENCE: 304

```
acatggatgt tattttgcag actgtcaacc tgaatttgta tttgcttgac attgcctaat      60
tattagtttc agtttcagct tacccacttt ttgtctgcaa catgcaraas agacagtgcc     120
cttttttagtg tatcatatca ggaatcatct acattggtt tgtgccatta ctggtgcagt     180
gactttcagc cacttgggta aggtggagtt ggccatatgt ctccactgca aaattactga     240
ttttcctttt gtaattaata agtgtgtgtg tgaagattct ttgagatgag gtatatatct     300
c                                                                    301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag      60
caggggaca gacctggaca gacacgttgt catttgctgc tgtgggtagg aaaatgggcg     120
taaggagga gaaacagata caaatctcc aactcagtat taaggtattc tcatgcctag      180
aatattggta gaaacaagaa tacattcata tggcaaataa ctaaccatgg tggaacaaaa     240
ttctgggatt taagttggat accaangaaa ttgtattaaa agagctgttc atggaataag     300
a                                                                    301
```

<210> SEQ ID NO 306
<211> LENGTH: 8
<212> TYPE: PRT
<213> ORGANISM: Homo sapien

<400> SEQUENCE: 306

Val Leu Gly Trp Val Ala Glu Leu
 1               5

<210> SEQ ID NO 307
<211> LENGTH: 637
<212> TYPE: DNA
<213> ORGANISM: Homo sapien

<400> SEQUENCE: 307

```
acagggratg aagggaaagg gagaggatga ggaagccccc ctgggggattt ggtttggtcc      60
ttgtgatcag gtggtctatg gggcttatcc ctacaaagaa gaatccagaa atagggggcac    120
attgaggaat gatacttgag cccaaagagc attcaatcat tgttttattt gccttmtttt    180
cacaccattg gtgagggagg gattaccacc ctggggttat gaagatggtt gaacacccca    240
cacatagcac cggagatatg agatcaacag tttcttagcc atagagattc acagcccaga    300
gcaggaggac gcttgcacac catgcaggat gacatggggg atgcgctcgg gattggtgtg    360
aagaagcaag gactgttaga ggcaggcttt atagtaacaa gacggtgggg caaactctga    420
tttccgtggg ggaatgtcat ggtcttgctt tactaagttt tgagactggc aggtagtgaa    480
actcattagg ctgagaacct tgtggaatgc acttgaccca sctgatagag gaagtagcca    540
ggtgggagcc tttcccagtg ggtgtgggac atatctggca agattttgtg gcactcctgg    600
ttacagatac tggggcagca aataaaactg aatcttg                             637
```

<210> SEQ ID NO 308
<211> LENGTH: 647
<212> TYPE: DNA
<213> ORGANISM: Homo sapien
<220> FEATURE:
<221> NAME/KEY: misc_feature
<222> LOCATION: (1)...(647)
<223> OTHER INFORMATION: n = A,T,C or G

<400> SEQUENCE: 308

```
acgattttca ttatcatgta aatcgggtca ctcaaggggc caaccacagc tgggagccac      60
tgctcagggg aaggttcata tgggactttc tactgcccaa ggttctatac aggatataaa    120
ggngcctcac agtatagatc tggtagcaaa gaagaagaaa caaacactga tctctttctg    180
ccacccctct gacctttgg aactcctctg acccttaga acaagcctac ctaatatctg      240
ctagagaaaa gaccaacaac ggcctcaaag gatctcttac catgaaggtc tcagctaatt    300
cttggctaag atgtgggttc cacattaggt tctgaatatg gggggaaggg tcaatttgct    360
cattttgtgt gtggataaag tcaggatgcc caggggccag agcaggggggc tgcttgcttt    420
gggaacaatg gctgagcata taaccatagg ttatggggaa caaacaaca tcaaagtcac    480
tgtatcaatt gccatgaaga cttgagggac ctgaatctac cgattcatct taaggcagca    540
ggaccagttt gagtggcaac aatgcagcag cagaatcaat ggaaacaaca gaatgattgc    600
aatgtccttt tttttctcct gcttctgact tgataaaagg ggaccgt                  647
```

<210> SEQ ID NO 309
<211> LENGTH: 460
<212> TYPE: DNA

<213> ORGANISM: Homo sapien

<400> SEQUENCE: 309

```
actttatagt ttaggctgga cattggaaaa aaaaaaagc cagaacaaca tgtgatagat      60
aatatgattg gctgcacact tccagactga tgaatgatga acgtgatgga ctattgtatg     120
gagcacatct tcagcaagag ggggaaatac tcatcatttt tggccagcag ttgtttgatc     180
accaaacatc atgccagaat actcagcaaa ccttcttagc tcttgagaag tcaaagtccg     240
ggggaattta ttcctggcaa ttttaattgg actccttatg tgagagcagc ggctacccag     300
ctggggtggt ggagcgaacc cgtcactagt ggacatgcag tggcagagct cctggtaacc     360
acctagagga atacacaggc acatgtgtga tgccaagcgt gacacctgta gcactcaaat     420
ttgtcttgtt tttgtctttc ggtgtgtaag attcttaagt                           460
```

<210> SEQ ID NO 310
<211> LENGTH: 539
<212> TYPE: DNA
<213> ORGANISM: Homo sapien

<400> SEQUENCE: 310

```
acgggactta tcaaataaag ataggaaaag aagaaaactc aaatattata ggcagaaatg      60
ctaaaggttt taaaatatgt caggattgga agaaggcatg gataaagaac aaagttcagt     120
taggaaagag aaacacagaa ggaagagaca caataaaagt cattatgtat tctgtgagaa     180
gtcagacagt aagatttgtg ggaaatgggt tggtttgttg tatggtatgt attttagcaa     240
taatctttat ggcagagaaa gctaaaatcc tttagcttgc gtgaatgatc acttgctgaa     300
ttcctcaagg taggcatgat gaaggagggt ttagaggaga cacagacaca atgaactgac     360
ctagatagaa agccttagta tactcagcta ggaatagtga ttctgagggc acactgtgac     420
atgattatgt cattacatgt atggtagtga tggggatgat aggaaggaag aacttatggc     480
atattttcac ccccacaaaa gtcagttaaa tattgggaca ctaaccatcc aggtcaaga      539
```

<210> SEQ ID NO 311
<211> LENGTH: 526
<212> TYPE: DNA
<213> ORGANISM: Homo sapien
<220> FEATURE:
<221> NAME/KEY: misc_feature
<222> LOCATION: (1)...(526)
<223> OTHER INFORMATION: n = A,T,C or G

<400> SEQUENCE: 311

```
caaatttgag ccaatgacat agaattttac aaatcaagaa gcttattctg gggccatttc      60
ttttgacgtt ttctctaaac tactaaagag gcattaatga tccataaatt atattatcta     120
catttacagc atttaaaatg tgttcagcat gaaatattag ctacagggga agctaaataa     180
attaaacatg gaataaagat ttgtccttaa atataatcta caagaagact tgatatttg      240
tttttcacaa gtgaagcatt cttataaagt gtcataacct ttttggggaa actatgggaa     300
aaaatgggga aactctgaag ggttttaagt atcttacctg aagctacaga ctccataacc     360
tctctttaca gggagctcct gcagccccta cagaaatgag tggctgagat tcttgattgc     420
acagcaagag cttctcatct aaacccttc ccttttagt atctgtgtat caagtataaa       480
agttctataa actgtagtnt acttatttta atccccaaag cacagt                    526
```

<210> SEQ ID NO 312
<211> LENGTH: 500

```
<212> TYPE: DNA
<213> ORGANISM: Homo sapien
<220> FEATURE:
<221> NAME/KEY: misc_feature
<222> LOCATION: (1)...(500)
<223> OTHER INFORMATION: n = A,T,C or G

<400> SEQUENCE: 312
cctctctctc cccaccccct gactctagag aactgggttt tctcccagta ctccagcaat      60
tcatttctga aagcagttga gccactttat tccaaagtac actgcagatg ttcaaactct     120
ccatttctct ttcccttcca cctgccagtt ttgctgactc tcaacttgtc atgagtgtaa     180
gcattaagga cattatgctt cttcgattct gaagacaggc cctgctcatg gatgactctg     240
gcttcttagg aaaatatttt tcttccaaaa tcagtaggaa atctaaactt atcccctctt     300
tgcagatgtc tagcagcttc agacatttgg ttaagaaccc atgggaaaaa aaaaaatcct     360
tgctaatgtg gtttcctttg taaaccanga ttcttatttg nctggtatag aatatcagct     420
ctgaacgtgt ggtaaagatt tttgtgtttg aatataggag aaatcagttt gctgaaaagt     480
tagtcttaat tatctattgg                                                 500

<210> SEQ ID NO 313
<211> LENGTH: 718
<212> TYPE: DNA
<213> ORGANISM: Homo sapien
<220> FEATURE:
<221> NAME/KEY: misc_feature
<222> LOCATION: (1)...(718)
<223> OTHER INFORMATION: n = A,T,C or G

<400> SEQUENCE: 313
ggagatttgt gtggtttgca gccgagggag accaggaaga tctgcatggt gggaaggacc      60
tgatgataca gaggtgagaa ataagaaagg ctgctgactt taccatctga ggccacacat     120
ctgctgaaat ggagataatt aacatcacta gaaacagcaa gatgacaata taatgtctaa     180
gtagtgacat gtttttgcac atttccagcc cttttaaata tccacacaca caggaagcac     240
aaaaggaagc acagagatcc ctgggagaaa tgcccggccg ccatcttggg tcatcgatga     300
gcctcgccct gtgcctgntc ccgcttgtga gggaaggaca ttagaaaatg aattgatgtg     360
ttccttaaag gatggcagga aaacagatcc tgttgtggat atttatttga acgggattac     420
agatttgaaa tgaagtcaca aagtgagcat taccaatgag aggaaaacag acgagaaaat     480
cttgatggtt cacaagacat gcaacaaaca aaatggaata ctgtgatgac acgagcagcc     540
aactggggag gagataccac ggggcagagg tcaggattct ggccctgctg cctaactgtg     600
cgttatacca atcatttcta tttctaccct caaacaagct gtngaatatc tgacttacgg     660
ttcttntggc ccacatttc atnatccacc ccntcntttt aannttantc caaantgt       718

<210> SEQ ID NO 314
<211> LENGTH: 358
<212> TYPE: DNA
<213> ORGANISM: Homo sapien

<400> SEQUENCE: 314
gtttatttac attacagaaa aaacatcaag acaatgtata ctatttcaaa tatatccata      60
cataatcaaa tatagctgta gtacatgttt tcattggtgt agattaccac aaatgcaagg     120
caacatgtgt agatctcttg tcttattctt ttgtctataa tactgtattg tgtagtccaa     180
gctctcggta gtccagccac tgtgaaacat gctccctta gattaacctc gtggacgctc     240
```

```
ttgttgtatt gctgaactgt agtgccctgt attttgcttc tgtctgtgaa ttctgttgct    300
tctggggcat ttccttgtga tgcagaggac caccacacag atgacagcaa tctgaatt     358
```

<210> SEQ ID NO 315
<211> LENGTH: 341
<212> TYPE: DNA
<213> ORGANISM: Homo sapien

<400> SEQUENCE: 315

```
taccacctcc ccgctggcac tgatgagccg catcaccatg gtcaccagca ccatgaaggc    60
ataggtgatg atgaggacat ggaatgggcc cccaaggatg gtctgtccaa agaagcgagt   120 gaccccatt ctgaagatgt ctggaacctc taccagcagg atgatgatag ccccaatgac    180
agtcaccagc tccccgacca gccggatatc gtccttaggg gtcatgtagg cttcctgaag   240
tagcttctgc tgtaagaggg tgttgtcccg ggggctcgtg cggttattgg tcctgggctt   300 gaggggcgg tagatgcagc acatggtgaa gcagatgatg t                        341
```

<210> SEQ ID NO 316
<211> LENGTH: 151
<212> TYPE: DNA
<213> ORGANISM: Homo sapien

<400> SEQUENCE: 316

```
agactgggca agactcttac gccccacact gcaatttggt cttgttgccg tatccattta    60
tgtgggcctt tctcgagttt ctgattataa acaccactgg agcgatgtgt tgactggact   120
cattcaggga gctctggttg caatattagt t                                   151
```

<210> SEQ ID NO 317
<211> LENGTH: 151
<212> TYPE: DNA
<213> ORGANISM: Homo sapien

<400> SEQUENCE: 317

```
agaactagtg gatcctaatg aaatacctga acatatatt ggcatttatc aatggctcaa     60
atcttcattt atctctggcc ttaaccctgg ctcctgaggc tgcggccagc agatcccagg   120
ccagggctct gttcttgcca cacctgcttg a                                   151
```

<210> SEQ ID NO 318
<211> LENGTH: 151
<212> TYPE: DNA
<213> ORGANISM: Homo sapien

<400> SEQUENCE: 318

```
actggtggga ggcgctgttt agttggctgt tttcagaggg gtctttcgga gggacctcct    60
gctgcaggct ggagtgtctt tattcctggc gggagaccgc acattccact gctgaggctg   120
tgggggcggt ttatcaggca gtgataaaca t                                   151
```

<210> SEQ ID NO 319
<211> LENGTH: 151
<212> TYPE: DNA
<213> ORGANISM: Homo sapien

<400> SEQUENCE: 319

```
aactagtgga tccagagcta taggtacagt gtgatctcag ctttgcaaac acattttcta    60
catagatagt actaggtatt aatagatatg taaagaaaga aatcacacca ttaataatgg   120
taagattggg tttatgtgat tttagtgggt a                                   151
```

<210> SEQ ID NO 320
<211> LENGTH: 150
<212> TYPE: DNA
<213> ORGANISM: Homo sapien

<400> SEQUENCE: 320
aactagtgga tccactagtc cagtgtggtg gaattccatt gtgttggggt tctagatcgc    60
gagcggctgc cctttttttt tttttttttg gggggaatt tttttttttt aatagttatt   120
gagtgttcta cagcttacag taaataccat                                    150

<210> SEQ ID NO 321
<211> LENGTH: 151
<212> TYPE: DNA
<213> ORGANISM: Homo sapien

<400> SEQUENCE: 321
agcaactttg ttttcatcc aggttatttt aggcttagga tttcctctca cactgcagtt    60
tagggtggca ttgtaaccag ctatggcata ggtgttaacc aaaggctgag taaacatggg   120
tgcctctgag aaatcaaagt cttcatacac t                                  151

<210> SEQ ID NO 322
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 322
atccagcatc ttctcctgtt tcttgccttc cttttcttc ttcttasatt ctgcttgagg    60
tttgggcttg gtcagtttgc cacagggctt ggagatggtg acagtcttct ggcattcggc   120
attgtgcagg gctcgcttca nacttccagt t                                  151

<210> SEQ ID NO 323
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 323
tgaggacttg tkttcttttt ctttattttt aatcctctta ckttgtaaat atattgccta    60
nagactcant tactacccag tttgtggttt twtgggagaa atgtaactgg acagttagct   120
gttcaatyaa aaagacactt ancccatgtg g                                  151

<210> SEQ ID NO 324
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 324
acctgtgtgg aatttcagct ttcctcatgc aaaaggattt tgtatccccg gcctacttga    60

| | |
|---|---|
| agaagtggtc agctaaagga atccaggttg ttggttggac tgttaatacc tttgatgaaa | 120 |
| agagttacta cgaatcccat cttggttcca gctatatcac tgacagcatg gtagaagact | 180 |
| gcgaacctca cttctagact ttcacggtgg gacgaaacgg gttcagaaac tgccaggggc | 240 |
| ctcatacagg gatatcaaaa tacccttttgt gctacccagg ccctggggaa tcaggtgact | 300 |
| cacacaaatg caatagttgg tcactgcatt tttacctgaa ccaaagctaa acccggtgtt | 360 |
| gccaccatgc accatggcat gccagagttc aacactgttg ctcttgaaaa ttgggtctga | 420 |
| aaaaacgcac aagagcccct gccctgccct agctgangca c | 461 |

<210> SEQ ID NO 325
<211> LENGTH: 400
<212> TYPE: DNA
<213> ORGANISM: Homo sapien

<400> SEQUENCE: 325

| | |
|---|---|
| acactgtttc catgttatgt ttctacacat tgctacctca gtgctcctgg aaacttagct | 60 |
| tttgatgtct ccaagtagtc caccttcatt taactctttg aaactgtatc atctttgcca | 120 |
| agtaagagtg gtggcctatt tcagctgctt tgacaaaatg actggctcct gacttaacgt | 180 |
| tctataaatg aatgtgctga agcaaagtgc ccatggtggc ggcgaagaag agaaagatgt | 240 |
| gttttgtttt ggactctctg tggtcccttc caatgctgtg ggtttccaac caggggaagg | 300 |
| gtcccttttg cattgccaag tgccataacc atgagcacta cgctaccatg gttctgcctc | 360 |
| ctggccaagc aggctggttt gcaagaatga aatgaatgat | 400 |

<210> SEQ ID NO 326
<211> LENGTH: 1215
<212> TYPE: DNA
<213> ORGANISM: Homo sapien

<400> SEQUENCE: 326

| | |
|---|---|
| ggaggactgc agcccgcact cgcagccctg gcaggcggca ctggtcatgg aaaacgaatt | 60 |
| gttctgctcg ggcgtcctgg tgcatccgca gtgggtgctg tcagccgcac actgtttcca | 120 |
| gaactcctac accatcgggc tgggcctgca cagtcttgag gccgaccaag agccagggag | 180 |
| ccagatggtg gaggccagcc tctccgtacg gcacccagag tacaacagac ccttgctcgc | 240 |
| taacgacctc atgctcatca gttggacga atccgtgtcc gagtctgaca ccatccggag | 300 |
| catcagcatt gcttcgcagt gccctaccgc ggggaactct tgcctcgttt ctggctgggg | 360 |
| tctgctggcg aacggcagaa tgcctaccgt gctgcagtgc gtgaacgtgt cggtggtgtc | 420 |
| tgaggaggtc tgcagtaagc tctatgaccc gctgtaccac cccagcatgt tctgcgccgg | 480 |
| cggagggcaa gaccagaagg actcctgcaa cggtgactct gggggccccc tgatctgcaa | 540 |
| cgggtacttg cagggccttg tgtctttcgg aaaagcccg tgtggccaag ttggcgtgcc | 600 |
| aggtgtctac accaacctct gcaaattcac tgagtggata gagaaaaccg tccaggccag | 660 |
| ttaactctgg ggactgggaa cccatgaaat tgaccccaa atacatcctg cggaaggaat | 720 |
| tcaggaatat ctgttcccag cccctcctcc ctcaggccca ggagtccagg cccccagccc | 780 |
| ctcctccctc aaaccaaggg tacagatccc cagcccctcc tccctcagac ccaggagtcc | 840 |
| agaccccca gcccctcctc cctcagaccc aggagtccag cccctcctcc ctcagaccca | 900 |
| ggagtccaga cccccagcc cctcctccct cagacccagg gtccaggcc ccaacccct | 960 |
| cctccctcag actcagaggt ccaagccccc aaccctcctc tccccagacc cagagctcca | 1020 |
| ggtcccagcc cctcctccct cagacccagc ggtccaatgc cacctagact ctccctgtac | 1080 |

```
acagtgcccc cttgtggcac gttgacccaa ccttaccagt tggtttttca ttttttgtcc    1140
ctttccccta gatccagaaa taaagtctaa gagaagcgca aaaaaaaaaa aaaaaaaaa     1200 aaaaaaaaaa aaaaa                                                     1215
```

<210> SEQ ID NO 327
<211> LENGTH: 220
<212> TYPE: PRT
<213> ORGANISM: Homo sapien

<400> SEQUENCE: 327

```
Glu Asp Cys Ser Pro His Ser Gln Pro Trp Gln Ala Ala Leu Val Met
 1               5                  10                  15

Glu Asn Glu Leu Phe Cys Ser Gly Val Leu Val His Pro Gln Trp Val
            20                  25                  30

Leu Ser Ala Ala His Cys Phe Gln Asn Ser Tyr Thr Ile Gly Leu Gly
        35                  40                  45

Leu His Ser Leu Glu Ala Asp Gln Glu Pro Gly Ser Gln Met Val Glu
    50                  55                  60

Ala Ser Leu Ser Val Arg His Pro Glu Tyr Asn Arg Pro Leu Leu Ala
65                  70                  75                  80

Asn Asp Leu Met Leu Ile Lys Leu Asp Glu Ser Val Ser Glu Ser Asp
                85                  90                  95

Thr Ile Arg Ser Ile Ser Ile Ala Ser Gln Cys Pro Thr Ala Gly Asn
            100                 105                 110

Ser Cys Leu Val Ser Gly Trp Gly Leu Leu Ala Asn Gly Arg Met Pro
        115                 120                 125

Thr Val Leu Gln Cys Val Asn Val Ser Val Val Ser Glu Glu Val Cys
    130                 135                 140

Ser Lys Leu Tyr Asp Pro Leu Tyr His Pro Ser Met Phe Cys Ala Gly
145                 150                 155                 160

Gly Gly Gln Asp Gln Lys Asp Ser Cys Asn Gly Asp Ser Gly Gly Pro
                165                 170                 175

Leu Ile Cys Asn Gly Tyr Leu Gln Gly Leu Val Ser Phe Gly Lys Ala
            180                 185                 190

Pro Cys Gly Gln Val Gly Val Pro Gly Val Tyr Thr Asn Leu Cys Lys
        195                 200                 205

Phe Thr Glu Trp Ile Glu Lys Thr Val Gln Ala Ser
    210                 215                 220
```

<210> SEQ ID NO 328
<211> LENGTH: 234
<212> TYPE: DNA
<213> ORGANISM: Homo sapien

<400> SEQUENCE: 328

```
cgctcgtctc tggtagctgc agccaaatca taaacggcga ggactgcagc ccgcactcgc      60
agccctggca ggcggcactg gtcatggaaa acgaattgtt ctgctcgggc gtcctggtgc     120
atccgcagtg ggtgctgtca gccacacact gtttccagaa ctcctacacc atcgggctgg    180
gcctgcacag tcttgaggcc gaccaagagc cagggagcca gatggtggag gcca          234
```

<210> SEQ ID NO 329
<211> LENGTH: 77
<212> TYPE: PRT
<213> ORGANISM: Homo sapien

```
<400> SEQUENCE: 329

Leu Val Ser Gly Ser Cys Ser Gln Ile Ile Asn Gly Glu Asp Cys Ser
1               5                   10                  15

Pro His Ser Gln Pro Trp Gln Ala Ala Leu Val Met Glu Asn Glu Leu
            20                  25                  30

Phe Cys Ser Gly Val Leu Val His Pro Gln Trp Val Leu Ser Ala Thr
        35                  40                  45

His Cys Phe Gln Asn Ser Tyr Thr Ile Gly Leu Gly Leu His Ser Leu
    50                  55                  60

Glu Ala Asp Gln Glu Pro Gly Ser Gln Met Val Glu Ala
65                  70                  75

<210> SEQ ID NO 330
<211> LENGTH: 70
<212> TYPE: DNA
<213> ORGANISM: Homo sapien

<400> SEQUENCE: 330
cccaacacaa tgcccgatc ccatccctga ctccgccctc aggatcgctc gtctctggta      60
gctgcagcca                                                            70

<210> SEQ ID NO 331
<211> LENGTH: 22
<212> TYPE: PRT
<213> ORGANISM: Homo sapien

<400> SEQUENCE: 331

Gln His Asn Gly Pro Ile Pro Ser Leu Thr Pro Pro Ser Gly Ser Leu
1               5                   10                  15

Val Ser Gly Ser Cys Ser
            20

<210> SEQ ID NO 332
<211> LENGTH: 2507
<212> TYPE: DNA
<213> ORGANISM: Homo sapien

<400> SEQUENCE: 332
tggtgccgct gcagccggca gagatggttg agctcatgtt cccgctgttg ctcctccttc      60
tgcccttcct tctgtatatg gctgcgcccc aaatcaggaa aatgctgtcc agtgggggtgt    120 gtacatcaac tgttcagctt cctgggaaag tagttgtggt cacaggagct aatacaggta    180
tcgggaagga gacagccaaa gagctggctc agagaggagc tcgagtatat ttagcttgcc    240
gggatgtgga aaaggggggaa ttggtggcca agagatcca gaccacgaca gggaaccagc    300
aggtgttggt gcggaaactg gacctgtctg atactaagtc tattcgagct tttgctaagg    360
gcttcttagc tgaggaaaag cacctccacg ttttgatcaa caatgcagga gtgatgatgt    420
gtccgtactc gaagacagca gatggctttg agatgcacat aggagtcaac cacttgggtc    480
acttcctcct aacccatctg ctgctagaga aactaaagga atcagcccca tcaaggatag    540
taaatgtgtc ttccctcgca catcacctgg aaggatccca cttccataac ctgcagggcg    600
agaaattcta caatgcaggc ctggcctact gtcacagcaa gctagccaac atcctcttca    660
cccaggaact ggcccggaga ctaaaaggct ctggcgttac gacgtattct gtacaccctg    720
gcacagtcca atctgaactg gttcggcact catctttcat gagatggatg tggtggcttt    780 tctcctttttt catcaagact cctcagcagg gagcccagac cagcctgcac tgtgccttaa    840
```

```
cagaaggtct tgagattcta agtgggaatc atttcagtga ctgtcatgtg gcatgggtct      900
ctgcccaagc tcgtaatgag actatagcaa ggcggctgtg ggacgtcagt tgtgacctgc      960
tgggcctccc aatagactaa caggcagtgc cagttggacc caagagaaga ctgcagcaga     1020
ctacacagta cttcttgtca aaatgattct ccttcaaggt tttcaaaacc tttagcacaa     1080
agagagcaaa accttccagc cttgcctgct tggtgtccag ttaaaactca gtgtactgcc     1140
agattcgtct aaatgtctgt catgtccaga tttactttgc ttctgttact gccagagtta     1200
ctagagatat cataatagga taagaagacc ctcatatgac ctgcacagct catttttcctt   1260 ctgaaagaaa ctactaccta ggagaatcta agctatagca gggatgattt atgcaaattt     1320
gaactagctt ctttgttcac aattcagttc ctcccaacca accagtcttc acttcaagag     1380
ggccacactg caacctcagc ttaacatgaa taacaaagac tggctcagga gcagggcttg     1440
cccaggcatg gtggatcacc ggaggtcagt agttcaagac cagcctggcc aacatggtga     1500
aaccccacct ctactaaaaa ttgtgtatat cttttgtgtgt cttcctgttt atgtgtgcca    1560
agggagtatt ttcacaaagt tcaaaacagc acaataatc agagatggag caaaccagtg      1620
ccatccagtc tttatgcaaa tgaaatgctg caaagggaag cagattctgt atatgttggt     1680
aactacccac caagagcaca tgggtagcag ggaagaagta aaaaaagaga aggagaatac     1740
tggaagataa tgcacaaaat gaagggacta gttaaggatt aactagccct ttaaggatta    1800
actagttaag gattaatagc aaaagayatt aaatatgcta acatagctat ggaggaattg     1860
agggcaagca cccaggactg atgaggtctt aacaaaaacc agtgtggcaa aaaaaaaaa     1920 aaaaaaaaaa aaaatcccta aaaacaaaca aacaaaaaaa acaattcttc attcagaaaa     1980
attatcttag ggactgatat tggtaattat ggtcaattta ataatatttt ggggcatttc    2040
cttacattgt cttgacaaga ttaaaatgtc tgtgccaaaa ttttgtattt tatttggaga     2100
cttcttatca aaagtaatgc tgccaaagga agtctaagga attagtagtg ttcccatcac     2160
ttgtttggag tgtgctattc taaaagattt tgatttcctg gaatgacaat tatattttaa     2220 cttttggtggg ggaaagagtt ataggaccac agtcttcact tctgatactt gtaaattaat   2280 ctttattgc acttgttttg accattaagc tatatgttta gaaatggtca ttttacggaa      2340
aaattagaaa aattctgata atagtgcaga ataaatgaat taatgtttta cttaattttat   2400 attgaactgt caatgacaaa taaaaattct ttttgattat tttttgtttt catttaccag    2460
aataaaaacg taagaattaa aagtttgatt acaaaaaaaa aaaaaaa                  2507
```

<210> SEQ ID NO 333
<211> LENGTH: 3030
<212> TYPE: DNA
<213> ORGANISM: Homo sapien

<400> SEQUENCE: 333

```
gcaggcgact tgcgagctgg gagcgattta aaacgctttg gattccccccg gcctgggtgg     60 ggagagcgag ctgggtgccc cctagattcc ccgcccccgc acctcatgag ccgaccctcg    120
gctccatgga gcccggcaat tatgccacct tggatggagc caaggatatc gaaggcttgc    180
tgggagcggg agggggcgg aatctggtcg cccactcccc tctgaccagc cacccagcgg     240
cgcctacgct gatgcctgct gtcaactatg ccccccttgga tctgccaggc tcggcggagc   300
cgccaaagca atgccaccca tgccctgggg tgccccaggg acgtcccca gctcccgtgc     360 cttatggtta cttttggaggc gggtactact cctgccgagt gtccccggagc tcgctgaaac   420 cctgtgccca ggcagccacc ctggccgcgt acccccgcgga gactcccacg gccggggaag    480
```

-continued

```
agtaccccag ycgccccact gagtttgcct tctatccggg atatccggga acctaccagc      540
ctatggccag ttacctggac gtgtctgtgg tgcagactct gggtgctcct ggagaaccgc      600
gacatgactc cctgttgcct gtggacagtt accagtcttg ggctctcgct ggtggctgga      660
acagccagat gtgttgccag ggagaacaga acccaccagg tccctttgg aaggcagcat       720 ttgcagactc cagcgggcag caccctcctg acgcctgcgc ctttcgtcgc ggccgcaaga      780
aacgcattcc gtacagcaag gggcagttgc gggagctgga gcgggagtat gcggctaaca      840
agttcatcac caaggacaag aggcgcaaga tctcggcagc caccagcctc tcggagcgcc      900
agattaccat ctggtttcag aaccgccggg tcaaagagaa aaggttctc gccaaggtga       960 agaacagcgc tacccttaa gagatctcct tgcctgggtg ggaggagcga aagtgggggt      1020
gtcctgggga gaccaggaac ctgccaagcc caggctgggg ccaaggactc tgctgagagg     1080
cccctagaga caacacccct tcccaggccac tggctgctgg actgttcctc aggagcggcc    1140
tgggtaccca gtatgtgcag ggagacggaa ccccatgtga cagcccactc caccagggtt     1200
cccaaagaac ctggcccagt cataatcatt catcctgaca gtggcaataa tcacgataac     1260
cagtactagc tgccatgatc gttagcctca tattttctat ctagagctct gtagagcact    1320
ttagaaaccg ctttcatgaa ttgagctaat tatgaataaa tttggaaggc gatccctttg    1380
cagggaagct ttctctcaga ccccctcca ttacacctct caccctggta acagcaggaa     1440
gactgaggag aggggaacgg gcagattcgt tgtgtggctg tgatgtccgt ttagcatttt    1500
tctcagctga cagctgggta ggtggacaat tgtagaggct gtctcttcct ccctccttgt    1560
ccaccccata gggtgtaccc actggtcttg gaagcaccca tccttaatac gatgattttt    1620
ctgtcgtgtg aaaatgaagc cagcaggctg cccctagtca gtccttcctt ccagagaaaa    1680
agagatttga gaaagtgcct gggtaattca ccattaattt cctcccccaa actctctgag    1740
tcttccctta atatttctgg tggttctgac caaagcaggt catggtttgt tgagcatttg    1800
ggatcccagt gaagtagatg tttgtagcct tgcatactta gcccttccca ggcacaaacg    1860
gagtggcaga gtggtgccaa ccctgttttc ccagtccacg tagacagatt cacagtgcgg    1920
aattctggaa gctggagaca gacgggctct ttgcagagcc gggactctga gagggacatg    1980
agggcctctg cctctgtgtt cattctctga tgtcctgtac ctgggctcag tgcccggtgg    2040
gactcatctc ctggccgcgc agcaaagcca gcgggttcgt gctggtcctt cctgcaccttt   2100 aggctggggg tgggggcct gccggcgcat tctccacgat tgagcgcaca ggcctgaagt     2160
ctggacaacc cgcagaaccg aagctccgag cagcgggtcg gtggcgagta gtgggtcgg     2220 tggcgagcag ttggtggtgg gccgcggccg ccactacctc gaggacattt ccctcccgga    2280
gccagctctc ctagaaaccc cgcggcggcc gccgcagcca agtgtttatg gcccgcggtc    2340
gggtgggatc ctagccctgt ctcctctcct gggaaggagt gagggtggga cgtgacttag    2400
acacctacaa atctatttac caaagaggag cccgggactg agggaaaagg ccaaagagtg    2460
tgagtgcatg cggactgggg gttcagggga agaggacgag gaggaggaag atgaggtcga    2520
tttcctgatt taaaaaatcg tccaagcccc gtggtccagc ttaaggtcct cggttacatg    2580
cgccgctcag agcaggtcac tttctgcctt ccacgtcctc cttcaaggaa gcccatgtg    2640 ggtagctttc aatatcgcag gttcttactc ctctgcctct ataagctcaa acccaccaac    2700
gatcgggcaa gtaaaccccc tccctcgccg acttcggaac tggcgagagt tcagcgcaga    2760
tgggcctgtg gggagggggc aagatagatg aggggagcg gcatggtgcg gggtgacccc    2820
```

-continued

| | |
|---|---|
| ttggagagag gaaaaaggcc acaagaggg ctgccaccgc cactaacgga gatggccctg | 2880 |
| gtagagacct ttgggggtct ggaacctctg gactccccat gctctaactc ccacactctg | 2940 |
| ctatcagaaa cttaaacttg aggattttct ctgttttca ctcgcaataa aytcagagca | 3000 |
| aacaaaaaaa aaaaaaaaaa aaaactcgag | 3030 |

<210> SEQ ID NO 334
<211> LENGTH: 2417
<212> TYPE: DNA
<213> ORGANISM: Homo sapien

<400> SEQUENCE: 334

| | |
|---|---|
| ggcggccgct ctagagctag tgggatcccc cgggctgcac gaattcggca cgagtgagtt | 60 |
| ggagttttac ctgtattgtt ttaatttcaa caagcctgag gactagccac aaatgtaccc | 120 |
| agtttacaaa tgaggaaaca ggtgcaaaaa ggttgttacc tgtcaaaggt cgtatgtggc | 180 |
| agagccaaga tttgagccca gttatgtctg atgaacttag cctatgctct ttaaacttct | 240 |
| gaatgctgac cattgaggat atctaaactt agatcaattg cattttccct ccaagactat | 300 |
| ttacttatca atacaataat accaccttta ccaatctatt gttttgatac gagactcaaa | 360 |
| tatgccagat atatgtaaaa gcaacctaca agctctctaa tcatgctcac ctaaaagatt | 420 |
| cccgggatct aataggctca agaaacttc ttctagaaat ataaagaga aaattggatt | 480 |
| atgcaaaaat tcattattaa ttttttttcat ccatccttta attcagcaaa catttatctg | 540 |
| ttgttgactt tatgcagtat ggcctttaa ggattggggg acaggtgaag aacggggtgc | 600 |
| cagaatgcat cctcctacta atgaggtcag tacacatttg cattttaaaa tgccctgtcc | 660 |
| agctgggcat ggtggatcat gcctgtaatc tcaacattgg aaggccaagg caggaggatt | 720 |
| gcttcagccc aggagttcaa gaccagcctg gcaacatag aaagacccca tctctcaatc | 780 |
| aatcaatcaa tgccctgtct ttgaaaataa aactctttaa gaaaggttta atgggcaggg | 840 |
| tgtggtagct catgcctata atacagcact ttgggaggct gaggcaggag gatcacttta | 900 |
| gcccagaagt tcaagaccag cctgggcaac aagtgacacc tcatctcaat tttttaataa | 960 |
| aatgaataca tacataagga aagataaaaa gaaaagtttta atgaaagaat acagtataaa | 1020 |
| acaaatctct tggacctaaa agtatttttg ttcaagccaa atattgtgaa tcacctctct | 1080 |
| gtgttgagga tacagaatat ctaagcccag gaaactgagc agaaagttca tgtactaact | 1140 |
| aatcaacccg aggcaaggca aaatgagac taactaatca atccgaggca aggggcaaat | 1200 |
| tagacggaac ctgactctgg tctattaagc gacaactttc cctctgttgt attttctttt | 1260 |
| tattcaatgt aaaaggataa aaactctcta aaactaaaaa caatgtttgt caggagttac | 1320 |
| aaaccatgac caactaatta tggggaatca taaaatatga ctgtatgaga tcttgatggt | 1380 |
| ttacaaagtg tacccactgt taatcacttt aaacattaat gaacttaaaa atgaatttac | 1440 |
| ggagattgga atgtttcttt cctgttgtat tagttggctc aggctgccat aacaaaatac | 1500 |
| cacagactgg gaggcttaag taacagaaat tcatttctca cagttctggg ggctggaagt | 1560 |
| ccacgatcaa ggtgcaggaa aggcaggctt cattctgagg cccctctctt ggctcacatg | 1620 |
| tggccaccct cccactgcgt gctcacatga cctctttgtg ctcctggaaa gagggtgtgg | 1680 |
| gggacagagg gaaagagaag gagagggaac tctctggtgt ctcgtctttc aaggacccta | 1740 |
| acctgggcca ctttgcccca ggcactgtgg ggtggggggt tgtggctgct ctgctctgag | 1800 |
| tggccaagat aaagcaacag aaaaatgtcc aaagctgtgc agcaaagaca agccaccgaa | 1860 |
| cagggatctg ctcatcagtg tggggacctc caagtcggcc accctggagg caagccccca | 1920 |

```
cagagcccat gcaaggtggc agcagcagaa aagggaatt gtccctgtcc ttggcacatt      1980
cctcaccgac ctggtgatgc tggacactgc gatgaatggt aatgtggatg agaatatgat      2040 ggactccag aaaaggagac ccagctgctc aggtggctgc aaatcattac agccttcatc      2100
ctggggagga actgggggcc tggttctggg tcagagagca gcccagtgag ggtgagagct      2160
acagcctgtc ctgccagctg atccccagt cccggtcaac cagtaatcaa ggctgagcag      2220
atcaggcttc ccgagctgg tcttgggaag ccagccctgg ggtgagttgg ctcctgctgt      2280
ggtactgaga caatattgtc ataaattcaa tgcgcccttg tatccctttt tcttttttat      2340
ctgtctacat ctataatcac tatgcatact agtctttgtt agtgtttcta ttcmacttaa      2400
tagagatatg ttatact                                                    2417

<210> SEQ ID NO 335
<211> LENGTH: 2984
<212> TYPE: DNA
<213> ORGANISM: Homo sapien

<400> SEQUENCE: 335
atccctcctt ccccactctc ctttccagaa ggcacttggg gtcttatctg ttggactctg        60
aaaacacttc aggcgcccct tccaaggcttc cccaaacccc taagcagccg cagaagcgct      120
cccgagctgc cttctcccac actcaggtga tcgagttgga gaggaagttc agccatcaga      180
agtacctgtc ggcccctgaa cgggcccacc tggccaagaa cctcaagctc acggagaccc      240
aagtgaagat atggttccag aacagacgct ataagactaa gcgaaagcag ctctcctcgg      300
agctgggaga cttggagaag cactcctctt tgccggccct gaaagaggag gccttctccc      360
gggcctccct ggtctccgtg tataacagct atccttacta cccatacctg tactgcgtgg      420
gcagctggag cccagctttt tggtaatgcc agctcaggtg acaaccatta tgatcaaaaa      480
ctgccttccc cagggtgtct ctatgaaaag cacaagggc caaggtcagg gagcaagagg      540
tgtgcacacc aaagctattg gagatttgcg tggaaatctc asattcttca ctggtgagac      600
aatgaaacaa cagagacagt gaaagttta atacctaagt cattccccca gtgcatactg      660
taggtcattt ttttttgcttc tggctacctg tttgaagggg agagagggaa atcaagtgg      720 tattttccag cactttgtat gattttggat gagctgtaca cccaaggatt ctgttctgca      780
actccatcct cctgtgtcac tgaatatcaa ctctgaaaga gcaaacctaa caggagaaag      840
gacaaccagg atgaggatgt caccaactga attaaactta agtccagaag cctcctgttg      900
gccttggaat atggccaagg ctctctctgt ccctgtaaaa gagagggca aatagagagt      960 ctccaagaga acgccctcat gctcagcaca tatttgcatg ggagggggag atgggtggga     1020
ggagatgaaa atatcagctt ttcttattcc tttttattcc ttttaaaatg gtatgccaac     1080
ttaagtattt acagggtggc ccaaatagaa caagatgcac tcgctgtgat tttaagacaa     1140
gctgtataaa cagaactcca ctgcaagagg gggggccggg ccaggagaat ctccgcttgt     1200
ccaagacagg ggcctaagga gggtctccac actgctgcta ggggctgttg catttttta      1260 ttagtagaaa gtggaaaggc ctcttctcaa cttttttccc ttgggctgga gaatttagaa     1320
tcagaagttt cctggagttt tcaggctatc atatatactg tatcctgaaa ggcaacataa     1380
ttcttccttc cctccttta aaattttgtg ttccttttg cagcaattac tcactaaagg      1440
gcttcatttt agtccagatt tttagtctgg ctgcacctaa cttatgcctc gcttatttag     1500
cccgagatct ggtctttttt tttttttttt tttttccgtc tccccaaagc tttatctgtc     1560
```

```
ttgactttt   aaaaaagttt   ggggcagat    tctgaattgg   ctaaaagaca   tgcatttta     1620 aaactagcaa   ctcttatttc   tttcctttaa   aaatacatag   cattaaatcc   caatccatat    1680
ttaaagacct   gacagcttga   gaaggtcact   actgcattta   taggaccttc   tggtggttct    1740
gctgttacgt   ttgaagtctg   acaatccttg   agaatctttg   catgcagagg   aggtaagagg    1800
tattggattt   tcacagagga   agaacacagc   gcagaatgaa   gggccaggct   tactgagctg    1860
tccagtggag   ggctcatggg   tgggacatgg   aaagaaggc    agcctaggcc   ctggggagcc    1920
cagtccactg   agcaagcaag   ggactgagtg   agccttttgc   aggaaaaggc   taagaaaaag    1980
gaaaaccatt   ctaaaacaca   acaagaaact   gtccaaatgc   tttgggaact   gtgtttattg    2040
cctataatgg   gtccccaaaa   tgggtaacct   agacttcaga   gagaatgagc   agagagcaaa    2100
ggagaaatct   ggctgtcctt   ccatttcat    tctgttatct   caggtgagct   ggtagagggg    2160
agacattaga   aaaaaatgaa   acaacaaaac   aattactaat   gaggtacgct   gaggcctggg    2220
agtctcttga   ctccactact   taattccgtt   tagtgagaaa   cctttcaatt   ttcttttatt    2280
agaagggcca   gcttactgtt   ggtggcaaaa   ttgccaacat   aagttaatag   aaagttggcc    2340
aatttcaccc   cattttctgt   ggtttgggct   ccacattgca   atgttcaatg   ccacgtgctg    2400
ctgacaccga   ccggagtact   agccagcaca   aaaggcaggg   tagcctgaat   tgctttctgc    2460
tctttacatt   tcttttaaaa   taagcattta   gtgctcagtc   cctactgagt   actctttctc    2520
tcccctcctc   tgaatttaat   tctttcaact   tgcaatttgc   aaggattaca   catttcactg    2580
tgatgtatat   tgtgttgcaa   aaaaaaaaa   aagtgtctt    gtttaaaatt   acttggtttg    2640
tgaatccatc   ttgctttttc   cccattggaa   ctagtcatta   acccatctct   gaactggtag    2700
aaaaacatct   gaagagctag   tctatcagca   tctgacaggt   gaattggatg   gttctcagaa    2760
ccatttcacc   cagacagcct   gtttctatcc   tgtttaataa   attagtttgg   gttctctaca    2820
tgcataacaa   accctgctcc   aatctgtcac   ataaagtct    gtgacttgaa   gtttagtcag    2880
cacccccacc   aaactttatt   tttctatgtg   ttttttgcaa   catatgagtg   ttttgaaaat    2940
aaagtaccca   tgtctttatt   agaaaaaaaa   aaaaaaaaa    aaaa                       2984
```

<210> SEQ ID NO 336
<211> LENGTH: 147
<212> TYPE: PRT
<213> ORGANISM: Homo sapien

<400> SEQUENCE: 336

```
Pro Ser Phe Pro Thr Leu Leu Ser Arg Arg His Leu Gly Ser Tyr Leu
  1               5                  10                  15

Leu Asp Ser Glu Asn Thr Ser Gly Ala Leu Pro Arg Leu Pro Gln Thr
             20                  25                  30

Pro Lys Gln Pro Gln Lys Arg Ser Arg Ala Ala Phe Ser His Thr Gln
         35                  40                  45

Val Ile Glu Leu Glu Arg Lys Phe Ser His Gln Lys Tyr Leu Ser Ala
     50                  55                  60

Pro Glu Arg Ala His Leu Ala Lys Asn Leu Lys Leu Thr Glu Thr Gln
 65                  70                  75                  80

Val Lys Ile Trp Phe Gln Asn Arg Arg Tyr Lys Thr Lys Arg Lys Gln
                 85                  90                  95

Leu Ser Ser Glu Leu Gly Asp Leu Glu Lys His Ser Ser Leu Pro Ala
            100                 105                 110

Leu Lys Glu Glu Ala Phe Ser Arg Ala Ser Leu Val Ser Val Tyr Asn
        115                 120                 125
```

```
Ser Tyr Pro Tyr Tyr Pro Tyr Leu Tyr Cys Val Gly Ser Trp Ser Pro
    130                 135                 140
Ala Phe Trp
145

<210> SEQ ID NO 337
<211> LENGTH: 9
<212> TYPE: PRT
<213> ORGANISM: Homo sapien

<400> SEQUENCE: 337

Ala Leu Thr Gly Phe Thr Phe Ser Ala
 1               5

<210> SEQ ID NO 338
<211> LENGTH: 9
<212> TYPE: PRT
<213> ORGANISM: Homo sapien

<400> SEQUENCE: 338

Leu Leu Ala Asn Asp Leu Met Leu Ile
 1               5
```

COMPOUNDS FOR IMMUNOTHERAPY OF PROSTATE CANCER AND METHODS FOR THEIR USE

CROSS REFERENCE TO RELATED APPLICATIONS

This application is a Divisional of pending U.S. patent application Ser. No. 09/232,149, filed Jan. 15, 1999 now U.S. Pat. No. 6,465,611, which is a continuation-in-part of U.S. patent application Ser. No. 09/159,812, filed Sep. 23, 1998, which is a continuation-in-part of U.S. patent application Ser. No. 09/115,453, filed Jul. 14, 1998, which is a continuation-in-part of U.S. patent application Ser. No. 09/030,607, filed Feb. 25, 1998 now U.S. Pat. No. 6,262,245, which is a continuation-in-part of U.S. patent application Ser. No. 09/020,956, filed Feb. 9, 1990 now U.S. Pat. No. 6,261,502, which is a continuation-in-part of U.S. patent application Ser. No. 08/904,804, filed Aug. 1, 1997 now abandoned, which is a continuation-in-part of U.S. patent application Ser. No. 08/806,009, filed Feb. 25, 1997 now abandoned.

TECHNICAL FIELD

The present invention relates generally to compositions and methods for the treatment of prostate cancer. The invention is more particularly related to polypeptides comprising at least a portion of a prostate tumor protein and to polynucleotide molecules encoding such polypeptides. Such polypeptides may be used in vaccines and pharmaceutical compositions for treatment of prostate cancer.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

Accordingly, there remains a need in the art for improved vaccines and treatment methods for,prostate cancer. The present invention fulfills these needs and further provides other related advantages.

SUMMARY OF THE INVENTION

The present invention provides compounds and methods for immunotherapy of prostate cancer. In one aspect, isolated polypeptides are provided comprising at least an immunogenic portion of a prostate tumor protein or a variant thereof that differs only in one or more substitutions, deletions, additions and/or insertions, such that the ability of the variant to react with protein-specific antisera is not substantially diminished. Within certain embodiments, the prostate tumor protein comprises an amino acid sequence encoded by a polynucleotide sequence selected from the group consisting of SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, and 334, and complements of such polynucleotides.

In related aspects, isolated polynucleotides encoding the above polypeptides or portions thereof are provided. In specific embodiments, such polynucleotides may comprise a sequence provided in SEQ ID NO: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334. The present invention further provides expression vectors comprising the above polynucleotides and host cells transformed or transfected with such expression vectors. In preferred embodiments, the host cells are selected from the group consisting of $E.\ coli$, yeast and mammalian cells.

In another aspect, the present invention provides fusion proteins comprising at least one polypeptide as described above, in combination with a second polypeptide as described above and/or a known prostate tumor antigen. Polynucleotides encoding such fusion proteins are further provided.

The present invention also provides pharmaceutical compositions comprising one or more of the above polypeptides, or a polynucleotide molecule encoding such polypeptides, and a physiologically acceptable carrier, together with vaccines comprising one or more of such polypeptide or polynucleotide molecules in combination with a non-specific immune response enhancer.

Within other aspects, the present invention provides pharmaceutical compositions comprising (a) an antibody that specifically binds to a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334; and (ii) complements of the foregoing polynucleotide sequences; and (b) a physiologically acceptable carrier. Vaccines are also provided, comprising one or more such antibodies in combination with a non-specific immune response enhancer.

Within other aspects, the present invention provides pharmaceutical compositions comprising (a) a T cell that specifically reacts with a prostate tumor protein that comprises an amino acid sequence that is encoded by a polynucleotide sequence selected from the group consisting of (i) nucleotide sequences recited in any one of SEQ ID NOS: 2, 3, 8–29, 41–45, 47–52, 54–65, 70, 73–74, 79, 81, 87, 90, 92, 93, 97, 103, 104, 107, 109–111, 115–160, 171, 173–175, 177, 181, 188, 191, 193, 194, 198, 203, 204, 207, 209, 220, 222–225, 227–305, 307–315, 326, 328, 330, 332, or 334; and (ii) complements of the foregoing polynucleotide sequences; and (b) a physiologically acceptable carrier. Vaccines are also provided, comprising one or more such T cells in combination with a non-specific immune response enhancer.

In yet a further aspect, methods for the treatment of prostate cancer in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally provides methods for the treatment of prostate cancer that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells and macrophages. Compositions for the treatment of prostate cancer comprising T cells or antigen presenting cells that have been incubated with a polypeptide or polynucleotide of the present invention are also provided.

In yet another aspect, methods are provided for inhibiting the development of prostate cancer in a patient, comprising administering an effective amount of at least one of the above pharmaceutical compositions and/or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

In FIG. 2A, data is presented for fibroblasts pulsed with the P2S-12 peptide, as compared to fibroblasts pulsed with a control E75 peptide. In FIG. 2B, data is presented for fibroblasts expressing P506, as compared to fibroblasts expressing HER-2/neu.

DETAILED DESCRIPTION OF THE INVENTION

Figure 1:
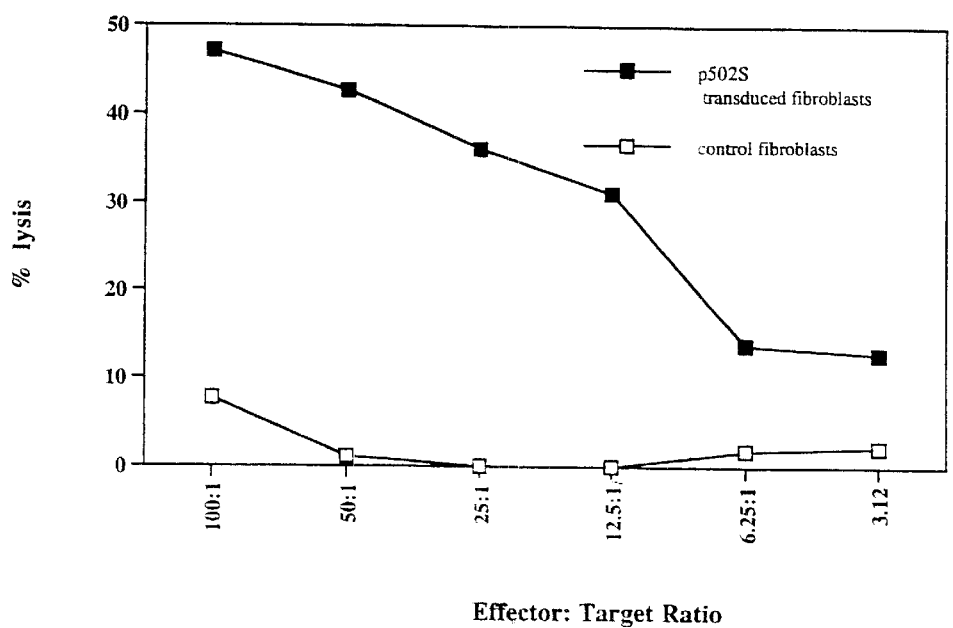
FIG. 1 is a graph illustrating the ability of T cells to kill fibroblasts expressing the representative prostate tumor polypeptide P502S, as compared to control fibroblasts. The % lysis is shown at a series of effector:target ratios, as indicated.

As noted above, the present invention is generally directed to compositions and methods for the therapy of cancer, such as prostate cancer. The compositions described herein may include one or more prostate tumor polypeptides, nucleic acid sequences encoding such polypeptides, binding agents such as antibodies that bind to a polypeptide and/or immune system cells (e.g., T cells). Prostate tumor polypeptides of the present invention generally comprise at least a portion of a prostate tumor protein or a variant thereof, such that the therapeutic, antigenic and/or immunogenic properties of the polypeptide are not substantially diminished relative to the native prostate tumor protein. A "prostate tumor protein" is a protein that is overexpressed (ie., mRNA and/or protein is present at a level that is at least two fold higher) in prostate tumor tissue, relative to normal prostate tissue and/or relative to other tissues (e.g., brain, heart, kidney, liver, lung, pancreas, ovary, placenta, skeletal muscle, spleen and/or thymus). Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a polypeptide as described above. T cells that may be employed within such compositions are generally T cells that are specific for a polypeptide as described above.

The present invention is based on the discovery of previously unknown human prostate tumor proteins. Partial sequences of polynucleotides encoding specific prostate tumor proteins (or complementary to such coding sequences) are provided in SEQ ID NOs:2, 3, 8–29, 4145, 47–52, 54–65, 70, 73–74, 79, 81, 87, 90, 92, 93, 97, 103, 104, 107, 109–111, 111–160, 181, 188, 191, 193, 194, 198, 203, 204, 207–228, 229–305, 307–315, 326, 328, 330, 332, and 334.

Prostate Tumor Polynucleotide

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

Any polynucleotide that encodes a prostate tumor protein or a portion or other variant thereof as described herein is encompassed by the present invention. Preferred polynucleotides comprise at least 10 consecutive nucleotides, and preferably at least 30 consecutive nucleotides, that encode a portion of a prostate tumor protein. More preferably, a polynucleotide encodes an immunogenic portion of a prostate tumor protein. Polynucleotides complementary to any such sequences are also encompassed by the present invention.

Polynucleotides may comprise a native sequence (i.e., an endogenous sequence that encodes a prostate tumor protein or a portion thereof) or may comprise a variant of such a sequence. Polynucleotide variants may contain one or more substitutions, additions, deletions and/or insertions such that the therapeutic, antigenic and/or immunogenic properties are not substantially diminished, relative to a native prostate tumor protein. Such modifications may be readily introduced using standard mutagenesis techniques, such as oligonucleotide directed site-specific mutagenesis as taught, for example, by Adelman et al. (*DNA*, 2:183, 1983). Preferably, the antigenicity or immunogenicity of a polypeptide variant is not substantially diminished. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate tumor protein or a portion thereof. The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native prostate tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2X, 0.5X and 0.2×SSC containing 0.1% SDS).

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, more preferably 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M.O. (1978) A model of evolutionary change in proteins—Matrices for detecting distant relationships. In Dayhoff, M.O. (ed.) Atlas of Protein Sequence and Structure, National Biomedical Resarch Foundaiton, Washington D.C. Vol. 5, Suppl. 3, pp 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer CABIOS 5:151–153; Myers, E. W. and Muller W. (1988) Optimal alignments in linear space CABIOS 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprises additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

Polynucleotides may be prepared using any of a variety of techniques. For example, a polynucleotide may be identified, as described in more detail below, using a PCR-based subtraction protocol Alternatively, polypeptides may be amplified via polymerase chain reaction (PCR) from cDNA prepared from prostate tumor cells. For this approach, sequence-specific primers may be designed based on the sequences provided herein, and may be purchased or synthesized.

An amplified portion may be used to isolate a full length gene from a suitable library (e.g., a prostate tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology*, Stockton Press, N.Y., 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3'end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g. NCBI BLAST searches), and such ESTs may be used to generate a contiguous full length sequence.

Certain nucleic acid sequences of cDNA molecules encoding portions of prostate tumor proteins are provided in SEQ ID NOS: 1–107, 109–111, 115–171, 173–175, 177, 179–228, 229–305, 307–326, 328, 330, and 332–335. The polynucleotides recited herein, as well as full length polynucleotides comprising such sequences, other portions of such full length polynucleotides, and sequences complementary to all or a portion of such full length molecules, are specifically encompassed by the present invention.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a prostate tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (ie., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a prostate tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence or a complementary sequence may also be designed as a probe or primer to detect gene expression. Probes may be labeled by a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length. Any polynucleotide may be further modified to increase stability in vivo. Possible modifications include, but are not limited to, the addition of flanking sequences at the 5' and/or 3' ends; the use of phosphorothioate or 2' β-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating polynucleotides into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Prostate Tumor Polypeptides

Within the context of the present invention, polypeptides may comprise at least a portion of a prostate tumor protein or a variant thereof, as described herein. As noted above, a "prostate tumor protein" is a protein that is overexpressed by prostate tumor cells, relative to normal prostate cells and/or other tissues such as brain, heart, kidney, liver, lung, pancreas, ovary, placenta, skeletal muscle, spleen and/or thymus. Such polypeptides should comprise a portion of a prostate tumor protein such that the therapeutic, antigenic and/or immunogenic properties of the polypeptide are not substantially diminished, relative to the full length protein. Within certain preferred embodiments, a polypeptide comprises an immunogenic portion of a native prostate tumor protein (ie., the immunogenic properties of the polypeptide are not substantially diminished). As used herein, the term "polypeptide" encompasses amino acid chains of any length, including full length proteins, wherein the amino acid residues are linked by covalent peptide bonds. In addition to a portion of a prostate tumor protein, additional sequences derived from the native protein and/or heterologous sequences may be present, and such sequences may (but need not) possess further immunogenic or antigenic properties.

An "immunogenic portion," as used herein is a portion of an antigen that is recognized (i e., specifically bound) by a B-cell and/or T-cell surface antigen receptor. Such immunogenic portions generally comprise at least 5 amino acid residues, more preferably at least 10, and still more preferably at least 20 amino acid residues of a prostate tumor protein or a variant thereof. Immunogenic portions of prostate tumor proteins provided herein may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (ie., they react with the antigen in an ELISA or other immunoassay, and do not react detectably with unrelated proteins). Such antisera and antibodies may be prepared as described herein, and using well known techniques. An immunogenic portion of a native prostate tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Alternatively, an immunogenic portion may react within such assays at a level that is diminished by less than 50%, and preferably less than 20%, relative to the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a polypeptide may comprise a variant of a native prostate tumor protein. A polypeptide "variant," as used herein, is a polypeptide that differs from a native prostate tumor protein in one or more substitutions, deletions, additions and/or insertions, such that the therapeutic, antigenic and/or immunogenic properties are not substantially diminished. Preferably, the immunogenic properties are not substantially diminished. In other words, the ability of a variant to react with antigen-specific antisera may be enhanced or unchanged, relative to the native antigen, or may be diminished by less than 50%, and preferably less than 20%, relative to the native antigen. Polypeptide variants preferably exhibit at least about 70%, more preferably at least about 90% and most preferably at least about 95% identity to polypeptides encoded by polynucleotides specifically recited herein. Identity may be determined by comparing sequences using computer algorithms well known to those of skill in the art, such as Megalign, using default parameters. For prostate tumor polypeptides with immunoreactive properties, variants may generally be identified by modifying one of the above polypeptide sequences and evaluating the reactivity of the modified polypeptide with antigen-specific antibodies or antisera as described herein. For prostate tumor polypeptides useful for the generation of diagnostic binding agents, a variant may be identified by evaluating a modified polypeptide for the ability to generate antibodies that detect the presence or absence of prostate cancer. Such modified sequences may be prepared and tested using, for example, the representative procedures described herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants containing substitutions may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by polynucleotide sequences as described above may be readily prepared from the polynucleotide sequences using any of a variety of expression vectors known to those of ordinary skill in the art Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli*, yeast or a mammalian cell line, such as CHO cells. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known prostate tumor antigen, or a variant of such an antigen. A fusion protein generally comprises at least one of the above immunogenic portions and one or more additional immunogenic prostate tumor sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component polypeptides.

Fusion proteins may generally be prepared using standard techniques. For example, a fusion protein may be prepared recombinantly. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence may be incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the polynucleotide sequence encoding the first polypeptides. Similarly, stop codons required to end translation and transcription termination signals are only present 3' to the polynucleotide sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91, 1997).

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a prostate tumor protein. As used herein, an agent is said to "specifically bind" to a prostate tumor protein if it reacts at a detectable level (within, for example, an ELISA) with a prostate tumor protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents are further capable of detecting metastatic prostate tumors and differentiating between patients with and without prostate cancer, using a representative assay provided herein. In other words, antibodies or other binding agents that bind to a prostate tumor protein will generate a signal indicating the presence of prostate cancer in at least about 20% of patients with the disease, and will generate a negative signal indicating the absence of the disease in at least about 90% of individuals without the cancer. To determine whether a binding agent satisfies this requirement, biological samples (eg., blood, blood-associated tumor cells, sera, urine, biopsies and/or prostate secretions) from patients with and without prostate cancer (as determined using standard clinical tests), may be assayed as described herein for the presence of polypeptides or polynucleotides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

If an immunogenic portion is employed, the resulting antibody should indicate the presence of prostate cancer in substantially all (ie., at least 80%, and preferably at least 90%) of the patients for which prostate cancer would be indicated using an antibody raised against the full length antigen. The antibody should also indicate the absence of prostate cancer in substantially all of those samples that would be negative when tested with an antibody raised against the full length antigen. The representative assays provided herein, such as the two-antibody sandwich assay, may generally be employed for evaluating the ability of an antibody to detect prostate cancer.

Binding agents may be further linked to a reporter group, to facilitate diagnostic assays. Suitable reporter groups will be apparent to those of ordinary skill in the art, and include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Such antibodies may be polyclonal or monoclonal. In addition, the antibodies may be single chain, chimeric, CDR-grafted or humanized.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly, for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (ie., reactivity with the polypeptide of interest). Such cell lines may be produced, for example, from spleen cells obtained from an animal immunized as described above. The spleen cells are then immortalized by, for example,.fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various, techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process within, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. U.S. Pat. No. 4,673,562, to Davison et al. discloses representative chelating compounds and their synthesis.

A variety of routes of administration for the antibodies and immunoconjugates may be used. Typically, administration is intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Pharmaceutical Compositions and Vaccines

Within certain aspects, polypeptides, polynucleotides and/or binding agents may be incorporated into pharmaceutical compositions or vaccines. Pharmaceutical compositions comprise one or more such compounds and a physiologically acceptable carrier. Vaccines may comprise one or more such compounds and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain polynucleotides encoding one or more of the polypeptides as described above, such that the polypeptide is generated in situ. As noted above, the polynucleotides may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No.4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzrnan et al., *Cir. Res.* 73:1202–1207, 1993. Techniques for incorporating polynucleotides into such expression systems are well known to those of ordinary skill in the art. The polynucleotides may also be "naked," as described, for example, in Ulmer et al., *Science* 259:1745–1749, 1993 and reviewed by Cohen, *Science* 259:1691–1692, 1993. The uptake of naked polynucleotides may be increased by coating the polynucleotides onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Cancer Therapy

In further aspects of the present invention, the pharmaceutical compositions and vaccines described herein may be used for immunotherapy of cancer, such as prostate cancer, in a patient Polypeptides for use within such compositions and vaccines generally comprise an immunogenic portion of a prostate tumor protein, or a variant thereof. Such polypeptides may stimulate the patient's own immune response to prostate tumor cells. Alternatively, a pharmaceutical composition or vaccine may comprise one or more fusion proteins comprising one or more such polypeptides and/or polynucleotides encoding such one or more such polypeptides. Monoclonal antibodies of the present invention may also be used as therapeutic reagents, to diminish or eliminate prostate tumors. The antibodies may be used on their own (for instance, to inhibit metastases) or coupled to one or more therapeutic agents, as described above.

Within such methods, pharmaceutical compositions and vaccines are typically administered to a patient. As used herein, a "patient" refers to any warm-blooded animal, preferably a human. A patient may be afflicted with a disease, or may be free of detectable disease. Accordingly, the above pharmaceutical compositions and vaccines may be used to prevent the development of prostate cancer or to treat a patient afflicted with prostate cancer. Prostate cancer may be diagnosed using criteria generally accepted in the art. Pharmaceutical compositions and vaccines may be administered either prior to or following surgical removal of primary tumors and/or treatment such as administration of radiotherapy or conventional chemotherapeutic drugs.

Routes and frequency of administration, as well as dosage, will vary from individual to individual, and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against prostate tumor cells in a treated patient. A suitable immune response is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, the amount of polypeptide present in a dose (or produced in situ by the polynucleotides molecule in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 in to about 5 mL. A variety of routes of administration for the antibodies and immunoconjugates may be used. Typically, administration will be intravenous, intramuscular, subcutaneous or in the bed of a resected tumor. It will be evident that the precise dose of the antibody/imnnunoconjugate will vary depending upon the antibody used, the antigen density on the tumor, and the rate of clearance of the antibody.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transducers with a polynucleotide sequence, wherein said sequence contains a promoter region appropriate for increasing expression, and can be expressed as part of a recombinant virus or other expression system. Several viral vectors may be used to taansduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from tumor specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., Cancer Immunol Immunother, 45(3–4):131–6, 1997 and Hwu, P., et al, *Cancer Res*, 55(15).3369–73, 1995. Another embodiment may include the transfection of tumor antigen specific alpha and beta T cell receptor chains into alternate T cells, as in Cole, DJ, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 157:177, 1997).

Additionally, vectors expressing the disclosed polynucleotides may be introduced into stem cells taken from the patient and clonally propagated in vitro for autologous transplant back into the same patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

Methods Detecting Cancer

In general, a cancer may be detected in a patient based on the presence of one or more prostate tumor proteins and/or polynucleotides encoding such proteins in a biological sample obtained from the patient. In other words, such proteins may be used as markers to indicate the presence or absence of prostate cancer. The binding agents provided herein generally permit detection of the level of protein that binds to the agent in the biological sample. Alternatively, polynucleotide primers and probes may be used to detect the level of mRNA encoding an antigen, which is also indicative of the presence or absence of prostate cancer.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length prostate tumor proteins and portions thereof to which the binding agent binds, as described above.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a, well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigmna Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (comnonly a radioactive or fluorescent group or an enzyme). Enzyme reporter groups may generally be detected by the addition of substrate (generally for a specific period of time), followed by spectroscopic or other analysis of the reaction products.

To determine the presence or absence of prostate cancer, the signal detected from the reporter group that remains bound to the solid support is generally compared to a signal that corresponds to a predetermined cut-off value. In one preferred embodiment, the cut-off value for the detection of prostate cancer is the average mean signal obtained when the immobilized antibody is incubated with samples from patients without prostate cancer. In general, a sample generating a signal that is three standard deviations above the predetermined cut-off value is considered positive for prostate cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (ie., sensitivity) and false positive rates (100%-specificity) that correspond to each possible cut-off value for the diagnostic test result. The cut-off value on the plot that is the closest to the upper left-hand corner (ie., the value that encloses the largest area) is the most accurate cut-off value, and a sample generating a signal that is higher than the cut-off value determined by this method may be considered positive. Alterative, the cut-off value may be shifted to the left along the plot, to minimize the false positive rate, or to the right, to minimize the false negative rate. In general, a sample generating a signal that is higher than the cut-off value determined by this method is considered positive for prostate cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent Concentration of second binding agent at the area of immobilized antibody indicates the presence of prostate cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the antigens or binding agents of the present invention. The above descriptions are intended to be exemplary only.

In another embodiment, the above polypeptides may be used as markers for the progression of prostate cancer. In this embodiment, assays as described above for the diagnosis of prostate cancer may be performed over time, and the change in the level of reactive polypeptide(s) evaluated. For example, the assays may be performed every 24–72 hours for a period of 6 months to 1 year, and thereafter performed as needed. In general, prostate cancer is progressing in those patients in whom the level of polypeptide detected by the binding agent increases over time. In contrast, the cancer is not progressing when the level of reactive polypeptide either remains constant or decreases with time.

As noted above, prostate cancer may also, or alternatively, be detected based on the level of mRNA encoding a prostate tumor protein in a biological sample. For example, at least two oligonucleotide primers may be employed in a polymerase chain reaction (PCR) based assay to amplify a portion of a prostate tumor protein cDNA derived from a biological sample, wherein at least one of the oligonucleotide primers is specific for (ie., hybridizes to) a polynucleotide encoding the prostate tumor protein. The amplified cDNA is then separated and detected using techniques well known in the art, such as gel electrophoresis. Similarly, oligonucleotide probes that specifically hybridize to a polynucleotide encoding a prostate tumor protein may be used in a hybridization assay to detect the presence of polynucleotide encoding the antigen in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a prostate tumor protein that is at least 10 nucleotides, and preferably at least 20 nucleotides, in length. Oligonucleotide primers and/or probes which may be usefully employed in the diagnostic methods described herein preferably are at least 1040 nucleotides in length. In a preferred embodiment, the oligonucleotide primers comprise at least 10 contiguous nucleotides, more preferably at least 15 contiguous nucleotides, of a DNA molecule recited herein. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, N.Y., 1989).

One preferred assay employs RT-PCR, in which PCR is applied in conjunction with reverse transcription. Typically, RNA is extracted from a sample tissue and is reverse transcribed to produce cDNA molecules. PCR amplification using at least one specific primer generates a cDNA molecule, which may be separated and visualized using, for example, gel electrophoresis. Amplification may be performed on samples obtained from biological samples taken from a test patient and an individual who is not afflicted with prostate cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

Certain in vivo diagnostic assays may be performed directly on a tumor. One such assay involves contacting tumor cells with a binding agent The bound binding agent may then be detected directly or indirectly via a reporter group. Such binding agents may also be used in histological applications. Alternatively, polynucleotide probes may be used within such applications.

As noted above, to improve sensitivity, multiple prostate tumor protein markers may be assayed within a given sample. It will be apparent that binding agents specific for different antigens provided herein may be combined within a single assay. Further, multiple primers or probes may be used concurrently. The selection of antigen markers may be based on routine experiments to determine combinations that results in optimal sensitivity. In addition, or alternatively, assays for antigens provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a prostate tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a prostate tumor protein in a biological sample. Such kits generally comprise at least one oligonucleotide probe or primer, as described above, that hybridizes to a polynucleotide encoding a prostate tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a prostate tumor protein.

The following Examples are offered by way of illustration and not by way of limitation.

EXAMPLES

Example 1

ISOLATION AND CHARACTERIZATION OF PROSTATE TUMOR POLYPEPTIDES

This Example describes the isolation of certain prostate tumor polypeptides from a prostate tumor cDNA library.

A human prostate tumor cDNA expression library was constructed from Is prostate tumor poly A$^+$ RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly A$^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64 \times 10^7$ independent colonies, with 70% of clones having an insert and the average insert size being 1745 base pairs. The normal pancreas cDNA library contained $3.3 \times 10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood*, 84:189–199, 1994) with some modifications. Specifically, a prostate tumor-specific subtracted cDNA library was generated as follows. Normal pancreas cDNA library (70 $\mu$g) was digested with EcoRI, NotI, and SfuI, followed by a filling-in reaction with DNA polymerase Klenow fragment. After phenol-chloroform extraction and ethanol precipitation, the DNA was dissolved in 100 $\mu$l of H$_2$O, heat-denatured and mixed with 100 $\mu$l (100 $\mu$g) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 $\mu$l) was added and the biotinylation reaction was repeated., After extraction with butanol five times, the DNA was ethanol-precipitated and dissolved in 23 $\mu$l H$_2$O to form the driver DNA.

To form the tracer DNA, 10 $\mu$g prostate tumor cDNA library was digested with BamHI and XhoI, phenol chloroform extracted and passed through Chroma spin-400 columns (Clontech). Following ethanol precipitation, the tracer DNA was dissolved in 5 $\mu$l H$_2$O. Tracer DNA was mixed with 15 $\mu$l driver DNA and 20 $\mu$l of 2×hybridization buffer (1.5 M NaCl/10 mM EDTA/50 mM HEPES pH 7.5/0.2% sodium dodecyl sulfate), 6verlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 $\mu$l H$_2$O, mixed with 8 $\mu$l driver DNA and 20 $\mu$l of 2×hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant pBCSK+ (Stratagene, La Jolla, Calif. 92037) and trarsformed into ElectroMax E. coli DH10B cells by electroporation to generate a prostate tumor specific subtracted cDNA library (prostate subtraction 1).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GenBank databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 μg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the "subtracted prostate tumor specific cDNA library with spike".

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J3-25, J1-24, K1-58, K1-63, L1-14 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K1-48, K1-55, L1-2, L1-6, N1-1858, N1-1860, N1-1861, N1-1864 are provided in SEQ ID NOS: 30–40, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified-human pulmonary surfactant-associated protein, and the other (K1-48; SEQ ID NO:33) was determined to have some homology to R. norvegicus mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114. L1-12 is also referred to as P501S.

In a further experiment, four additional clones were identified by subtracting a prostate tumor cDNA library with normal prostate cDNA prepared from a pool of three normal prostate poly A+ RNA (prostate subtraction 2). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (prostate subtraction spike 2) was performed by subtracting a prostate tumor specific cDNA library with spike with normal pancreas cDNA library and further spiked with PSA, J1-17, pulmonary surfactant-associated protein, mitochondrial DNA, cytochrome c oxidase subunit II, N1-862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1G-4736, 1G-4738, 1G-4741, 1G-4744, 1G-4734, 1H-4774, 1H-4781, 1H-4785, 1H-4787, 1H-4796, 1I-4810, 1I-4811, 1J-4876, 1K-4884 and 1K-4896. The determined cDNA sequences for these clones are provided in SEQ ID NOS: 77–92, respectively. Comparison of these sequences with those in the gene bank as described above, revealed no significant homologies to 1G-4741, 1G-4734, 1I4807, 1J-4876 and 1K-4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1J-4876, 1K4884'and 1K4896, provided in SEQ ID NOS: 179–188 and 191–193, respectively, and to the determination of additional partial cDNA sequences for 1I-4810 and 1I-4811, provided in SEQ ID NOS: 189 and 190, respectively.

Additional studies with prostate subtraction spike 2 resulted in the isolation of three more clones. Their sequences were determined as described above and compared to the most recent Genbank. All three clones were found to have homology to known genes, which are Cysteine-rich protein, KIAA0242, and KIAA0280 (SEQ ID NO: 317, 319, and 320, respectively). Further analysis of these clones by Synteni microarray (Synteni, Palo Alto, Calif.) demonstrated that all three clones were over-expressed in most prostate tumors and prostate BPH, as well as in the majority of normal prostate tissues tested, but low expression in all other normal tissues.

An additional subtraction was performed by subtracting a normal prostate cDNA library with normal pancreas cDNA (prostate subtraction 3). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two novel clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Additionally, the full-length cDNA sequence for P509S (SEQ ID NO: 223) is provided in SEQ ID NO: 332.

Example 2

DETERMINATION OF ISSUE SPECIFICITY OF PROSTATE TUMOR POLYPEPTIDES

Using gene specific primers, mRNA expression levels for the representative prostate tumor polypeptides F1-16, H1-1, J1-17 (also referred to as P502S), L1-12 (also referred to as P501S), F1-12 (also referred to as P504S) and N1-1862 (also referred to as P503S) were examined in a variety of normal and tumor tissues using RT-PCR.

Briefly, total RNA was extracted from a variety of normal and tumor tissues using Trizol reagent as described above. First strand synthesis was carried out using 1–2 µg of total RNA with SuperScript II reverse transcripts (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 (P502S) and L1-12 (P501S) appear to be specifically over-expressed in prostate, with both genes being expressed at high levels in prostate tumor and normal prostate but at low to undetectable levels in all the other tissues examined. N1-1862 (P503S) was found to be over-expressed in 60% of prostate tumors and detectable in normal colon and kidney. The RT-PCR results thus indicate that F1-16, H1-1, J1-17 (P502S), N1-1862 (P503S) and L1-12 (P501S) are either prostate specific or are expressed at significantly elevated levels in prostate.

Further RT-PCR studies showed that F1-12 (P504S) is over-expressed in 60% of prostate tumors, detectable in normal kidney but nor detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancreases skeletal ≈scle, brain, stomach, testes, small intestine and bone marrow, showed that L1-12 (P501 S) is over-expressed in prostate tumors and normal prostate, while being undetectable in other normal tissues tested. J1-17 (P502S) was detected in two prostate tumors and not in the other tissues tested. N1-1862 (P503S) was found to be over-expressed in three prostate tumors and to be expressed in normal prostate, colon and kidney, but not in other tissues tested. F1-12 (P504S) was found to be highly expressed in two prostate tumors and to be undetectable in all other tissues tested.

The micro-array technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 (P501S) was found to be over-expressed in normal prostate and prostate tumor, with some expression being detected in normal skeletal muscle. Both J1-12and F1-12 (P504S) were found to be over-expressed in prostate tumor, with expression being lower or undetectable in all other tissues tested. N1-1862 (P503S) was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D4279 was found to be over-expressed in prostate tumor and normal prostate, expressed at lower levels in normal spinal cord, and to be undetectable in all other tissues tested.

Further studies to specifically address the extent to which P501 S (SEQ ID NO: 110) was expressed in breast tumor by microarray analysis revealed moderate over-expression in not only breast tumor, but also in metastatic breast tumor (2/31), with negligable to low expression in normal tisssues. This data suggests that P501S may be over-expressed in various breast tumors as well as in prostate tumors.

Example 3

ISOLATION AND CHARACTERIZATION OF PROSTATE TUMOR POLYPEPTIDES BY PCR-BASED SUBTRACTION

A cDNA subtraction library, containing cDNA from normal prostate subtracted with ten other normal tissue cDNAs (brain, heart, kidney, liver, lung, ovary, placental skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' $E.$ $coli$ (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38; P39, P42, P49, P50, P53, P55, P60, P64, P65, P73, P75, P76, P79 and P84. The determined cDNA sequences for these clones are provided in SEQ ID NO:4145, 47–52 and 54–65, respectively. P29, P47, P68, P80 and P82 (SEQ ID NO:46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. Larger cDNA clones containing the P20 sequence represent splice variants of a gene referred to as P703 P. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20, a portion of the P703P gene, was found to be highly expressed in normal prostate and prostate tumor, compared to all twelve normal tissues tested. A modest increase in express on of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast rumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P9 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8, 10-h10, 11-c8, 7-g6, 8-b5, 8-b6, 8-d4, 8-d9, 8-g3, 8-h11, 9-f12 and 9-f3. The determined DNA sequences for 10-d8, 10-h10, 11-c8, 8-d4, 8-d9, 8-h11, 9-f12 and 9-f3 are provided in SEQ ID NO: 207, 208, 209, 216, 217, 220, 221 and 222, respectively. The determined forward and reverse DNA sequences for 7-g6, 8-b5, 8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-f12 were found to show some homology to previously identified genes. Further characterization of 7-G6 and 8-G3 showed identity to the known genes PAP and PSA, respectively.

mRNA expression levels for these clones were determined using the mnicro-array technology described above. The clones 7-G6, 8-G3, 8-B5, 8-B6, 8-D4, 8-D9, 9-F3, 9-F 12, 9-H3, 10-A2, 10-A4, 11-C9 and 11-F2 were found to be over-expressed in prostate tumor and normal prostate, with expression in other tissues tested being low or undetectable. Increased expression of 8-F11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-B1 was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

PCR and hybridization-based methodologies were employed to obtain longer cDNA sequences for clone P20 (also referred to as P703P), yielding three additional cDNA fragments that progressively extend the 5' end of the gene. These fragments, referred to as P703PDE5, P703P6.26, and P703PX-23 (SEQ ID NO: 326, 328, and 330, with the predicted corresponding amino acid sequences in SEQ ID NO: 327, 329, and 331, respectively) contain additional 5' sequence. P703PDE5 was recovered by screening of a cDNA library (#141–26) with a portion of P703P as a probe. P703P6.26 was recovered from a mixture of three prostate tumor cDNAs and P703PX 23 was recovered from cDNA library (#438-48). Together, the additional sequences include all of the putative mature serine protease along with the majority of the putative signal sequence. Further studies using a PCR-based subtraction library of a prostate tumor pool subtracted against a pool of normal tissues (referred to as JP: PCR subtraction) resulted in the isolation of thirteen additional clones, seven of which did not share any significant homology to known Genbank sequences. The determined cDNA sequences for novel clones P711P, P712P, novel 23, P774P, P775P, P710P, and P768P are provided in SEQ ID NO: 307–311, 313, and 315, respectively. The remaining six clones (SEQ ID NO: 316, and 321–325) were shown to share homology to known genes. By microarray analysis, all thirteen clones showed three or more fold over-expression in prostate tissues, including prostate tumors, BPH, and normal prostate as compared to normal nonprostate tissues. Clones P711P, P712P, novel 23, and P768P showed over-expression in most prostate tumors and BPH tissues tested (n=29), and in the majority of normal prostate tissues (n=4), but background to low expression levels in all normal tissues. Clones P774P, P775P, and P710P showed comparatively lower expression and expression in fewer prostate tumors and BPH samples, with negative to low expression in normal prostate.

Using PCR and hybridization-based methodologies, additional cDNA sequence information was derived for two clones described above, 11-C9 and 9-F3, herein after referred to as P707P, and P714P, respectively (SEQ ID NO: 333 and 334). After comparison with the most recent Genbank, P707P was found to be a splice variant of the known gene HoxB13. While there are some differences in the published sequence and the derived cDNA sequence, the differences are likely due to allelic variation. In contrast, P714P does not share homology with a any known gene sequences and therefore is novel,.

Additionally, clones 8-B3, P89, P98, P130, and P201 (as disclosed in U.S. patent application No. 09/020,956, filed Feb. 9, 1998) were found to be contained within one contiguous sequence, referred to as P705P (SEQ ID NO: 335, with the predicted amino acid sequence provided in SEQ ID NO: 336), which was determined to be a splice variant of the known gene NKX 3.1.

Example 4

SYNTHESIS OF POLYPEPTIDES

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets nay then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

FURTHER ISOLATION AND CHARACTERIZATION OF PROSTATE TUMOR POLYPEPTIDES BY PCR-BASED SUBTRACTION

A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven novel clones were identified. Sequences of these partial cDNAs are provided in SEQ ID NOs:229 to 305. Most of these clones had no significant homology to database sequences. Exceptions were JPTPN23 (SEQ ID NO:23 1; similarity to pig valosin-containing protein), JPTPN30 (SEQ ID NO:234; similarity to rat mRNA for proteasome subunit), JTTPN45 (SEQ ID NO:243; similarity to rat norvegicus cytosolic NADP-dependent isocitrate dehydrogenase), JPTPN46 (SEQ ID NO:244; similarity to human subclone H8 4 d4 DNA sequence), JPID6 (SEQ ID NO:265; similarity to G. gallus dynein light chain-A), JP8D6 (SEQ ID NO:288); similarity to human BAC clone RG016J04), JP8F5 (SEQ ID NO:289; similarity to human subclone H8 3 b5 DNA sequence) and JP8E9 (SEQ ID NO:299; similarity to human Alu sequence).

The novel clones identified were:

| | |
|---|---|
| JPTPN13 | SEQ ID NO:229 |
| JPTPN14 | SEQ ID NO:230 |
| JPTPN23 | SEQ ID NO:231 |
| JPTPN24 | SEQ ID NO:232 |
| JPTPN25 | SEQ ID NO:233 |
| JPTPN30 | SEQ ID NO:234 |
| JPTPN34 | SEQ ID NO:235 |
| JPTPN35 | SEQ ID NO:236 |
| JPTPN36 | SEQ ID NO:237 |
| JPTPN38 | SEQ ID NO:238 |
| JPTPN39 | SEQ ID NO:239 |
| JPTPN40 | SEQ ID NO:240 |
| JPTPN41 | SEQ ID NO:241 |
| JPTPN42 | SEQ ID NO:242 |
| JPTPN45 | SEQ ID NO:243 |
| JPTPN46 | SEQ ID NO:244 |
| JPTPN51 | SEQ ID NO:245 |
| JPTPN56 | SEQ ID NO:246 |
| JPTPN64 | SEQ ID NO:247 |

-continued

| | |
|---|---|
| JPTPN65 | SEQ ID NO:248 |
| JPTPN67 | SEQ ID NO:249 |
| JPTPN76 | SEQ ID NO:250 |
| JPTPN84 | SEQ ID NO:251 |
| JPTPN85 | SEQ ID NO:252 |
| JPTPN86 | SEQ ID NO:253 |
| JPTPN87 | SEQ ID NO:254 |
| JPTPN88 | SEQ ID NO:255 |
| JP1F1 | SEQ ID NO:256 |
| JP1F2 | SEQ ID NO:257 |
| JP1C2 | SEQ ID NO:258 |
| JP1B1 | SEQ ID NO:259 |
| JP1B2 | SEQ ID NO:260 |
| JP1D3 | SEQ ID NO:261 |
| JP1A4 | SEQ ID NO:262 |
| JP1F5 | SEQ ID NO:263 |
| JP1E6 | SEQ ID NO:264 |
| JP1D6 | SEQ ID NO:265 |
| JP1B5 | SEQ ID NO:266 |
| JP1A6 | SEQ ID NO:267 |
| JP1E8 | SEQ ID NO:268 |
| JP1D7 | SEQ ID NO:269 |
| JP1D9 | SEQ ID NO:270 |
| JP1C10 | SEQ ID NO:271 |
| JP1A9 | SEQ ID NO:272 |
| JP1F12 | SEQ ID NO:273 |
| JP1E12 | SEQ ID NO:274 |
| JP1D11 | SEQ ID NO:275 |
| JP1C11 | SEQ ID NO:276 |
| JP1C12 | SEQ ID NO:277 |
| JP1B12 | SEQ ID NO:278 |
| JP1A12 | SEQ ID NO:279 |
| JP8G2 | SEQ ID NO:280 |
| JP8H1 | SEQ ID NO:281 |
| JP8H2 | SEQ ID NO:282 |
| JP8A3 | SEQ ID NO:283 |
| JP8A4 | SEQ ID NO:284 |
| JP8C3 | SEQ ID NO:285 |
| JP8G4 | SEQ ID NO:286 |
| JP8B6 | SEQ ID NO:287 |
| JP8D6 | SEQ ID NO:288 |
| JP8F5 | SEQ ID NO:289 |
| JP8A8 | SEQ ID NO:290 |
| JP8C7 | SEQ ID NO:291 |
| JP8D7 | SEQ ID NO:292 |
| JP8D8 | SEQ ID NO:293 |
| JP8E7 | SEQ ID NO:294 |
| JP8F8 | SEQ ID NO:295 |
| JP8G8 | SEQ ID NO:296 |
| JP8B10 | SEQ ID NO:297 |
| JP8C10 | SEQ ID NO:298 |
| JP8E9 | SEQ ID NO:299 |
| JP8E10 | SEQ ID NO:300 |
| JP8F9 | SEQ ID NO:301 |
| JP8H9 | SEQ ID NO:302 |
| JP8C12 | SEQ ID NO:303 |
| JP8E11 | SEQ ID NO:304 |
| JP8E12 | SEQ ID NO:305 |

Additional studies using the PCR-based subtraction library consisting of a prostate tumor pool subtracted against a normal prostate pool (referred to as PT-PN PCR subtraction) yielded three additional clones. Comparison of the cDNA sequences of these clones with the most recent Qenbank revealed two to be novel, herein after referred to as P715P and P767P (SEQ ID NO: 312 and 314). The remaining clone was shown to share homology to the known gene KIAA0056 (SEQ ID NO: 318). Using microarray analysis to measure mRNA expression levels in various tissues, all three clones were found to be over-expressed in prostate tumors and BPH tissues. Specifically, clone P715P was over-expressed in most prostate tumors and BPH tissues by a factor of three or greater, with elevated expression seen in the majority of normal prostate samples and in fetal tissue, but negative to low expression in all other normal tissues. Clone P767P was over-expressed in several prostate tumors

Example 6

PEPTIDE PRIMING OF MICE AND PROPAGATION OF CTL LINES 6.1. This Example illustrates the preparation of a CTL cell line specific for cells expressing the P502S gene.

Mice expressing the transgene for human HLA A2.1 (provided by Dr L. Sherman, The Scripps Research Institute, La Jolla, Calif.) were immunized with P2S #12 peptide (VLGWVAEL; SEQ ID NO: 306), which is derived from the P502S gene (also referred to herein as J1-17, SEQ ID NO:8), as described by Theobald et al., *Proc. Natl. Acad Sci. USA* 92:11993–11997, 1995 with the following modifications. Mice were immunized with 100 μg of P2S #12 and 120 μg of an I-A$^b$ binding peptide derived from hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (RPMI-1640 (Gibco BRL, Gaithersburg, Md.) containing 10% FCS, 2 mM Glutamine (Gibco BRL), sodium pyruvate (Gibco BRL), non-essential amino acids (Gibco BRL, 2×10$^{-5}$ M 2-mercaptoethanol, 50 U/ml penicillin and streptomycin) and cultured in the presence of irradiated (3000 rads) P2S#12 pulsed (5 mg/ml P2S #12 and 10 mg/ml β2-microglobulin) LPS blasts (A2 trnsgenic spleens cells cultured in the presence of 7 μg/ml dextran sulfate and 25 μg/ml LPS for 3 days). Six days later cells (5×10$^5$/ml) were restimulated with 2.5×10$^6$/ml peptide pulsed irradiated (20,000 rads) EL4A2Kb cells (Sherman et al, *Science* 258:815–818, 1992) and 3×10$^6$/ml A2 transgenic spleen feeder cells. Cells were cultured in the presence of 20 U/ml IL-2. Cells were continued to be restimulated on a weekly basis as mentioned, in preparation for cloning the line.

P2S#12 line was cloned by limiting dilution analysis with peptide pulsed EL4 A2Kb tumor cells (1×10$^4$ cells/ well) as stimulators and A2 transgenic spleen cells as feeders ( 5×10$^5$ cells/ well) grown in the presence of 30 U/ml IL-2. On day 14, cells were restimulated as before. On day 21, clones that were growing were isolated and maintained in culture. Several of these clones demonstrated reactivity (lysis) against human fibroblasts (HLA A2.1 expressing) transduced with P502S gene significantly higher than control fibroblasts. An example is presented in FIG. 1.

This data indicates that P2S #12 represents a naturally processed epitope of the P502S protein that is expressed in the context of the human HLA A2.1 molecule.

6.2. This Example illustrates the preparation of murine CTL lines and CTL clones specific for cells expressing the P501S gene.

Figure 3:
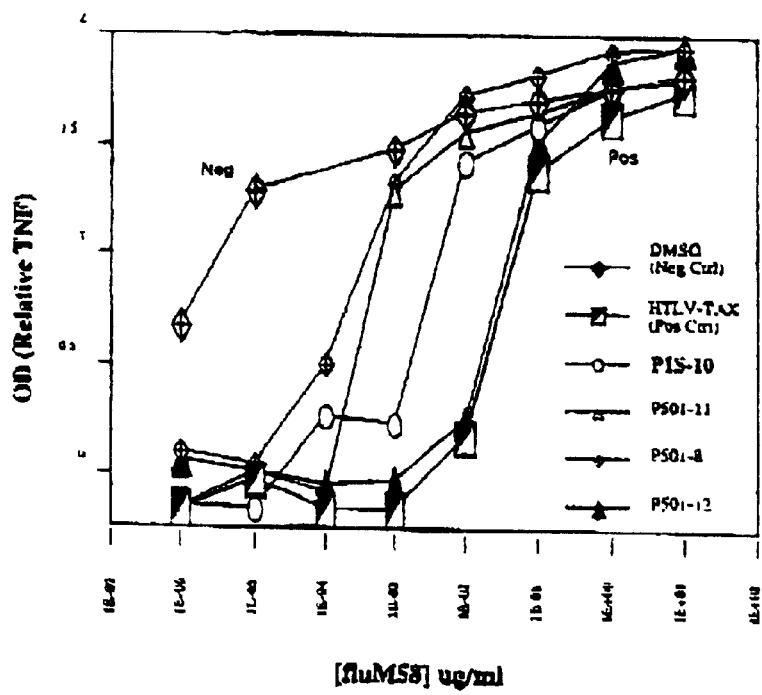
FIG. 3 represents a peptide competition binding assay showing that the P1S#10 peptide, derived from P501S, binds HLA-A2. Peptide P1S#10 inhibits HLA-A2 restricted presentation of fluM58 peptide to CTh clone D150M58 in TNF release bioassay. D150M58 CTh is specific for the HLA-A2 binding influenza matrix peptide fluM58.

This series of experiments were performed similarly to that described above. Mice were immunized with the P1S#10 peptide (SEQ ID NO: 337), which is derived from the P501S gene (also referred to herein as L1-12, SEQ ID NO: 110). The P1S#10 peptide was derived by analysis of the predicted polypeptide sequence for P501S for potential HLA-A2 binding sequences as defined by published HLA-A2 binding motifs (Parker, K C, et al, *J. Immunol.*, 152:163, 1994). P1S#10 peptide was synthesized by methods described in Example 4, and empirically tested for HLA-A2 binding using a T cell based competition assay. Predicted A2 binding peptides were tested for their ability to compete HLA-A2 specific peptide presentation to an HLA-A2 restricted CTL clone (D150M58), which is specific for the HLA-A2 binding influenza matrix peptide fluM58. D150M58 CTL secretes TNF in response to self-presentation of peptide fluM58. In the competition assay, test peptides at 100–200 ug/ml were added to cultures of D150M58 CTL in order to bind HLA-A2 on the CTL. After thirty minutes, CTL cultured with test peptides, or control peptides, were tested for their antigen dose response to the fluM58 peptide in a standard TNF bioassay. FIG. 3 shows peptide P1S#10 competes HLA-A2 restricted presentation of fluM58, demonstrating that peptide P1S#10 binds HLA-A2.

Figure 4:
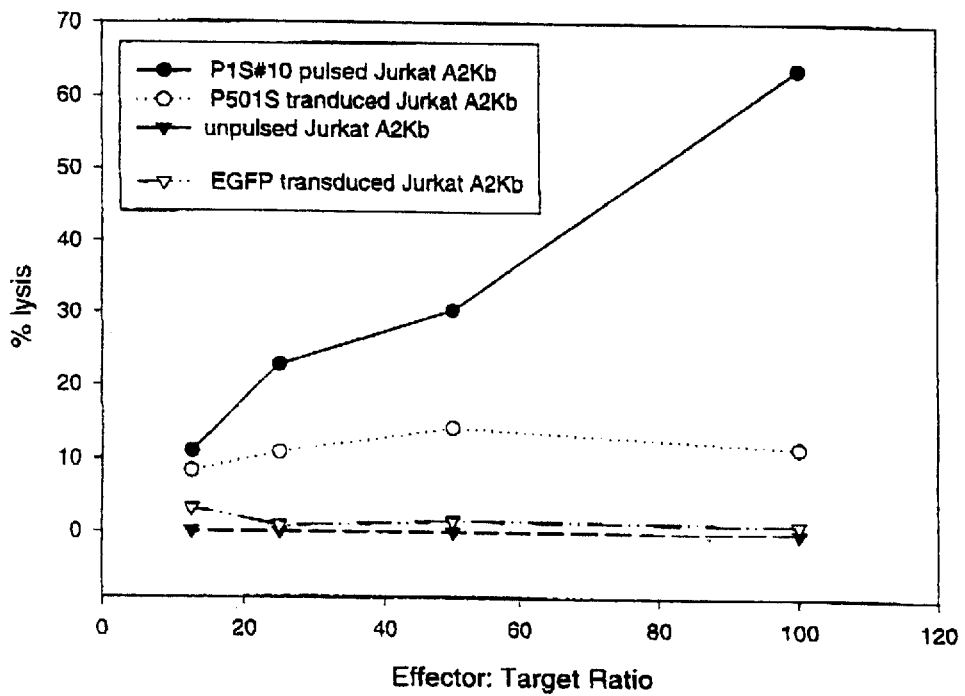
FIG. 4 is a graph illustrating the ability of T cell lines generated from P1S#10 immunized mice to specifically lyse P1S#10-pulsed Jurkat A2Kb targets and P501S-transduced Jurkat A2Kb targets, as compared to EGFP-transduced Jurkat A2Kb. The percent lysis is shown as a series of effector to target ratios, as indicated.

Mice expressing the tnansgene for human HLA A2.1 were immunized as described by Theobald et al., *Proc. Natl. Acad Sci. USA* 92:11993–11997, 1995 with the following modifications. Mice were inmmunized with 62.5 kg of P1S #10 and 120 μg of an I-A$^b$ binding peptide derived from Hepatitis B Virus protein emulsified in incomplete Freund's adjuvant. Three weeks later these mice were sacrificed and using a nylon mesh single cell suspensions prepared. Cells were then resuspended at 6×10$^6$ cells/ml in complete media (as described above) and cultured in the presence of irradiated (3000 rads) P1S#10 pulsed (2 μg/ml P1S#10 and 10 mg/ml β2-microglobulin) LPS blasts (A2 transgenic spleens cells cultured in the presence of 7 μg/ml dextran sulfate and 25 μg/ml LPS for 3 days). Six days later cells (5×10$^5$/ml) were restimulated with 2.5×10$^6$/ml peptide-pulsed irradiated (20,000 rads) EL4A2Kb cells, as described above, and 3×10$^6$/ml A2 trarisgenic spleen feeder cells. Cells were cultured in the presence of 20 U/ml IL-2. Cells were restimulated on a weekly basis in preparation for cloning. After three rounds of in vitro stimulations, one line was generated that recognized P1S#10-pulsed Jurkat A2Kb targets and P501S-transduced Jurkat targets as shown in FIG. 4.

Figure 5:
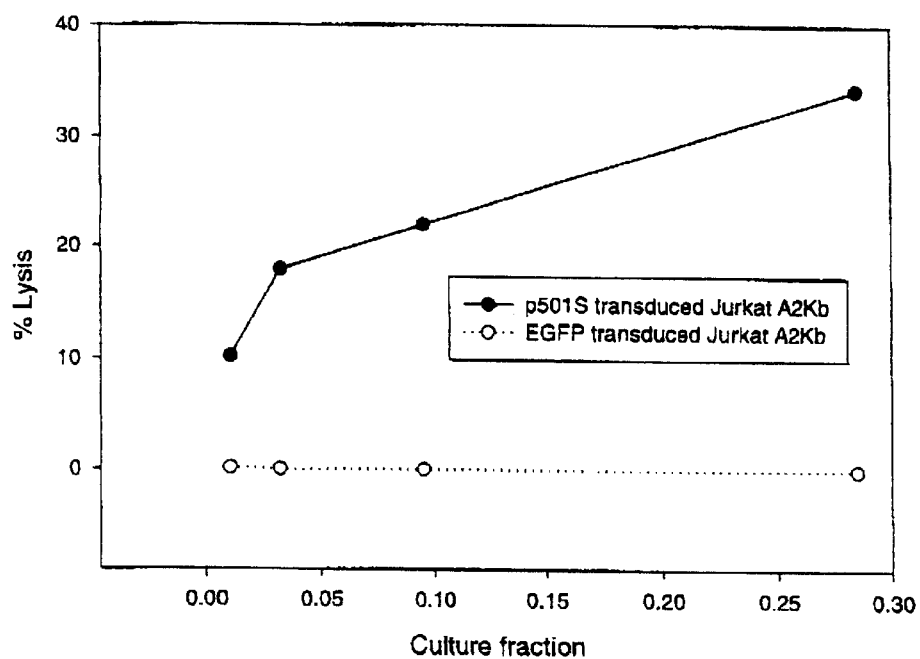
FIG. 5 illustrates the ability of a T cell clone to recognize and specifically lyse Jurkat A2Kb cells expressing the representative prostate tumor polypeptide P501 S, thereby demonstrating that the P1S#10 peptide may be a naturally processed epitope of the P501S polypeptide.

A P1S#10-specific CTL line was cloned by limiting dilution analysis with peptide pulsed EL4 A2Kb tumor cells (1×10$^4$ cells/ well) as stimulators and A2 tansgenic spleen cells as feeders (5×10$^5$ cells/well) grown in the presence of 30 U/ml IL-2. On day 14, cells were restimulated as before. On day 21, viable clones were isolated and maintained in culture. Five of these clones demonstrated specific cytolytic reactivity against P501S-transduced Jurkat A2Kb targets. As shown in FIG. 5, this data indicates that P1S#10 represents a naturally processed epitope of the P501S protein that is expressed in the context of the human HLA-A2.1 molecule.

Example 7

ABILITY OF HUMAN T CELLS TO RECOGNIZE PROSTATE TUMOR POLYPEPTIDES

This Example illustrates the ability of T cells specific for a prostate tumor polypeptide to recognize human tumor.

Figure 2A:
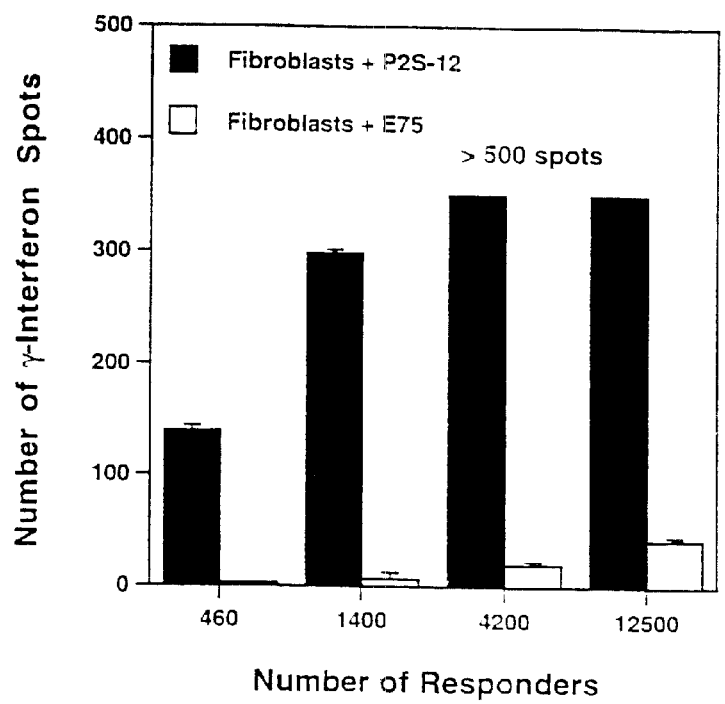
FIGS. 2A and 2B are graphs illustrating the ability of T cells to recognize cells expressing the representative prostate tumor polypeptide P502S. In each case, the number of γ-interferon spots is shown for different numbers of responders.
Figure 2B:
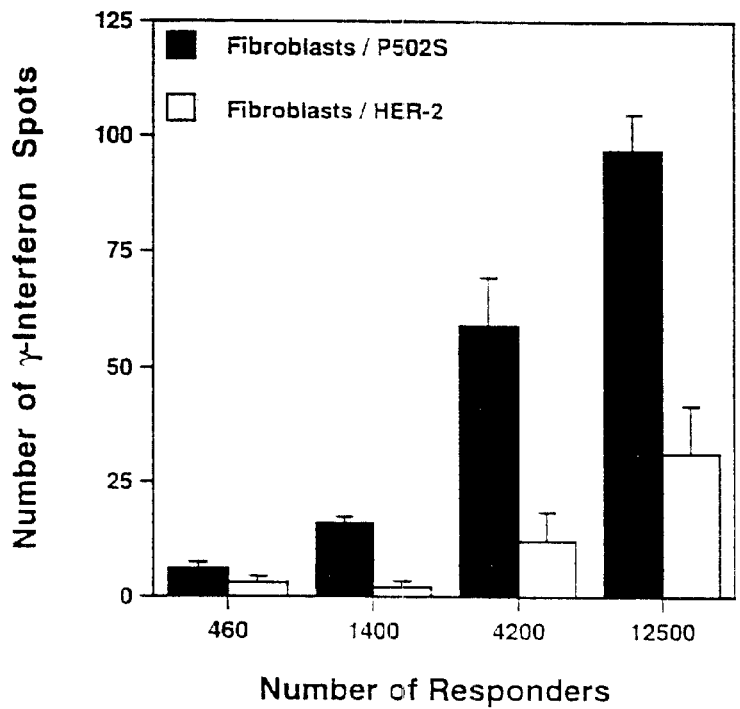

Human CD8$^+$ T cells were primed in vitro to the P2S-12 peptide (VLGWVAEL; SEQ ID NO:306) derived from the P502S (J1-17) gene using dendritic cells according to protocol set forth by Van Tsai et al., *Critical Reviews in Immunology* 18:65–75, 1998. The resulting CD8$^+$ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Experimental Medicine* 186:859–865, 1997). Briefly, titrating numbers of T cells were assayed in duplicate on 10$^4$ fibroblasts in the presence of 3 μg/ml human $β_2$-microglobulin and 1 μg/ml P2S-12 peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. In FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

Example 8

PRIMING OF CTL IN VIVO USING NAKED DNA IMMUNIZATION WITH A NOVEL PROSTATE ANTIGEN

The novel prostate tumor antigen L1-12, as described above, is also referred to as P501 S. HLA A2Kb Tg mice, (provided by Dr L. Sherman, The Scripps Research Institute, La Jolla, Calif.) were immunized with 100 ug VR10132-P501S either intramuscularly or intradennally. The mice were inmmunized three times, with a two week interval between immunizations. Two weeks after the last immunization, immune spleen cells were cultured with Jurkat A2Kb-P501S transduced stimulator cells. CTL lines were stimulated weekly. After two weeks of in vitro stimulation, CTL activity was assessed against P501S transduced targets. The results show that 2/8 mice developed strong anti-P501S CTL responses. These results demonstrate that P501S contains at least one naturally processed A2-restricted CTL epitope.

Example 9

GENERATION OF HUMAN CTL IN VITRO USING WHOLE GENE PRIMING AND STIMULATION TECHNIQUES WITH NOVEL PROSTATE TUMOR ANTIGEN

The novel prostate antigen L1-12, as described above, is also referred to as P501S. Using in vitro whole-gene priming with P501S-retrovirally transduced autologous fibroblasts, (see, for example, Yee et al, *The Journal of Immunology*, 157(9):4079–86, 1996) human CTL lines were derived that specifically recognize autologous fibroblasts transduced with P501S, as determined by interferon-γ ELISPOT analysis (as described above). Using a panel of HLA-mismatched fibroblast lines transduced with P501S, these CTL lines were shown to be restricted HLA-A2 class I allele. Specifically, dendritic cells (DC) were differentiated from monocyte cultures derived from PBMC of normal human donors by growth for five days in RPMI medium containing 10% human serum and 50 ng/ml human GM-CSF and 30 ng/ml human IL-4. Following culture, DC were infected overnight with recombinant P501S vaccinia virus at a multiplicity of infection (M.O.I) of five, and matured overnight by the addition of 3 ug/ml. CD40 ligand. Virus was inactivated by U.V. irradiation and CD8+ T cells were isolated using a magnetic bead system, and priming cultures were initiated using standard culture techniques. Cultures were restimulated every 7–10 days using autologous primary fibroblasts retrovirally transduced with P501S. Following four stimulations cycles, CD8+ T cell lines could be identified that specifically produced interferon-γ when stimulated with P501S-transduced autologous fibroblasts; the P501S-specific activity could be sustained by the continued stimnulation of the cultures with P501S-transduced fibroblasts in the presence of IL-15. A panel of HLA-mismatched fibroblast lines transduced with P501S were generated to define the restriction allele of the response. By measuring Interferon-γ in an ELISPOT assay, the P501S specific response was shown to be restricted by HLA-A2. These results demonstrate that a CD8+ CTL response to P501S can be elicited.

Example 10

IDENTIFICATION OF A NATURALLY PROCESSED CTL EPITOPE CONTAINED WITHIN A NOVEL PROSTATE TUMOR ANTIGEN

The novel prostate antigen P20, as described above, is also referred to as P703P. The 9-mer peptide, p5, having an amino acid sequence of LLANDLMLI, (SEQ ID NO: 338) was derived from the P703P antigen. The p5 peptide is immunogenic in human HLA-A2 donors and is a naturally processed epitope. Antigen specific CD8+ T cells can be primed following repeated in vitro stimulations with monocytes pulsed with p5 peptide. These CTL specifically recognize p5-pulsed target cells in both ELISPOT (described above), and chromium release assays. Additionally, in HLA-A2 transgenic mice (described above), immunization with p5 leads to the generation of CTL lines which recognize a variety of P703P transduced target cells expressing either HLA-A2Kb or HLA-A2. Specifically, HLA-A2 tansgenic mice were immunized subcutaneously in the footpad with 100 ug of p5 peptide formulated together with 140 ug of hepatitis B virus core peptide (a Th peptide) in Freund's incomplete adjuvant. Three weeks post immunization, spleen cells from immunized mice were stimulated in vitro with peptide-pulsed LPS blasts. CTL activity was assessed by chromium release assay five days after primary in vitro stimulation. Retrovirally transduced cells expressing P703P, or control antigen, and HLA-A2Kb were used as targets. CTL lines specifically recognized both p5-pulsed targets as well as P703P-expressing targets have been identified.

Human in vitro priming experiments have been conducted that demonstrate the p5 peptide is immunogenic in humans. Dendritic cells (DC) were differentiated from monocyte cultures derived from PBMC of normal human donors by culturing for five days in RPMI medium containing 10% human serum and 50 ng/ml human GM-CSF and 30 ng/ml human IL-4. Following culture, the DC were pulsed with p5 peptide and cultured with GM-CSF and IL4 together with CD8+ T cell enriched PBMC. CTL lines were restimulated in a weekly basis using p5-pulsed monocytes in subsequent stimulations. Five to six weeks after initiation of the CTL cultures, CTL recognition of p5-pulsed target cells was demonstrated.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

What is claimed is:

1. An isolated monoclonal antibody, or antigen-binding fragment thereof, that specifically binds to a polypeptide comprising the amino acid sequence of SEQ ID NO: 108.

2. A method for detecting the presence of a cancer in a patient, comprising the steps of:
   (a) obtaining a biological sample from the patient;
   (b) contacting the biological sample with an antibody, or antigen-binding fragment thereof, that specifically binds to a polypeptide comprising the amino acid sequence set forth in SEQ ID NO: 108;
   (c) detecting in the sample an amount of polypeptide that binds to the binding agent; and
   (d) comparing the amount of polypeptide to a predetermined cut-off value and therefrom determining the presence of a cancer in the patient.

3. A composition comprising a first component selected from the group consisting of physiologically acceptable carriers and immunostimulants, and a second component selected from the group consisting of an antibody, or antigen-binding fragment thereof, that specifically binds to a polypeptide comprising the amino acid sequence set forth in SEQ ID NO: 108.

4. A cancer diagnostic kit comprising at least one antibody, or antigen-binding fragment thereof, that specifically binds to a polypeptide comprising the amino acid sequence set forth in SEQ ID NO: 108 and a detection reagent, wherein the detection reagent comprises a reporter group.

* * * * *